United States Patent
Kimoto et al.

(10) Patent No.: US 7,266,459 B2
(45) Date of Patent: Sep. 4, 2007

(54) GAS DETECTOR AND AUTOMOBILE VENTILATION SYSTEM

(75) Inventors: Yuji Kimoto, Aichi (JP); Toshiya Matsuoka, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 1356 days.

(21) Appl. No.: 10/048,535

(22) PCT Filed: May 28, 2001

(86) PCT No.: PCT/JP01/04457

§ 371 (c)(1),
(2), (4) Date: Jun. 10, 2002

(87) PCT Pub. No.: WO01/92864

PCT Pub. Date: Dec. 6, 2001

(65) Prior Publication Data

US 2002/0154019 A1    Oct. 24, 2002

(30) Foreign Application Priority Data

May 31, 2000    (JP) .............................. 2000-162595

(51) Int. Cl.
*G06F 15/00* (2006.01)
(52) U.S. Cl. .......................................... 702/24; 73/23.2
(58) Field of Classification Search ................ 702/24, 702/23, 183, 184, 189; 73/1.02, 1.06, 19.01, 73/23.2, 23.21–23.22, 23.4
See application file for complete search history.

(56) References Cited

U.S. PATENT DOCUMENTS

| 4,730,590 A | 3/1988 | Sogawa |
| 5,426,937 A | 6/1995 | Ohuchi et al. |

OTHER PUBLICATIONS

Japanese Abstract No. 05 157714, dated Jun. 25, 2003, Jun. 25, 1993.

*Primary Examiner*—Edward Raymond
(74) *Attorney, Agent, or Firm*—Sughrue Mion, PLLC

(57) ABSTRACT

It is an object of the invention to provide a gas detecting device capable of relieving the influence of an environment such as a temperature, a humidity or a wind velocity to detect a change in a concentration of a specific gas and an autoventilation system for a vehicle using the gas detecting device.

More specifically, a gas detecting device (10) using a gas sensor element (11) changing a sensor resistance Rs depending on a concentration of a gas such as NOx and an autoventilation system (100) for a vehicle according to the invention A/D convert the output of a sensor resistance value converting circuit (14) to acquire a sensor output value $S(n)$, calculates a base value $B(n)$ based on $B(n)=B(n-1)+k1\{S(n)-B(n-1)\}$, and furthermore, calculates a difference value of $D(n)=S(n)-B(n)$. When the concentration of the gas is increased so that the difference value becomes greater than a predetermined concentration threshold, a high concentration signal is generated to close a flap (34) and a base value $B(n)$ is calculated by using a coefficient k2 which is smaller than k1 based on $B(n)=B(n-1)+k2\{S(n)-B(n-1)\}$.

19 Claims, 24 Drawing Sheets

GAS DETECTOR AND AUTOMOBILE VENTILATION SYSTEM

TECHNICAL FIELD

The present invention relates to a gas detecting device for detecting a change of a specific gas concentration in an environment and an autoventilation system for a vehicle using the gas detecting device.

BACKGROUND ART

Conventionally, there has been known a gas sensor element using lead-phthalocyanine or an oxide semiconductor such as $WO_3$ or $SnO_2$, that is, a gas sensor element capable of changing an electrical characteristic (for example, a sensor resistance value) with a variation in the concentration of a specific gas, for example, an oxidizing gas such as NOx in an environment or a reducing gas such as CO or HC and detecting the variation in the concentration of the specific gas based on the change of the electrical characteristic. Moreover, there has also been known a gas detecting device using the gas sensor element. Furthermore, there have been known various control systems using the gas detecting device, for example, a system for controlling the switching operation of a flap for switching the introduction of outside or inside air into a vehicle compartment depending on the situation of contamination of air outside the vehicle compartment, for example, a system for detecting the contamination of room air by smoking or the like and controlling an air cleaner, and the like.

As is disclosed in Japanese Unexamined Patent Publication No. Hei 5-157714, for example, there has been known a gas detecting device using a second differential value obtained by differentiating the output signal of a gas sensor element or A/D converting an analog differential value and then digitally differentiating the converted value in order to enhance the sensitivity of the change in a gas concentration to quickly take a countermeasure against the change in the concentration and to enhance S/N for a noise such as a wind. In International Patent Publication No. 501095/1989, moreover, there has been disclosed a gas detecting device for integrating a sensor signal and comparing the integral value with the sensor signal to detect a gas.

However, the gas detecting device using the gas sensor element in which a sensor resistance value is changed by a variation in the concentration of a specific gas has such a property that the sensor resistance value also fluctuates by the influence of other environments such as a temperature, a humidity or a wind velocity in addition to the change in the concentration of the specific gas. For this reason, the gas detecting device using a differential value detects a relative change in an output signal. The output signal is greatly changed by other environments such as a temperature, a humidity or a wind velocity in addition to the change in the concentration of the specific gas. Therefore, it is impossible to decide whether the output signal is changed by the concentration of the specific gas or a disturbance such as a change in the humidity based on only the relative change in the output signal. More specifically, in the case in which the differential value or the second differential value of the output signal of the gas sensor element is used, it is possible to grasp a time that the gas concentration fluctuates (for example, the gas concentration is rapidly increased). However, it is hard to know the degree of the change in the gas concentration, the subsequent situation of the change in the gas concentration or a time that the gas concentration is reduced.

On the other hand, in the gas detecting device for detecting a gas by comparing the integral value of a sensor signal with the sensor signal itself, a change in the integral value is more delayed than a change in the concentration of a specific gas. Therefore, when the concentration of the specific gas is once started to be reduced, the integral value becomes greater than the sensor signal in some cases. For this reason, when the concentration of the specific gas is then increased again, the increase in the concentration of the specific gas cannot be detected early so that the change in the concentration of the specific gas cannot be detected properly, that is, a detection timing is delayed because the integral value is greater than the sensor signal irrespective of the start of the increase in the concentration of the specific gas (therefore, the sensor signal).

In order to detect an increase and a reduction in the concentration of the specific gas, it is expected that an increase period for the concentration should be grasped as early as possible while relieving the influence of the environment such as a temperature or a humidity, that is, an initial stage for the increase in the concentration of the specific gas should be grasped to generate a signal indicating that the concentration of the specific gas is increased. On the other hand, it is expected that a signal indicating that the concentration is reduced should be generated after the concentration is sufficiently reduced in a reduction period for the concentration. As in the conventional art using differentiation, integration or the like in which both of the increase and the reduction in the concentration are decided based on a value (a differential value or the like) calculated by the same calculating method, however, it is hard to properly grasp both the initial stage of the increase and the reduction period for the concentration to generate each signal.

The invention has been made in consideration of such problems and has an object to provide a gas detecting device capable of properly grasping increase and reduction periods for the concentration of a specific gas to generate each signal, that is, a gas detecting device capable of relieving the influence of an environment such as a temperature, a humidity or a wind velocity to detect a change in the concentration of the specific gas with high precision and an autoventilation system for a vehicle using the gas detecting device.

DISCLOSURE OF THE INVENTION

As a solution, there is provided a gas detecting device using a gas sensor element changing an electrical characteristic depending on a concentration of a specific gas, comprising acquiring means for acquiring a sensor output value by using the gas sensor element, first deciding means for deciding whether or not a first deciding object value calculated by using the sensor output value satisfies a first relationship for a first threshold, second deciding means for deciding whether or not a second deciding object value calculated by using the sensor output value through a different calculating method from the method of calculating the first deciding object value satisfies a second relationship for a second threshold, concentration signal generating means for generating either a low concentration signal or a high concentration signal, and concentration signal generating means for generating the high concentration signal in place of the low concentration signal when the first relationship is satisfied by the first deciding means for a period in which the low concentration signal is generated, and for generating the low concentration signal in place of the high concentration signal when the second relationship is satisfied by the second deciding means for a period in which the high concentration signal is generated.

According to the gas detecting device of the invention, when the first deciding object value calculated by using the sensor output value satisfies the first relationship for the first threshold for the period in which the concentration of the specific gas is low (the period in which the low concentration signal is generated) the high concentration signal Is generated in place of the low concentration signal. On the other hand, when the second deciding object value calculated by using the sensor output value through the calculating method different from the method for the first deciding object value satisfies the second relationship for the second threshold for the period in which the concentration is high (the period in which the high concentration signal is generated), the low concentration signal is generated in place of the high concentration signal. In addition, the calculating method of calculating the first deciding object value is different from the calculating method of calculating the second deciding object value for the period in which the high concentration signal is generated. More specifically, the first and second relationships are decided by using the first deciding object value and the second deciding object value which are calculated by the different calculating means in the cases in which the concentration of the specific gas is low and high. Therefore, it is possible to decide a change in the concentration of the specific gas on proper conditions depending on the period in which the low concentration signal or the high concentration signal is generated respectively.

Thus, it is possible to set conditions suitable for detecting a period in which the concentration of the specific gas is increased or reduced, for example, to adapt to the sense of smell of men. For example, the high concentration signal is generated as early as possible while relieving the influence of an environment such as a temperature or a humidity for the period in which the concentration is increased, while the low concentration signal can be set to be generated in such a timing that the concentration is fully reduced for the period in which the concentration is reduced. Accordingly, proper control can be carried out in the autoventilation system for a vehicle, switching to inside air circulation is carried out in the early stage in which the concentration of the specific gas in outside air is increased and switching to outside air circulation can be carried out when the concentration is fully reduced, for example.

The first deciding object value and the second deciding object value are calculated by using the sensor output value through the different certain calculating methods, respectively. Examples of the first deciding object value and the second deciding object value include a differential value, a second differential value and the like. In addition, there is a difference value between the sensor output value and an integral value, a difference value between a sensor output value S(n) and a base value B(n) obtained by an equation of B(n)=B(n−1)+k{S(n)−B(n−1)} or a difference value between the sensor output value S(n) and a moving average value Md(n) of the sensor output values.

In some cases, moreover, the calculating methods of calculating the first deciding object value and the second deciding object value are completely different from each other, for example, a differential value is obtained by one of the calculating methods and a moving average value is obtained by the other calculating method. In addition, the moving average values of 30 sensor output values are obtained by one of the calculating methods and the moving average values of 50 sensor output values are obtained by the other calculating method. Furthermore, the same calculating method is used to vary a predetermined coefficient value set in a calculating equation and to weight a value calculated based on the sensor output value.

Electrical characteristics to be changed in the gas sensor element include a resistance value, electromotive force, a current, a capacitance, an inductance and the like. Moreover, means for acquiring the sensor output value is preferably constituted such that the sensor output value can be properly acquired depending on a change in the electrical characteristic of the gas sensor element or a processing format such as an analog processing or a digital processing. For example, an A/D conversion processing or the like is included in the case in which the digital processing is to be carried out.

In the gas detecting device, furthermore, the high concentration signal includes a plurality of concentration level signals corresponding to a plurality of concentration levels of the specific gas respectively, and there is provided third deciding means for deciding whether or not the second deciding object value and a plurality of interlevel thresholds corresponding to interlevel boundaries between the concentration levels with one to one satisfy predetermined relationships respectively.

It is preferable that the concentration signal generating means should generate a concentration level signal corresponding to any concentration level of the high concentration signal in place of the low concentration signal when the first relationship is satisfied by the first deciding means for a period in which the low concentration signal is generated, should generate the concentration level signal corresponding to a concentration level which is higher than the current concentration level for a period in which any concentration signal belonging to the high concentration signal when the second deciding object value satisfies the predetermined relationship for the interlevel threshold corresponding to the interlevel boundary between the current concentration level and the concentration level which is higher than the current concentration level by one rank, should generate the concentration level signal corresponding to a lower concentration level than the current concentration level for a period in which any concentration signal belonging to the high concentration signal when the second deciding object value does not satisfy the predetermined relationship for the interlevel threshold corresponding to the interlevel boundary between the current concentration level and the concentration level which is lower than the current concentration level by one rank, and should generate the low concentration signal in place of the high concentration signal when the second relationship is satisfied by the second deciding means for a period in which any concentration signal belonging to the high concentration signal.

Since the high concentration signal thus includes a plurality of concentration level signals, the concentration level signals can be switched depending on the concentration of the specific gas also during the generation of the high concentration signal. For this reason, it is possible to know the degree of the concentration, that is, the concentration of the specific gas is comparatively low or high during the generation of the high concentration signal. In the autoventilation system for a vehicle, moreover, it is possible to carry out a fine control to set a proper opening, for example, to half open a flap in addition to full closing or full opening.

Furthermore, it is preferable that the gas detecting device should comprise second calculating means for calculating a second difference value to be a difference between the sensor output value and a second calculated value which is calculated by using the sensor output value and carries out follow-up more slowly than the sensor output value when the sensor output value is changed, the second deciding means serving to decide whether or not the second difference value to be the second deciding object value satisfies the second relationship for the second threshold.

In the gas detecting device, the second calculated value is changed more slowly than the sensor output value. For example, in the case in which the sensor output value is increased with an increase in the concentration of the specific gas based on the relationship of the characteristic of the acquiring means, the second the sensor output value. The gas sensor element changing an electric characteristic (for example, a sensor resistance value) depending on the concentration of the specific gas is influenced by an environment such as a temperature or a humidity or a wind velocity as well as a change in the concentration of the specific gas. In some cases in which the concentration of the specific gas is constant, the sensor output value is gradually changed, that is, a drift is caused. First of all, it is assumed that the acquiring means having such a characteristic as to increase the sensor output value with a rise in the concentration of the specific gas is used. When a drift is generated in such a direction that the sensor output value is increased for a period in which the concentration of the specific gas is raised and is then reduced, the sensor output value is reduced to a value which is greater than a value obtained before the rise even if the concentration of the specific gas is actually reduced to the same level as that obtained before the rise.

In this case, if the second calculated value is not changed but is maintained to be constant, the second difference value to be the difference between the sensor output value and the second calculated value is also reduced to the greater value than the value obtained before the rise. Accordingly, although the concentration of the specific gas is actually reduced sufficiently, there is a possibility that it might be erroneously decided that the concentration of the specific gas is high and a reduction in the concentration of the gas cannot be discriminated because the second difference value is great. On the other hand, in the case in which a value to be increased in a predetermined pattern which is changed, and does not follow the sensor output value and is not related thereto, for example, a value to be increased rectilinearly with a constant gradient with the passage of time is used for the second calculated value, the above-mentioned drawbacks are not caused. However, as in a long tunnel, for example, in some cases in which the concentration of the specific gas is high for a long period of time or the sensor output value is not greatly increased, the second difference value to be the difference between the sensor output value and the second calculated value is smaller than the second threshold so that the low concentration signal is generated irrespective of such a state that the concentration of the specific gas is high.

On the other hand, according to the invention, the second calculated value is slowly changed following the sensor output value on the assumption described above. Therefore, even if the drift is generated in such a direction that the sensor output value is increased, the second difference value is gradually decreased with the passage of time. For this reason, in the case in which the concentration of the specific gas is reduced, the second difference value becomes smaller than the second threshold so that the low concentration signal can always be generated. In addition, since the second calculated value slowly follows the sensor output value, the second calculated value corresponds to the sensor output value differently from the case in which the second calculated value is increased in the predetermined pattern. Therefore, the low concentration signal can be prevented from being generated in such a state that the concentration of the specific gas is high. In the autoventilation system for a vehicle and a control system for an air cleaner, accordingly, a proper control can be carried out, that is, a flap is opened or a fan is rotated at a low speed when some time passes.

On the other hand, in the case in which the sensor output value is decreased with an increase in the concentration of the specific gas reversely to the assumption in respect of the characteristic of the acquiring means, a reduction in the concentration of the specific gas can be detected in the same manner reversely to the foregoing. Accordingly, if the relationship between the second difference value and the second threshold is properly set depending on the characteristic of the acquiring means and the property of the second calculated value, it is possible to properly detect the reduction in the concentration of the specific gas based on a decision whether or not the relationship is satisfied by the second deciding means.

Furthermore, it is preferable that the gas detecting device should comprise first calculating means for calculating a first difference value to be a difference between the sensor output value and a first calculated value which is calculated by using the sensor output value and carries out follow-up more sensitively than the second calculated value when the sensor output value is changed, the first deciding means serving to decide whether or not the first difference value to be the first deciding object value satisfies the first relationship for the first threshold.

Description will be given to the case in which the first difference value is compared with the first threshold. As described above, in the case in which the concentration of the specific gas is increased so that the sensor output value is changed for the period in which the low concentration signal is generated, the first calculated value is changed with follow-up more sensitively as compared with the case in which the second calculated value is used. In other words, the first calculated value follows the sensor output value more rapidly as compared with the second calculated value. Also in the case in which the sensor output value fluctuates (drifts) slowly by the influence of a temperature, a humidity or the like in such a state that the concentration of the specific gas is low, the first calculated value is changed with follow-up. Therefore, it is possible to suppress of the influence of the drift and to prevent the erroneous detection of a change in the concentration of the gas by the influence of the drift. However, when the concentration of the specific gas is increased so that the sensor output vale is changed quickly and greatly, the first calculated value cannot sufficiently follow but the first difference value is increased. Therefore, the first difference value satisfies a predetermined relationship with the first threshold so that the high concentration signal is generated. Thus, it is possible to detect an increase in the concentration of the gas in the comparatively early stage of the increase in the concentration of the specific gas and to generate the high concentration signal while suppressing the influence of the drift.

It is sufficient that the first calculated value is changed more sensitively than the second calculated value when the sensor output value is changed. For example, there is an integral value calculated by making an integral constant smaller than that in the second calculating method, a base value B(n) calculated based on an equation of $B(n)=B(n-1)+k1\{S(n)-B(n-1)\}$ by using a coefficient k1 which is greater than a coefficient k2 used in the second calculating method (k1>k2), m1 moving average value Md calculated by a sample number m1 of sensor output values which is smaller than a sample number m2 of the moving average values obtained by the second calculating method (m1<m2) or the like.

As another solution, furthermore, there is provided a gas detecting device using a gas sensor element changing an electrical characteristic depending on a concentration of a specific gas, comprising acquiring means for acquiring a sensor output value by using the gas sensor element, concentration level signal switching generating means for switching and generating a plurality of concentration level signals corresponding to a plurality of concentration levels, respectively, first deciding means for deciding whether or not a first deciding object value calculated by using the sensor output value satisfies a first relationship for a first threshold, and second deciding means for deciding whether or not a second deciding object value calculated by using the sensor output value through a different calculating method from the method of calculating the first deciding object value and a plurality of interlevel thresholds corresponding to interlevel boundaries between the concentration levels with one to one satisfy predetermined relationships, respectively, wherein the concentration level signal switching generating means generates a concentration level signal corresponding to a concentration level which is higher than the lowest concentration level by one rank in place of a concentration level signal corresponding to the lowest concentration level when the first relationship is satisfied by the first deciding means for a period in which the concentration level signal corresponding to the lowest concentration level is generated, and generates the concentration level signal corresponding to a higher concentration level than a current concentration level when the second deciding object value satisfies the predetermined relationship for the interlevel threshold corresponding to the interlevel boundary between the current concentration level and the concentration level which is higher than the current concentration level by one rank, and generates the concentration level signal corresponding to a lower concentration level than the current concentration level when the second deciding object value does not satisfy the predetermined relationship for the interlevel threshold corresponding to the interlevel boundary between the current concentration level and the concentration level which is lower than the current concentration level by one rank.

According to the gas detecting device of the invention, if the first deciding object value calculated by using the sensor output value satisfies the first relationship for the first threshold for the period in which the lowest concentration level signal is generated, that is, the concentration level is the lowest, a concentration level signal which is higher by one rank (that is, a second lowest) is generated in place of the lowest concentration level signal. On the other hand, if the second deciding object value satisfies the predetermined relationship for the interlevel threshold corresponding to the interlevel boundary between the current concentration level and the concentration level which is higher than the current concentration level by one rank for the period in which the concentration level signal which is higher than the lowest concentration level signal is generated, the concentration level signal which is higher than the current concentration level is generated. For example, in the case in which such a relationship that the second deciding object value is greater than the interlevel threshold is satisfied, a higher concentration level signal is generated. To the contrary, when the second deciding object value satisfies the predetermined relationship for the interlevel threshold corresponding to the interlevel boundary between the current concentration level and the concentration level which is lower than the current concentration level by one rank, the concentration level signal which is lower than the current concentration level is generated.

More specifically, in the case in which the concentration of the specific gas is low (the concentration level is the lowest) and the case in which the concentration is higher (the concentration level is higher than the lowest concentration level), the first relationship or the predetermined relationship is decided by using the first deciding object value and the second deciding object value which are calculated through different certain calculating methods. The details of the first deciding object value, the second deciding object value and the different calculating methods of calculating them are the same as described above. Accordingly, it is possible to carry out a decision on proper conditions corresponding to the concentration of the specific gas in the cases in which the concentration level is the lowest and is higher than the lowest concentration level. In addition, in the case in which the concentration of the specific gas is high, a plurality of concentration levels can be decided. More specifically, it is possible to generate a signal corresponding to three kinds of concentration levels or more as a whole. Consequently, a control can be carried out more appropriately, that is, a flap is opened and closed on proper conditions corresponding to the respective concentration level signals.

As a solution, there is provided a gas detecting device using a gas sensor element changing a sensor resistance depending on a concentration of a specific gas, comprising a sensor resistance value converting circuit for outputting a sensor output potential depending on a change in a sensor resistance value by conducting to the gas sensor element, the sensor output potential being raised when the concentration of the specific gas is increased, A/D converting means for A/D converting the sensor output potential every predetermined time, thereby acquiring a sensor output value, first base value calculating means for calculating a base value from the sensor output value in accordance with the following equation (1), $$B(n)=B(n-1)+k1\{S(n)-B(n-1)\} \quad (1)$$

wherein S(n) represents a sensor output value, B(n) represents a base value, k1 represents a first coefficient, 0<k1<1 is set, and n is an integer indicative of an order of time series, difference value calculating means for calculating a difference value D(n) from the sensor output value S(n) and the base value B(n) in accordance with the following equation (2), $$D(n)=S(n)-B(n) \quad (2)$$

wherein D(n) represents a difference value, concentration signal generating means for generating either a low concentration signal or a high concentration signal, the concentration signal generating means generating the high concentration signal when the difference value is greater than a predetermined concentration threshold, and second base value calculating means for calculating the base value B(n) from the sensor output value S(n) in accordance with the following equation (3) in place of the equation (1) for a period in which the high concentration signal is generated, $$B(n)=B(n-1)+k2\{S(n)-B(n=1)\} \quad (3)$$

wherein k2 represents a second coefficient and $0 \leq k2 < k1 < 1$ is set.

First of all, the base value B(n) will be described. The base value B(n) calculated in accordance with the equation (1) or (3) is changed following a fluctuation in the sensor output value S(n) (when a coefficient k2≠0 is set). The base value B(n) has such a property that a degree of follow-up for the sensor output value S(n) is changed when the values of the coefficients k1 and k2 are varied. When the coefficients k1 and k2 are increased (approximate to 1), the base value B(n) quickly follows the sensor output value S(n). To the contrary, when the coefficients k1 and k2 are decreased (approximate to 0), the base value B(n) is changed slowly and slowly follows the sensor output value S(n). In the case of the coefficient k2=0, the base value B(n) becomes constant and does not follow the sensor output value S(n). Accordingly, in the case in which the coefficient k2 is low or k2=0 is set, the base value B(n) is greatly influenced by the past sensor output value S(n) and base value B(n).

The gas detecting device according to the invention has the first and second base value calculating means for calculating the base value B(n) having such a property in addition to the sensor resistance value converting circuit and the A/D converting means, and calculates the base value while switching the two calculating means in the middle. Since the first base value calculating means uses the comparatively great first coefficient k1 (k1>k2), the base value B(n) follows the sensor output value S(n) comparatively rapidly with a slight delay. Accordingly, while the base value is calculated by the first base value calculating means, that is, the concentration of the specific gas is low, the change of the base value for the sensor output value is small and the difference value D(n) (=S(n)−B(n)) is not very great. In the case in which the sensor output value slowly fluctuates by the influence of an environment such as a temperature or a humidity, moreover, the base value B(n) is quickly changed with follow-up. Therefore, it is possible to suppress the influence of a drift due to a fluctuation in a temperature, a humidity or the like. When the concentration of the specific gas is increased so that the sensor output value S(n) is changed (increased) rapidly and greatly, the difference value D(n) is increased because the base value B(n) cannot sufficiently carry out the follow-up. When the value exceeds the concentration threshold, the concentration signal generating means generates a high concentration signal in place of the low concentration signal. Consequently, it is possible to generate the high concentration signal with high precision while relieving the influence of an environment such as a temperature or a humidity for a period in which the concentration is increased.

In the invention, the second base value calculating means is used for calculating the base value B(n) together with the generation of the high concentration signal. Since the second coefficient k2 to be used in the second base value calculating means is comparatively small ($0 \leq k2 < k1$ the base value B(n) is changed slowly and follows the sensor output value comparatively slowly. Alternatively, the base value B(n) is not changed (when k2=0 is set). The base value calculated by using the second coefficient k2 which is comparatively small is influenced by the past sensor output values and base values, more specifically, is influenced by the base value calculated in accordance with the equation (1) immediately before the calculating equation for the base value B(n) is switched from the equation (1) to the equation (3), and is therefore influenced by the sensor output value and the base value which are obtained before the switching as described above. Typically, in the case in which k2=0 is set, the foregoing can be easily understood from the fact that the base value B(n) maintains a base value obtained immediately before the switching. In other words, the base value B(n) calculated by the second base value calculating means slowly follows the sensor output value S(n), that is, gradually approximates to the sensor output value S(n) or maintains to be constant, thereby reflecting or maintaining a state obtained immediately before the concentration of the specific gas is increased.

Accordingly, a value represented by the difference value D(n) to be a difference between the current sensor output value S(n) and the base value B(n) calculated by the second base value calculating means is obtained by comparing a present time, that is, a state in which the concentration of the specific gas is increased with a past time, that is, a state obtained before the concentration is increased. Consequently, when the concentration of the specific gas is reduced again so that the sensor output value S(n) is decreased, it is possible to easily decide that the concentration of the specific gas is reduced based on the difference value D(n) from the base value B(n). More specifically, the low concentration signal is generated in place of the high concentration signal by the concentration signal generating means. In addition, since the follow-up of the base value B(n) can be regulated to be quick or slow based on the coefficient k2, it is possible to grasp a proper period in which the concentration is reduced.

Furthermore, the base value B(n) is calculated by the first base value calculating means using the first coefficient k1 in place of the second base value calculating means synchronously with the generation of the low concentration signal in place of the high concentration signal. Consequently, the base value B(n) follows the sensor output value S(n) comparatively quickly again. Therefore, even if the concentration of the specific gas is then increased again, the increase in the concentration can be detected rapidly and reliably. According to the invention, thus, the two different coefficients k1 and k2 are used and the calculating methods of the equations (1) and (3) which are different from each other are utilized in order to calculate the base value B(n). Consequently, it is possible to set the conditions of gas detection suitable for the periods in which the concentration is increased and decreased by regulating the coefficients k1 and k2, respectively. It is preferable that the first coefficient k1 and the second coefficient k2 should be properly selected in consideration of a sampling cycle in the A/D converting means, a fluctuation range of the sensor output value S(n) and the like.

As a further solution, there is provided a gas detecting device using a gas sensor element changing a sensor resistance depending on a concentration of a converting circuit for outputting a sensor output potential depending on a change in a sensor resistance value by conducting to the gas sensor element, the sensor output potential being raised when the concentration of the specific gas is increased, A/D converting means for A/D converting the sensor output potential every predetermined time, thereby acquiring a sensor output value, first base value calculating means for calculating a base value from the sensor output value in accordance with the following equation (1), $$B(n)=B(n-1)+k1\{S(n)-B(n-1)\} \qquad (1)$$

wherein S(n) represents a sensor output value, B(n) represents a base value, k1 represents a first coefficient, $0<k1<1$ is set, and n is an integer indicative of an order of time series, difference value calculating means for calculating a difference value from the sensor output value and the base value in accordance with the following equation (2), $$D(n)=S(n)-B(n) \quad (2)$$

wherein D(n) represents a difference value, concentration level signal switching generating means for switching and generating a plurality of concentration level signals corresponding to a plurality of concentration levels, respectively, the concentration level signal switching generating means having a plurality of interlevel thresholds which correspond to level boundaries between a plurality of concentration levels with one to one and are increased corresponding to higher concentration interlevel boundaries, generating the concentration level signal corresponding to a higher concentration level than a current concentration level when the difference value is greater than the interlevel threshold corresponding to the interlevel boundary between the current concentration level and the concentration level which is higher than the current concentration level by one rank, and generating the concentration level signal corresponding to a lower concentration level than a current concentration level when the difference value is smaller than the interlevel threshold corresponding to the interlevel boundary between the current concentration level and the concentration level which is lower than the current concentration level by one rank, and second base value calculating means for calculating a base value from the sensor output value in accordance with the following equation (3) in place of the equation (1) for a period in which a concentration level signal corresponding to a higher concentration level than a predetermined concentration level is generated by the concentration $$B(n)=B(n-1)+k2\{S(n)-B(n-1)\} \quad (3)$$

wherein k2 represents a second coefficient and $0 \leq k2 < k1 < 1$ is set.

The gas detecting device according to the invention also has the first and second base value calculating means for calculating the base value B(n) in addition to the sensor resistance value converting circuit and the A/D converting means, and calculates the base value while switching the two calculating means in the middle. Since the first base value calculating means uses the first coefficient k1, the base value B(n) follows the sensor output value S(n) comparatively rapidly with a slight delay. Accordingly, while the base value is calculated by the first base value calculating means, that is, the concentration of the specific gas is low, the change of the base value for the sensor output value is small and the difference value D(n) (=S(n)−B(n)) is not very great. In the case in which the sensor output value slowly fluctuates by the influence of an environment such as a temperature or a humidity, moreover, the base value B(n) is quickly changed with follow-up. Therefore, it is possible to suppress the influence of a drift due to a fluctuation in a temperature, a humidity or the like. When the concentration of the specific gas is increased so that the sensor output value b(n) is changed (increased) rapidly and greatly, the difference value D(n) is increased because the base value B(n) cannot sufficiently carry out the follow-up. However, when the concentration of the specific gas is increased so that the sensor output value S(n) is changed greatly, the difference value D(n) is increased because the base value B(n) cannot sufficiently carry out the follow-up. When the difference value D(n) exceeds some of the interlevel thresholds, a concentration level signal corresponding to a higher concentration level than the concentration level corresponding to the currently generated concentration level signal is generated.

In other words, the rank of the concentration level signal is increased. For the period in which a concentration level signal corresponding to a higher concentration level than a predetermined concentration level is generated, moreover, the second base value calculating means is used for calculating the base value B(n).

On the other hand, since the second coefficient k2 to be used in the second base value calculating means is comparatively small ($0 \leq k2 < k1$), the base value B(n) is changed slowly and follows the sensor output value comparatively slowly. Alternatively, the base value B(n) is not changed (when k2=0 is set). The base value B(n) calculated by using the comparatively small second coefficient k2 is influenced by the past sensor output values and base values, more specifically, is influenced by the base value calculated in accordance with the equation (1) immediately before the calculating equation for the base value B(n) is switched from the equation (1) to the equation (3), and is therefore influenced by the sensor output value and the base value which are obtained before the switching as described above. In other words, the base value B(n) calculated by the second base value calculating means slowly follows the sensor output value S(n), that is, gradually approximates to the sensor output value S(n) or maintains to be constant, thereby reflecting or maintaining a state obtained immediately before the concentration of the specific gas is increased. By using the difference value D(n) to be a difference between the base value B(n) calculated by the second base value calculating means and the current sensor output value S(n), accordingly, the current level of the concentration of the specific gas can be decided by setting, as a reference, a concentration obtained in the past, more specifically, when the calculating equation for the base value B(n) is switched from the equation (1) to the equation (3).

In the case in which a different concentration level from the concentration level corresponding to the currently generated concentration level signal is decided by the fluctuation in the difference value D(n), switching to the concentration level signal is carried out. In other words, also when the concentration of the specific gas is reduced or increased so that the sensor output value S(n) is decreased or increased, it is possible to easily decide that the concentration of the specific gas is reduced or increased based on the difference value D(n). In addition, it is possible to regulate the follow-up of the base value B(n) to be slow or quick based on the coefficients k1 and k2. Therefore, it is possible to grasp a proper time that the concentration is increased or reduced.

For example, in the case in which the concentration of the specific gas is reduced so that the difference value D(n) corresponds to a low concentration level, a concentration level signal corresponding to a lower concentration level than the concentration level corresponding to a currently generated concentration level signal is generated. In other words, the rank of the concentration level signal is reduced. To the contrary, in the case in which the concentration of the specific gas is increased so that the difference value D(n) corresponds to a high concentration level, a concentration level signal corresponding to a higher concentration level than the concentration level corresponding to a currently generated concentration level signal is generated. In other words, the rank of the concentration level signal is increased.

In the case in which the difference value D(n) corresponds to a concentration level which is equal to or lower than a predetermined concentration level for the period in which the concentration level signal corresponding to the higher concentration level than the predetermined concentration level is generated, furthermore, the base value B(n) is calculated by the first base value calculating means again in place of the second base value calculating means. Consequently, the base value B(n) follows the sensor output value S(n) comparatively quickly again. Accordingly, even if the concentration of the specific gas is then increased again, the increase in the concentration can be detected rapidly and reliably. It is preferable that the first coefficient k1 and the second coefficient k2 should be properly selected depending on a sampling cycle in the A/D converting means, a fluctuation range of the sensor output value S(n) or the like.

In the invention, thus, the concentration level signal switching generating means switches and generates a plurality of concentration level signals corresponding to a plurality of concentration levels respectively. Therefore, it is possible to generate a concentration level signal corresponding to a finer concentration level as well as the concentration of the specific gas. Consequently, it is possible to carry out a finer control corresponding to the concentration level of the specific gas in various control systems, for example, a flap control in an autoventilation system using the gas detecting device, a fan control in a control system for an air cleaner or the like.

In the gas detecting device, furthermore, it is preferable that the predetermined concentration level in the second base value calculating means should be the lowest one of the concentration levels.

When the base value B(n) is to be calculated, a subsequent base value B(n) is calculated by using, as a reference, a concentration at a time that the concentration of the specific gas is increased to a higher concentration level from the lowest concentration level by one rank if the second base value calculating means is used for the period in which the concentration level signal corresponding to a higher concentration level than the lowest concentration level is generated as in the invention. Since the lowest concentration level can be used as the reference, consequently, the concentration of the specific gas can be compared more accurately.

In any of the gas detecting devices, furthermore, it is preferable that the second coefficient k2 should be set to k2>0.

In the gas detecting device according to the invention, the second coefficient k2 is greater than 0 (k2>0). Consequently, the base value B(n) calculated by the second base value calculating means for the period in which the high concentration signal of the specific gas is generated is not constant but is slowly changed following the sensor output value S(n). As described above, the gas sensor element is influenced by an environment such as a temperature or a humidity, a wind velocity and the like as well as a change in the concentration of the specific gas. Even if the concentration of the specific gas is constant, the sensor output value S(n) is gradually changed in some cases. If a drift is generated in such a direction that the sensor output value S(n) is increased for a period in which the concentration of the specific gas is increased and is then reduced, more specifically, a period in which the calculation of the base value B(n) is changed from the first base value calculating means to the second base value calculating means, the sensor output value S(n) is decreased to a greater value than a value obtained before the increase by the drift even if the concentration of the specific gas is reduced to the same level as that obtained before the increase. In the case in which the second coefficient k2=0 is set, the base value B(n) is not changed according to the equation (3) (B(n)=B(n−1)). Therefore, the difference value D(n) is also decreased to a greater value than the value obtained before the increase. Accordingly, there is a possibility that it might be erroneously decided that the concentration of the specific gas is high because of the great difference value D(n) even if the concentration of the specific gas is actually reduced sufficiently and a reduction in the concentration of the gas cannot be discriminated. Therefore, in the case in which the gas detecting device according to the invention is used for the autoventilation system for a vehicle or the control system for an air cleaner, a flap is maintained to be closed for a long time or a fan is rotated at a high speed so that a proper control can be carried out with difficulty.

On the other hand, in the invention, k2>0 is set. Therefore, the base value B(n) slowly follows the sensor output value S(n) so that the difference value D(n) is gradually decreased with the passage of time even if a drift is generated on the sensor output value S(n) and the concentration of the specific gas is then reduced. Accordingly, after some time passes, a low concentration signal is always generated or the concentration level is reduced to be low and a concentration level signal corresponding thereto can be generated. In the autoventilation system for a vehicle or the control system for an air cleaner, accordingly, a proper control can be carried out, for example, the flap is opened or the fan is rotated at a low speed when some time passes. Moreover, when some time passes, the base value B(n) can be always calculated by using the first base value calculating means in place of the second base value calculating means. Consequently, the base value B(n) following the sensor output value S(n) comparatively quickly is calculated again and an increase in the concentration of the specific gas can be detected.

As further solution, moreover, there is provided a gas detecting device using a gas sensor element changing a sensor resistance depending on a concentration of a specific gas, comprising a sensor resistance value converting circuit outputting a sensor output potential depending on a change in a sensor resistance value by conducting to the gas sensor element, the sensor output potential being reduced when the concentration of the specific gas is increased, A/D converting means for A/D converting the sensor output potential every predetermined time, thereby acquiring a sensor output value, third base value calculating means for calculating a base value from the sensor output value in accordance with the following equation (4), $$B(n)=B(n-1)+k3\{S(n)-B(n-1)\} \quad (4)$$

wherein S(n) represents a sensor output value, B(n) represents a base value, k3 represents a third coefficient, 0<k3<1 is set, and n is an integer indicative of an order of time series, difference value calculating means for calculating a difference value D(n) from the sensor output value S(n) and the base value B(n) in accordance with the following equation (5), $$D(n)=B(n)-S(n) \quad (5)$$

wherein D(n) represents a difference value, concentration signal generating means for generating either a low concentration signal or a high concentration signal, the concentration signal generating means generating the high concentration signal when the difference value is greater than a predetermined concentration threshold, and fourth base value calculating means for calculating the base value B(n) from the sensor output value S(n) in accordance with the following equation (6) in place of the equation (4) for a period in which the high concentration signal is generated, $$B(n)=B(n-1)+k4\{S(n)-B(n-1)\} \quad (6)$$

wherein k4 represents a fourth coefficient and $0 \leq k4 < k3 < 1$ is set.

The gas detecting device according to the invention has the third and fourth base value calculating means for calculating the base value B(n) having such a property in addition to the sensor resistance value converting circuit and the A/D converting means, and calculates the base value while switching the two calculating means in the middle. Since the third base value calculating means uses the comparatively great third coefficient k3 (k3>k4), the base value B(n) follows the sensor output value S(n) comparatively rapidly with a slight delay. Accordingly, while the base value is calculated by the third base value calculating means, that is, the concentration of the specific gas is low, the change of the base value for the sensor output value is small and the difference value D(n) (=B(n)−S(n)) is not very great. In the case in which the sensor output value slowly fluctuates by the influence of an environment such as a temperature or a humidity, moreover, the base value B(n) is quickly changed with follow-up. Therefore, it is possible to suppress the influence of a drift due to a fluctuation in a temperature, a humidity or the like. When the concentration of the specific gas is increased so that the sensor output value S(n) is changed (decreased) rapidly and greatly, the difference value D(n) is increased because the base value B(n) cannot sufficiently carry out the follow-up. When the value exceeds the concentration threshold, the concentration signal generating means generates a high concentration signal in place of the low concentration signal. Consequently, it is possible to generate the high concentration signal with high precision while relieving the influence of an environment such as a temperature or a humidity for a period in which the concentration is increased.

In the invention, the fourth base value calculating means is used for calculating the base value B(n) together with the generation of the high concentration signal. Since the fourth coefficient k4 to be used in the fourth base value calculating means is comparatively small ($0 \leq k4 < k3$), the base value B(n) is changed slowly and follows the sensor output value comparatively slowly. Alternatively, the base value B(n) is not changed (when k4=0 is set). The base value calculated by using the comparatively small fourth coefficient k4 is influenced by the past sensor output values and base values, more specifically, is influenced by the base value calculated in accordance with the equation (4) immediately before the calculating equation for the base value B(n) is switched from the equation (4) to the equation (6), and is therefore influenced by the sensor output value and the base value which are obtained before the switching as described above. Typically, in the case in which k4=0 is set, the foregoing can be easily understood from the fact that the base value B(n) maintains a base value obtained immediately before the switching. In other words, the base value B(n) calculated by the fourth base value calculating means slowly follows the sensor output value S(n), that is, gradually approximates to the sensor output value S(n) or maintains to be constant, thereby reflecting or maintaining a state obtained immediately before the concentration of the specific gas is increased.

Accordingly, a value represented by the difference value D(n) to be a difference between the current sensor output value S(n) and the base value B(n) calculated by the fourth base value calculating means is obtained by comparing a present time, that is, a state in which the concentration of the specific gas is increased with a past time, that is, a state obtained before the concentration is increased. Consequently, when the concentration of the specific gas is reduced again so that the sensor output value S(n) is increased, it is possible to easily decide that the concentration of the D(n) from the base value B(n). More specifically, the low concentration signal is generated in place of the high concentration signal by the concentration signal generating means.

Furthermore, the base value B(n) is calculated by the third base value calculating means using the third coefficient k3 in place of the fourth base value calculating means synchronously with the generation of the low concentration signal in place of the high concentration signal. Consequently, the base value B(n) follows the sensor output value S(n) comparatively quickly again. Therefore, even if the concentration of the specific gas is then increased again, the increase in the concentration can be detected rapidly and reliably.

It is preferable that the third coefficient k3 and the fourth coefficient k4 should be properly selected depending on a sampling cycle in the A/D converting means, a fluctuation range of the sensor output value S(n) or the like.

As further solution, there is provided a gas detecting device using a gas sensor element changing a sensor resistance depending on a concentration of a specific gas, comprising a sensor resistance value converting circuit outputting a sensor output potential depending on a change in a sensor resistance value by conducting to the gas sensor element, the sensor output potential being reduced when the concentration of the specific gas is increased, A/D converting means for A/D converting the sensor output potential every predetermined time, thereby acquiring a sensor output value, third base value calculating means for calculating a base value from the sensor output value in accordance with the following equation (4), $$B(n)=B(n-1)+k3\{S(n)-B(n-1)\} \quad (4)$$

wherein S(n) represents a sensor output value, B(n) represents a base value, k3 represents a third coefficient, $0<k3<1$ is set, and n is an integer indicative of an order of time series, difference value calculating means for calculating a difference value from the sensor output value and the base value in accordance with the following equation (5), $$D(n)=B(n)-S(n) \quad (5)$$

wherein D(n) represents a difference value, concentration level signal switching generating means for switching and generating a plurality of concentration level signals corresponding to a plurality of concentration levels, respectively, the concentration level signal switching generating means having a plurality of interlevel thresholds which correspond to level boundaries between a plurality of concentration levels with one to one and are increased corresponding to higher concentration interlevel boundaries, generating the concentration level signal corresponding to a higher concentration level than a current concentration level when the difference value is greater than the interlevel threshold corresponding to the interlevel boundary between the current concentration level and the concentration level which is higher than the current concentration level by one rank, and generating the concentration level signal corresponding to a lower concentration level than a current concentration level when the difference value is smaller than the interlevel threshold corresponding to the interlevel boundary between the current concentration level and the concentration level which is lower than the current concentration level by one rank, and fourth base value calculating means for calculating a base value from the sensor output value in accordance with the following equation (6) in place of the equation (4) for a period in which a concentration level signal corresponding to a higher concentration level than a predetermined concentration level is generated by the concentration level signal switching generating means, $$B(n)=B(n-1)+k4\{S(n)-B(n-1)\} \quad (6)$$

wherein k4 represents a fourth coefficient and $0 \leq k4 < k3 < 1$ is set.

The gas detecting device according to the invention also has the third and fourth base value calculating means for calculating the base value B(n) in addition to the sensor resistance value converting circuit and the A/D converting means, and calculates the base value while switching the two calculating means in the middle. Since the third base value calculating means uses the comparatively great third coefficient k3 (k3>k4), the base value B(n) follows the sensor output value S(n) comparatively rapidly with a slight delay. Accordingly, while the base value is calculated by the third base value calculating means, that is, the concentration of the specific gas is low, the change of the base value for the sensor output value is small and the difference value D(n) (=B(n)−S(n)) is not very great. However, when the concentration of the specific gas is increased so that the sensor output value S(n) is greatly changed (decreased), the difference value D(n) is increased because the base value B(n) cannot sufficiently carry out the follow-up. When the difference value D(n) exceeds some of the interlevel thresholds, a concentration level signal corresponding to a higher concentration level than the concentration level corresponding to the current concentration level, that is, the currently generated concentration level signal is generated. In other words, the rank of the concentration level signal is increased. For the period in which a concentration level signal corresponding to a higher concentration level than a predetermined concentration level is generated, moreover, the fourth base value calculating means is used for calculating the base value B(n).

Since the fourth coefficient k4 to be used in the fourth base value calculating means is comparatively small (0≦k4<k3), the base value B(n) is changed slowly and follows the sensor output value comparatively slowly. Alternatively, the base value B(n) is not changed (when k4=0 is set). The base value B(n) calculated by using the comparatively small fourth coefficient k4 is influenced by the past sensor output values and base values, more specifically, is influenced by the base value calculated in accordance with the equation (4) immediately before the calculating equation for the base value B(n) is switched from the equation (4) to the equation (6), and is therefore influenced by the sensor output value and the base value which are obtained before the switching as described above. In other words, the base value B(n) calculated by the fourth base value calculating means slowly follows the sensor output value S(n), that is, gradually approximates to the sensor output value S(n) or maintains to be constant, thereby reflecting or maintaining a state obtained immediately before the concentration of the specific gas is increased. By using the difference value D(n) to be a difference between the base value B(n) calculated by the fourth base value calculating means and the current sensor output value S(n), accordingly, the current level of the concentration of the specific gas can be decided by setting, as a reference, a concentration obtained in the past, more specifically, when the calculating equation for the base value B(n) is switched from the equation (4) to the equation (6).

In the case in which a different concentration level from the concentration level corresponding to the currently generated concentration level signal is decided by the fluctuation in the difference value D(n), switching to the concentration level signal is carried out. In other words, also when the concentration of the specific gas is reduced or increased so that the sensor output value S(n) is decreased or increased, it is possible to easily decide that the concentration of the specific gas is reduced or increased based on the difference value D(n). For example, in the case in which the concentration of the specific gas is reduced so that the difference value D(n) corresponds to a low concentration level, a concentration level signal corresponding to a lower concentration level than the concentration level corresponding to a currently generated concentration level signal is generated. In other words, the rank of the concentration level signal is reduced. To the contrary, in the case in which the concentration of the specific gas is increased so that the difference value D(n) corresponds to a high concentration level, a concentration level signal corresponding to a higher concentration level than the concentration level corresponding to a currently generated concentration level signal is generated. In other words, the rank of the concentration level signal is increased.

In the case in which the difference value D(n) corresponds to a concentration level which is equal to or lower than a predetermined concentration level for the period in which the concentration level signal corresponding to the higher concentration level than the predetermined concentration level is generated, furthermore, the base value B(n) is calculated by the third base value calculating means again in place of the fourth base value calculating means. Consequently, the base value B(n) follows the sensor output value S(n) comparatively quickly again. Accordingly, even if the concentration of the specific gas is then increased again, the increase in the concentration can be detected rapidly and reliably. It is preferable that the third coefficient k3 and the fourth coefficient k4 should be properly selected depending on a sampling cycle in the A/D converting means, a fluctuation range of the sensor output value S(n) or the like.

In the gas detecting device according to the invention, the concentration level signal switching generating means switches and generates a plurality of concentration level signals corresponding to a plurality of concentration levels respectively. Therefore, it is possible to generate a concentration level signal corresponding to a finer concentration level as well as the concentration of the specific gas.

In any of the gas detecting devices, furthermore, it is preferable that the predetermined concentration level in the fourth base value calculating means should be the lowest one of the concentration levels.

When the base value B(n) is to be calculated, a subsequent base value B(n) is calculated by using, as a reference, a concentration at a time that the concentration of the specific gas is increased to a higher concentration level from the lowest concentration level by one rank if the fourth base value calculating means is used for the period in which the concentration level signal corresponding to a higher concentration level than the lowest concentration level is generated as in the invention. Since the lowest concentration level can be used as the reference, consequently, the concentration of the specific gas can be compared more accurately.

In any of the gas detecting devices, furthermore, it is preferable that the fourth coefficient k4 should be set to k4>0.

In the gas detecting device according to the invention, the fourth coefficient k4 is greater than 0 (k4>0). Consequently, the base value B(n) calculated by the fourth base value calculating means for the period in which the high concentration signal of the specific gas is generated is not constant but is slowly changed following the sensor output value S(n). As described above, the gas sensor element is influenced by an environment such as a temperature or a humidity, a wind velocity and the like as well as a change in the concentration of the specific gas. Even if the concentration of the specific gas is constant, the sensor output value S(n) is gradually changed in some cases. If a drift is generated in such a direction that the sensor output value S(n) is decreased for a period in which the concentration of the specific gas is increased and is then reduced, more specifically, a period in which the calculation of the base value B(n) is changed from the third base value calculating means to the fourth base value calculating means, the sensor output value S(n) is increased to a smaller value than a value obtained before the increase by the drift even if the concentration of the specific gas is increased to the same level as that obtained before the increase. In the case in which the fourth coefficient k4=0 is set, the base value B(n) is not changed according to the equation (6) (B(n)=B(n−1)). Therefore, the difference value D(n) is reduced to a greater value than the value obtained before the increase in the concentration of the gas. Accordingly, there is a possibility that it might be erroneously decided that the concentration of the specific gas is high because of the great difference value D(n) even if the concentration of the specific gas is actually reduced sufficiently and a reduction in the concentration of the gas cannot be discriminated. Therefore, in the case in which the gas detecting device according to the invention is used for the autoventilation system for a vehicle or the control system for an air cleaner, a flap is maintained to be closed for a long time or a fan is rotated at a high speed so that a proper control can be carried out On the other hand, in the invention, k4>0 is set. Therefore, the base value B(n) slowly follows the sensor output value S(n) so that the difference value D(n) is gradually decreased with the passage of time even if a drift is generated on the sensor output value S(n) and the concentration of the specific gas is then reduced. Accordingly, after some time passes, a low concentration signal is always generated or the concentration level is reduced to be low and a concentration level signal corresponding thereto can be generated. In the autoventilation system for a vehicle or the control system for an air cleaner, accordingly, a proper control can be carried out, for example, the flap is opened or the fan is rotated at a low speed when some time passes. Moreover, when some time passes, the base value B(n) can be always calculated by using the third base value calculating means in place of the fourth base value calculating means. Consequently, the base value B(n) following the sensor output value S(n) comparatively quickly is calculated again and an increase in the concentration of the specific gas can be detected.

As further means, moreover, there is provided a gas detecting device using a gas sensor element changing a sensor resistance depending on a concentration of a specific gas, comprising a sensor resistance value converting circuit for outputting a sensor output potential depending on a change in a sensor resistance value by conducting the gas sensor element, the sensor output potential being raised when the concentration of the specific gas is increased, A/D converting means for A/D converting the sensor output potential every predetermined time, thereby acquiring a sensor output value, differential value calculating means for calculating a differential value from the sensor output value in accordance with the following equation (7), $$V(n)=S(n)-S(n-1) \qquad (7)$$

wherein S(n) represents a sensor output value, V(n) represents a differential value, and n is an integer indicative of an order of time series, base value calculating means for calculating a base value B(n) from the sensor output value S(n) in accordance with the following equation (8), $$B(n)=B(n-1)+k\{S(n)-B(n-1)\} \qquad (8)$$

wherein k represents a coefficient and 0<k<1 is set, difference value calculating means for calculating a difference value D(n) from the sensor output value S(n) and the base value B(n) in accordance with the following equation (9), and $$D(n)=S(n)-B(n) \qquad (9)$$

concentration signal generating means for generating either a low concentration signal or a high concentration signal, the concentration signal generating means generating the high concentration signal when the differential value V(n) is greater than a first threshold for a period in which the low concentration signal is generated and generating the low concentration signal when the difference value D(n) is smaller than a second threshold for a period in which the high concentration signal is generated.

The differential value V(n) obtained by the equation (7) represents a difference between the sensor output value S(n) and the last value S(n−1), that is, the amount of change. Accordingly, when the sensor output value is greatly increased, for example, the differential value V(n) immediately becomes great. When utilizing the sensor resistance value converting circuit having such a characteristic that the sensor output potential is increased when the concentration of the gas is raised, therefore, the differential value V(n) is used and the differential value V(n) is compared with the first threshold set optionally in consideration of a fluctuation in the sensor output value by the influence of an environment such as a temperature or a humidity. Consequently, it is possible to grasp an increase in the concentration in the early stage of the increase in the concentration of the gas while relieving the influence of the environment such as a temperature or a humidity. On the other hand, the base value B(n) has such a property as to be changed following the fluctuation in the sensor output value S(n) as described above.

The gas detecting device according to the invention comprises the differential value calculating means for calculating the differential value V(n) having such a property, base value calculating means for calculating the base value B(n) and the difference value calculating means in addition to the sensor resistance value converting circuit and the A/D converting means, and switches and generates a low concentration signal and a high concentration signal. More specifically, when the differential value is greater than the first threshold for the period in which the low concentration signal is generated, the high concentration signal is generated.

On the other hand, when the difference value D(n) is smaller than the second threshold for the period in which the high concentration signal is generated, the low concentration signal is generated. The base value B(n) follows the sensor output value S(n) with a slight delay. Accordingly, even if a drift is generated in such a direction that the sensor output values (n) is increased, the difference value D(n) is gradually decreased with the passage of time. Consequently, the difference value D(n) finally becomes smaller than the second threshold so that the low concentration signal can always be generated. In the case in which the concentration of the gas is thus reduced, the reduction in the concentration of the gas can be detected based on the difference value D(n) calculated by using the sensor output S(n) and the base value B(n). In addition, it is possible to regulate the follow-up of the base value B(n) for the sensor output value S(n) to be slow or quick based on the coefficient k for calculating the base value B(n).

As further means, there is provided a gas detecting device using a gas sensor element changing a sensor resistance depending on a concentration of a specific gas, comprising a sensor resistance value converting circuit for outputting a sensor output potential depending on a change in a sensor resistance value by conducting to the gas sensor element, the sensor output potential being reduced when the concentration of the specific gas is increased, A/D converting means for A/D converting the sensor output potential every predetermined time, thereby acquiring a sensor output value, differential value calculating means for calculating a differential value from the sensor output value in accordance with the following equation (10), $$V(n)=S(n-1)-S(n) \qquad (10)$$

wherein S(n) represents a sensor output value, V(n) represents a differential value, and n is an integer indicative of an order of time series, base value calculating means for calculating a base value B(n) from the sensor output value S(n) in accordance with the following equation (11), $$B(n)=B(n-1)+k\{S(n)-B(n-1)\} \qquad (11)$$

wherein k represents a coefficient and 0<k<1 is set, difference value calculating means for calculating a difference value D(n) from the sensor output value S(n) and the base value B(n) in accordance with the following equation (12), and $$D(n)=B(n)-S(n) \qquad (12)$$

concentration signal generating means for generating either a low concentration signal or a high concentration signal, the concentration signal generating means generating the high concentration signal when the differential value V(n) is greater than a first threshold for a period in which the low concentration signal is generated and generating the low concentration signal when the difference value D(n) is smaller than a second threshold for a period in which the high concentration signal is generated.

The differential value V(n) obtained by the equation (10) represents a difference between the last sensor output value S(n−1) and the current sensor output value S(n), that is, the amount of change. The value has an inverted sign from that of the equation (7). Accordingly, when the sensor output value is greatly increased, for example, the differential value V(n) immediately becomes great. When utilizing the sensor resistance value converting circuit having such a characteristic that the sensor output potential is reduced when the concentration of the gas is increased, therefore, the differential value V(n) is used and the differential value V(n) is compared with the first threshold set optionally in consideration of a fluctuation in the sensor output value by the influence of an environment such as a temperature or a humidity. Consequently, it is possible to grasp an increase in the concentration in the early stage of the increase in the concentration of the gas while relieving the influence of the environment such as a temperature or a humidity. On the other hand, the base value B(n) has such a property as to be changed following the fluctuation in the sensor output value S(n) as described above. Moreover, the difference value D(n) calculated by the equation (12) is obtained by subtracting the sensor output value from the base value reversely to the equation (9).

The gas detecting device according to the invention comprises the differential value calculating means for calculating the differential value V(n) having such a property, base value calculating means for calculating the base value B(n), and the difference value calculating means in addition to the sensor resistance value converting circuit and the A/D converting means, and switches and generates a low concentration signal and a high concentration signal. More specifically, when the differential value is greater than the first threshold for the period in which the low concentration signal is generated, the high concentration signal is generated. By using the differential value V(n) as described above, it is possible to grasp an increase in the concentration in the early stage of the increase in the concentration of the gas while relieving the influence of the environment such as a temperature or a humidity.

On the other hand, when the difference value D(n) is smaller than the second threshold for the period in which the high concentration signal is generated, the low concentration signal is generated. The base value B(n) follows the sensor output value S(n) with a slight delay. Accordingly, in the case in which the concentration of the gas is reduced as described above, the reduction in the concentration of the gas can be detected based on the difference value D(n) calculated by using the sensor output S(n) and the base value B(n) In addition, it is possible to regulate the follow-up of the base value B(n) for the sensor output value S(n) to be slow or quick based on the coefficient k for calculating the base value B(n).

Figure 1:
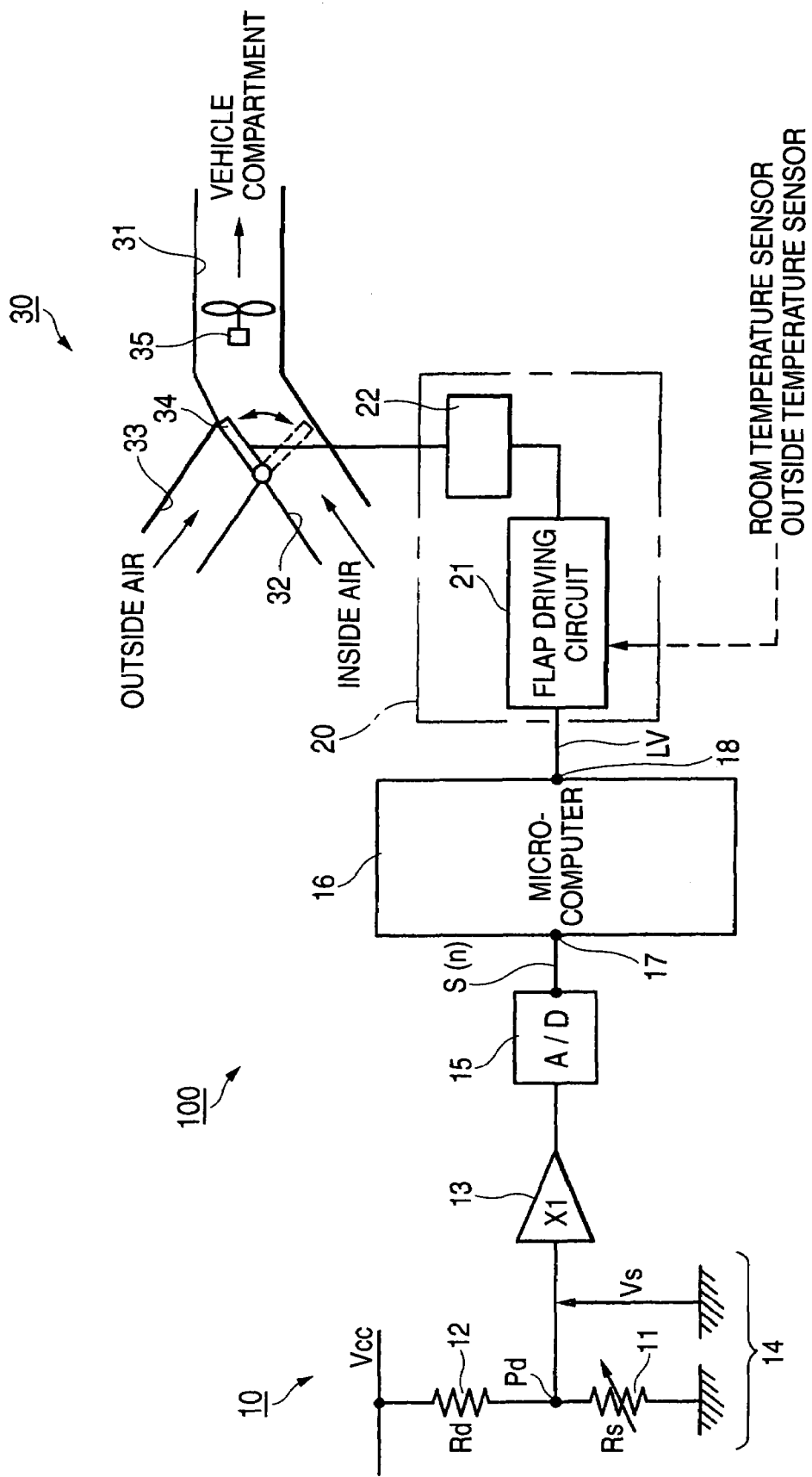
FIG. 1 is a diagram illustrating the summary of a gas detecting device and an autoventilation system for a vehicle according to a first embodiment.

In the drawings, the reference numerals 100, 140, 150 and 160 denote an autoventilation system for a vehicle, the reference numerals 10, 40, 50 and 60 denote a gas detecting device, the reference numerals 11, 41, 57 and 67 denote a gas sensor element, the reference numeral 12 denotes a detecting resistor, the reference numerals, 14, 44, 51 and 61 denote a sensor resistance value converting circuit, the reference numeral 16 denotes a microcomputer (μC), the reference numeral 20 denotes an electronic control assembly, the reference numeral 21 denotes a flap driving circuit, and the reference numeral 34 denotes a flap.

BEST MODE FOR CARRYING OUT THE INVENTION

First Embodiment

A first embodiment of the invention will be described with reference to FIGS. 1 to 5. FIG. 1 is a circuit diagram and a block diagram showing a gas detecting device 10 according to the first embodiment and illustrates the schematic structure of an autoventilation system 100 for a vehicle including the gas detecting device 10.

First of all, the gas detecting device 10 will be described. The gas detecting device 10 uses a gas sensor element 11 comprising an oxide semiconductor of such a type that the concentration of an oxidizing gas component such as NOx is increased and a sensor resistance value RS is increased by a reaction to a specific gas if the oxidizing gas component is present in a measured gas (an atmosphere in the embodiment). The gas sensor element 11 is provided on the outside of the compartment of an automobile.

By using the gas sensor element 11, a sensor output value S(n) is acquired by acquiring means including a sensor resistance value converting circuit 14, a buffer 13 and an A/D converting circuit 15. More specifically, the sensor resistance value converting circuit 14 outputs a sensor output potential Vs corresponding to the sensor resistance value Rs of the gas sensor element 11. More specifically, a sensor output potential Vs on an operation point Pd which is obtained by dividing a supply voltage Vcc by the gas sensor element 11 and a resistor 12 having a detection resistance value Rd is output through the buffer 13. For this reason, the sensor resistance value converting circuit 14 is constituted such that the sensor resistance value Rs is increased and the sensor output potential Vs is raised when the concentration of the oxidizing gas such as NOx is increased. The output of the buffer 13 (the sensor output potential Vs) is input to the A/D converting circuit 15, and is output as the sensor output value S(n) digitally converted in each predetermined sample cycle (0.25 second in the embodiment) and is input to an input terminal 17 of a microcomputer (hereinafter referred to as a "μC") 16. n is a serial integer representing an order.

Furthermore, a concentration signal LV to be any of a high concentration signal and a low concentration signal for controlling an electronic control assembly 20 is output from an output terminal 18 of the μC 16. The electronic control assembly 20 serves to control a flap 34 of a ventilation system 30 in an automobile for controlling the circulation of inside air and the intake of outside air in an automobile. More specifically in the embodiment, the ventilation system 30 serves to control the flap 34 for switching a duct 32 for inside air intake to take in and circulate the inside air and a duct 33 for outside air intake to take in outside air which are connected like a fork to a duct 31 communicating with the inside of the compartment of the automobile. A flap driving circuit 21 in the electronic control assembly 20 operates an actuator 22 to rotate the flap 34 and to connect either the duct 32 for inside air intake or the duct 33 for outside air intake to the duct 31 in response to a concentration signal LV sent from the output terminal 18 of the μC 16, in the embodiment, the concentration signal LV indicating whether the concentration of the oxidizing gas component such as NOx is increased or decreased.

Figure 2:
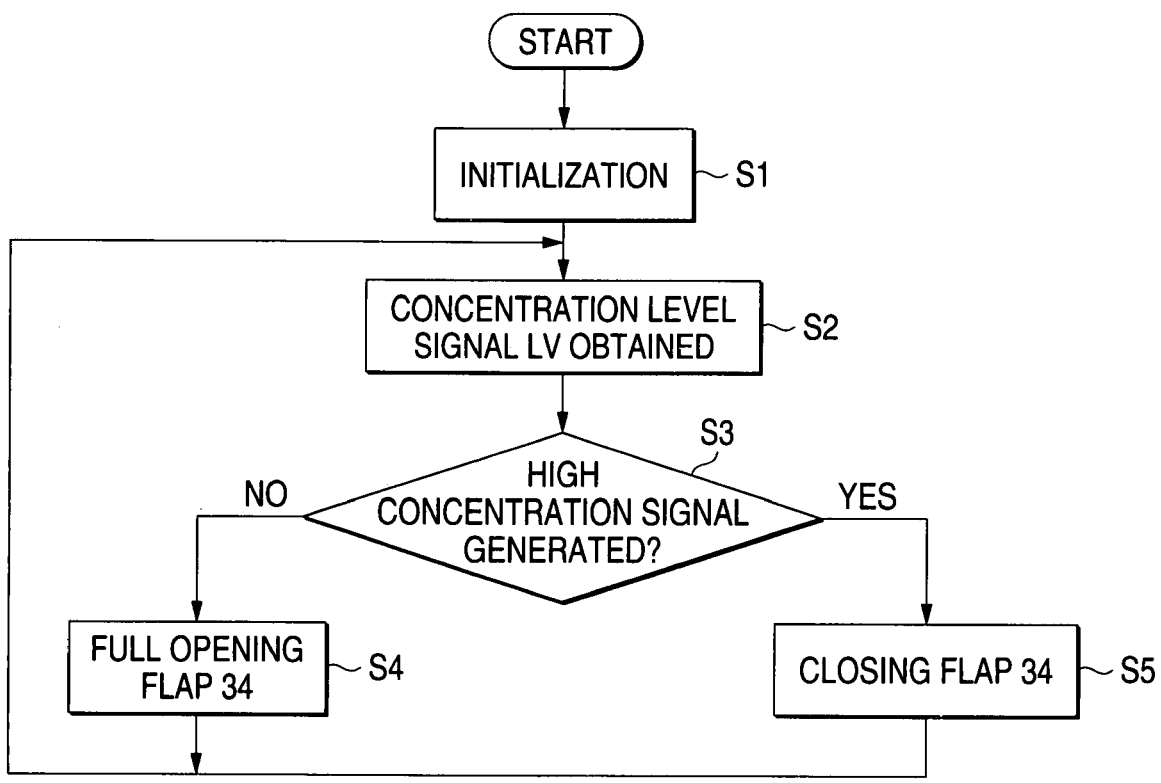
FIG. 2 is a flow chart showing a control in the autoventilation system for a vehicle according to the first embodiment.

For example, as shown in a flow chart of FIG. 2, initialization is carried out at Step S1 and a concentration level signal LV is then acquired at Step S2, and it is decided whether or not the concentration signal LV is a high concentration signal, that is, whether or not the high concentration signal is being generated at Step S3. If the decision is No, that is, a low concentration signal is being generated, the concentration of a specific gas is low. At Step S4, therefore, an instruction for fully opening the flap 34 is given. Consequently, the flap 34 is rotated so that the duct 33 for outside air intake is connected to the duct 31 and the outside air is taken into a vehicle compartment. On the other hand, the decision is yes, that is, the high concentration signal is being generated at the Step S3, the concentration of the specific gas is high on the outside of the vehicle compartment. At Step S5, therefore, an instruction for fully closing the flap 34 is given. Consequently, the flap 34 is rotated and the duct 32 for inside air intake is connected to the duct 31 so that outside air introduction is blocked and inside air circulation is carried out.

A fan 35 for pressure feeding of air is provided in the duct 31. The flap driving circuit 21 may switch the flap 34 in response to only the concentration signal LV. For example, the μC or the like may be used to switch the flap 34 in consideration of information sent from a room temperature sensor, a humidity sensor, an outside temperature sensor or the like as shown in a broken line of the drawing in addition to the concentration signal LV sent from the gas detecting device 10.

In the μC 16, the sensor output value S(n) input from the input terminal 17 is subjected to a processing according to a flow which will be described below, thereby detecting a change in the concentration of the oxidizing gas component based on the sensor resistance value Rs of the gas sensor element 11, a change thereof or the like. The μC 16 has a well-known structure and includes a microprocessor for carrying out an operation, a RAM for temporarily storing a program or data, a ROM for holding a program or data and the like, which will not be shown in detail. Moreover, the μC 16 including the A/D converting circuit 15 can also be used.

Next, a control in the μC 16 will be described in accordance with a flow chart of FIG. 3. When the engine of the automobile is driven, the control system is activated. The gas sensor element 11 is waited to be brought into an active state and initialization is first carried out at Step S11. For the initialization, an original sensor output value S(0) at which the gas sensor element 11 is set in the active state is stored as a base value B(0) (B(0)=S(0)). Moreover, the low concentration signal is generated as the concentration signal LV, more specifically, the concentration signal LV is set to have a low level. Then, the processing proceeds to Step S12 where the sensor output value S(n) obtained by A/D converting a sensor signal, that is, the sensor output potential Vs every 0.25 second is sequentially read. At Step S13, next, it is decided whether or not a high concentration signal indicating that the concentration signal LV has a high level at the present time, that is, the concentration of the specific gas (the oxidizing gas in the embodiment) has the high level is generated. If the decision is No, that is, the concentration of the specific gas is low, the concentration signal LV has the low level and the low concentration signal is generated, the processing proceeds to Step S14. On the other hand, if the decision is Yes, that is, the concentration of the specific gas is high, the concentration signal LV has the high level and the high concentration signal is generated, the processing proceeds to Step S15.

At the Step S14, a base value B(n) is calculated in accordance with the following equation by utilizing a last base value B(n−1) and the sensor output value S(n) and the processing proceeds to Step S16. B(n) B(n−1)+k1{S(n)−B(n−1)}, wherein a first coefficient k1 is set to 0<k1<1. On the other hand, at the Step S15, the base value B(n) is calculated in accordance with the following equation by utilizing the last base value B(n−1) and the sensor output value S(n) and the processing proceeds to the Step S16. B(n)=B(n−1)+k2{S(n)−B(n−1)}, wherein a second coefficient k2 is set to 0≦k2<k1<1. As described above, the base value B(n) has the degree of follow-up for the sensor output value S(n) varied depending on the coefficients k1 and k2 to be used, and the base value B(n) follows the sensor output value S(n) comparatively sensitively with a slight delay if the comparatively great first coefficient (k1>k2) is used (Step S14). On the other hand, if the comparatively small second coefficient k2(k2<k1) is used (Step S15), the base value B(n) is changed slowly and the follow-up is carried out slowly.

Accordingly, when the calculating equation is switched to calculate the base value by using the second coefficient k2 through the Step S15 in place of the Step S14, the base value B(n) thus calculated is not greatly varied from the base value B(n−1) obtained immediately before the switching even if the sensor output value S(n) is greatly varied. Since the base value B(n−1) obtained immediately before the switching is calculated by using the first coefficient k1 at the Step S14, it follows the sensor output value S(n−1) obtained before the switching. Accordingly, the base value B(n) calculated at the Step S15 reflects the influence of a state obtained in the past, that is, immediately before the switching. To the contrary, when the calculating equation of the base value is switched to calculate the base value by using the first coefficient k1 through the Step S14 in place of the Step S15, the base value B(n) rapidly follows a current sensor output value S(n) so that it is less influenced by the base value and the sensor output value which are obtained immediately before the switching.

A difference value D(n) is calculated in accordance with an equation of D(n)=S(n)−B(n) at the Step S16 and is compared with a concentration threshold T at Step S17. If D(n)>T (yes) is obtained, the processing proceeds to Step S18. If D(n)≦T (No) is obtained, the processing proceeds to Step S19.

If D(n)>T (Yes) is obtained in a state in which the low concentration signal is generated (No in the Step S13), it is indicated that a difference between the sensor output value S(n) and the base value B(n) following with a slight delay therefrom is increased. In other words, it is supposed that the sensor output value S(n) is increased because of an increase in the concentration of the specific gas (oxidizing gas). Moreover, if D(n)>T (Yes) is obtained in a state in which the high concentration signal is generated (Yes in the Step S13), it is indicated that a difference between the current sensor output value S(n) and the base value B(n) somewhat reflecting a state in the past, that is, a state obtained immediately before an increase in the concentration of the oxidizing gas is still great, that is, the concentration of the oxidizing gas is not sufficiently reduced. At Step S18, the high concentration signal of the specific gas is generated or the generation of the high concentration signal is held. More specifically, the concentration signal LV is set to have the high level.

On the other hand, D(n)≦T (No in the Step S17) is obtained in a state in which the low concentration signal is generated (No in the Step S13), it is indicated that a difference between the current sensor output value S(n) and the base value B(n) following with a slight delay therefrom is not greatly increased and the base value B(n) follows. In other words, it is supposed that the concentration of the specific gas (oxidizing gas) is maintained to be low. Moreover, if D(n)≦T is obtained (No in the Step S17) in a state in which the high concentration signal is generated (Yes in the Step S13) it is indicated that the difference between the sensor output value S(n) and the base value B(n) somewhat reflecting the state in the past, that is, the state obtained immediately before an increase in the concentration of the oxidizing gas is decreased, that is, the concentration of the oxidizing gas is fully reduced. At the Step S19, the low concentration signal of the specific gas is generated or is maintained to be generated. More specifically, the concentration signal LV is set to have the low level.

Then, the processing proceeds from both of the Steps S18 and S19 to Step S20 where the last base values B(n) calculated at the Steps S14 and S15 are stored, and the time up of an A/D sampling time is waited at Step S21 and the processing returns to the Step S12. When the concentration of the specific gas is increased so that the difference value D(n) is increased, the high concentration signal is generated at the Step S18. Therefore, the decision of Yes is then obtained at the Step S13 and the processing proceeds to the Step S15. Consequently, a coefficient for calculating the base value B(n) is switched so that the base value B(n) is calculated by using the comparatively small second coefficient k2. Accordingly, the follow-up of the base value B(n) is carried out slowly for the sensor output value S(n). For this reason, it is supposed that the base value B(n) calculated at the Step S15 holds a state in the past in which the concentration of the specific gas is comparatively low, and a change in the concentration of the specific gas can be discriminated by calculating the difference value D(n) by using the base value B(n) as a reference.

To the contrary, when the difference value D(n) is decreased due to the reduction of the concentration of the specific gas, the low concentration signal is generated at the Step S19. Therefore, the decision of No is then obtained at the Step S13 and the processing proceeds to the Step S14 where the coefficient for calculating the base value B(n) is switched and the base value B(n) is calculated by using the comparatively large first coefficient k1. Accordingly, the base value B(n) sensitively follows the sensor output value S(n). For this reason, when the concentration of the specific gas is increased again, the difference value D(n) is increased again without the influence of a fluctuation in the specific gas in the past so that an increase in the concentration of the specific gas can be reliably grasped to generate a high concentration signal.

Figure 3:
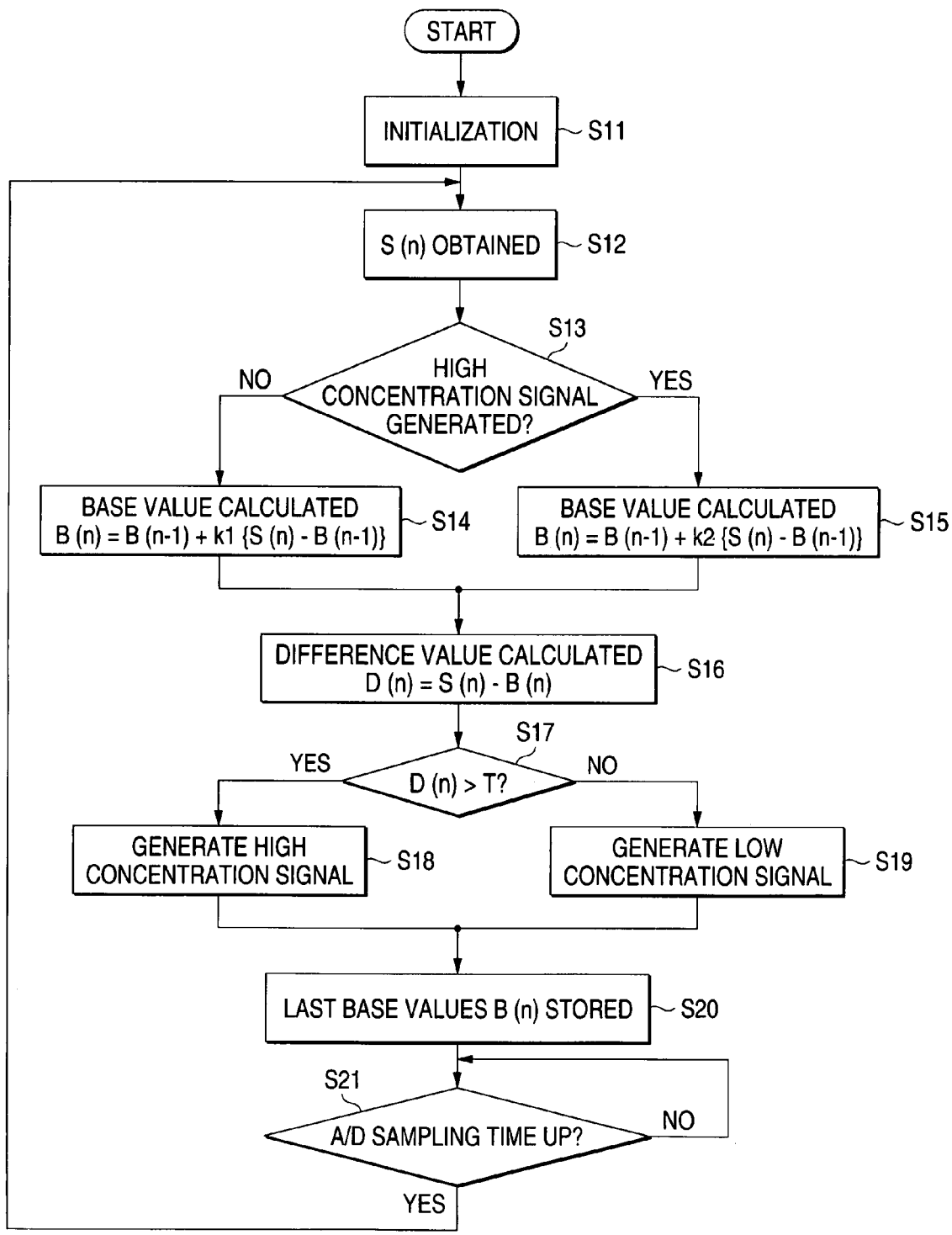
FIG. 3 is a flow chart showing a control in the microcomputer of the gas detecting device according to the first embodiment.
Figure 4:
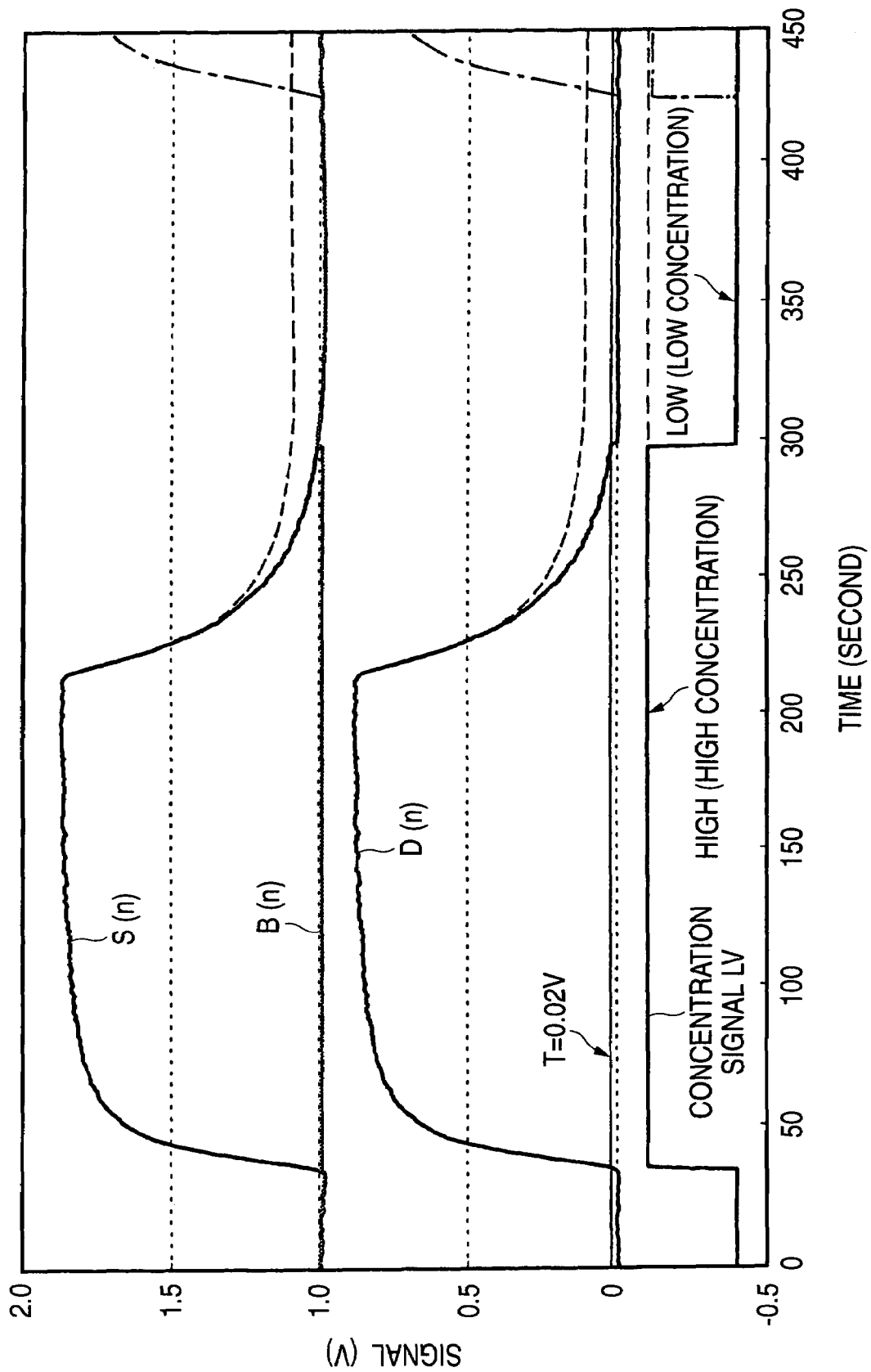
FIG. 4 is a chart showing a change in a sensor output value S(n), a base value B(n) and a difference value D(n) and a change in a concentration signal which are obtained when the concentration of NOx is increased for a certain period with a second coefficient k2=0 according to the first embodiment.
Figure 5:
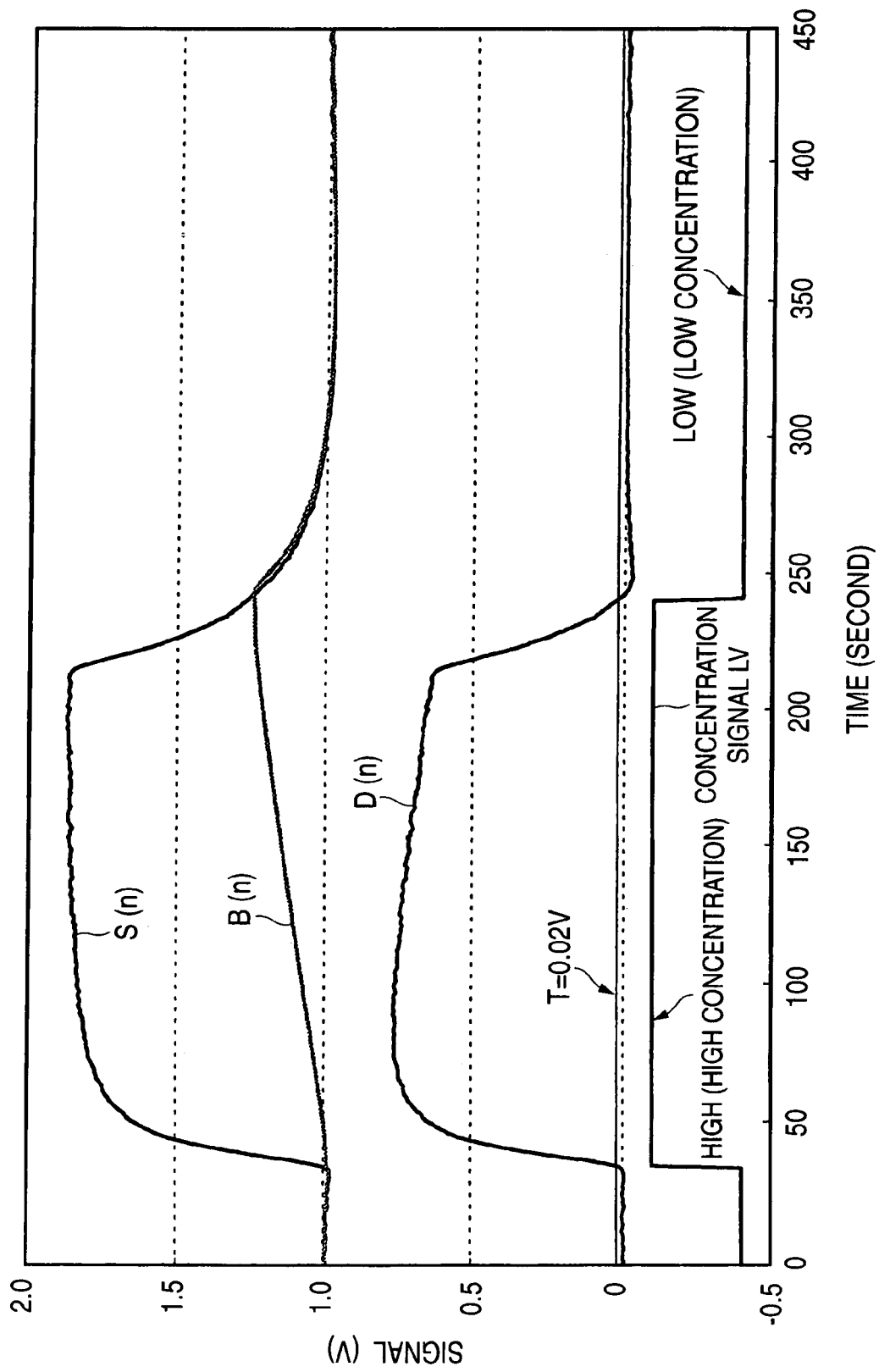
FIG. 5 is a chart showing a change in the sensor output value S(n), the base value B(n) and the difference value D(n) and a change in the concentration signal which are obtained when the concentration of NOx is increased for a certain period with the second coefficient k2>0.

Next, FIGS. 4 and 5 show an example of a change in the sensor output value S(n), the base value B(n), the difference value D(n) and the concentration signal LV which are obtained by the control in accordance with the flow chart of FIG. 3 when the concentration of NOx is increased and is then reduced. In the example, the gas sensor 11 is provided in a wind channel and clean air containing no NOx is originally caused to flow at a predetermined wind velocity. Then, air mixing NOx in a predetermined concentration is caused to flow for a predetermined time. While all the sensor output value S(n), the base value B(n) and the difference value D(n) are numeric values to be processed in the μC 16, they are expressed by a conversion into voltage values before the A/D conversion in the drawings for easy understanding. First of all, description will be given to the case in which the first coefficient k1=1/16, the second coefficient k2=0 and the concentration threshold T=0.02 V are set. For a time of 0 to approximately 35 seconds, the clean air is caused to flow and the sensor output value S(n) fluctuates by a slight noise but is maintained to have an almost constant value (approximately 1.0 V). When a rise in the NOx is started at the time of approximately 35 seconds, it is apparent that the sensor output value S(n) is correspondingly increased, and is maintained to have an almost constant value (approximately 1.8 V) for a time of approximately 70 to 210 seconds and is then reduced gradually for a time of approximately 210 to 300 seconds, and is returned to an original level (approximately 1.0 V).

On the other hand, the base value B(n) is originally maintained to have an almost constant value while slightly fluctuating in accordance with the sensor output value S(n) for the time of 0 to approximately 35 seconds. Accordingly, the difference value D(n) is maintained to almost 0 V. However, when the concentration of NOx is increased at the time of approximately 35 seconds, the sensor output value S(n) is started to be increased. Consequently, the base value B(n) cannot follow completely. Therefore, when the difference value D(n) is increased to exceed the threshold T=0.02 V, the concentration signal LV is changed from a low level to a high level to bring such a state that a high concentration signal is generated. After the next time, moreover, k2 (=0) is used for calculating the base value B(n). If k2=0 is set at the Step S15, B(n)=B(n-1) is obtained. Irrespective of the sensor output value S(n), therefore, the base value B(n) maintains a constant value, that is, a base value at the time of an increase in the concentration of the NOx. In FIG. 4, accordingly, the base value B(n) is constant for a time of approximately 35 to 300 seconds.

Then, when the concentration of the NOx is gradually reduced and the sensor output value S(n) is decreased, the difference value D(n) is also decreased. When the difference value D(n) is finally less than the concentration threshold T=0.02 V at the time of approximately 300 seconds, it is decided that the concentration of the NOx is reduced and the concentration signal LV is changed from the high level to the low level to bring such a state that a low concentration signal is generated. Correspondingly, since the base value B(n) is calculated by using the first coefficient k1, it is changed following the sensor output value S(n). Accordingly, even if the concentration of the NOx is increased again so that the sensor output value S(n) is increased as shown in a one-dotted line of FIG. 4, the rise can be immediately detected to set the concentration signal LV to have the high level, thereby generating the high concentration signal.

In the above description, when calculating the base value B(n) during the generation of the high concentration signal, the second coefficient k2=0 is set. As described above, however, the sensor resistance value Rs of the gas sensor 11 drifts by the influence of a temperature, a humidity, a wind velocity and the like as well as the concentration of the specific gas. Accordingly, if the drift is generated in such a direction that the sensor resistance value Rs is increased while the concentration of the NOx is maintained to be high (for example, for the time of approximately 35 to 210 seconds), the sensor output value S(n) is not returned to the original level (approximately 1.0 V) and the difference value D(n) does not approximate to 0 V as shown in a broken line of FIG. 4 even if the concentration of the NOx is reduced to cause the clean air to flow. Accordingly, since the concentration threshold T=0.02 V is at least maintained, the concentration signal LV does not have the low level and the high concentration signal can be continuously generated for a long time as shown in the broken line irrespective of the fact that the concentration of the NOx is actually reduced sufficiently.

Therefore, it is preferable that the second coefficient k2>0 should be set. FIG. 5 shows a result in the same case as described above except that the second coefficient k2=1/2048 is set. Thus, the high concentration signal is generated at the time of approximately 35 seconds and the base value B(n) is subsequently calculated by using the second coefficient k2.

The base value B(n) is gradually increased to slowly approximate to the sensor output value S(n). Accordingly, since the base value B(n) approximates to the sensor output value S(n) after a long time passes, the difference value D(n) always approximates to 0 and has a small value. For this reason, even if the drift is generated, the difference value D(n) is always less than the concentration threshold T and the concentration signal LV is returned to the low level, that is, the low concentration signal is generated. When the low concentration signal is generated, the coefficient of the base value B(n) is switched and the calculation is carried out by using the first coefficient k1 (after a time of approximately 240 seconds). Therefore, it can be understood that the base value B(n) is completely changed to follow the sensor output value S(n) sensitively. Also in this case, accordingly, even if the concentration of the NOx is increased again after the time of approximately 240 seconds, the rise can be reliably detected.

(First Variant)

Next, a variant of the first embodiment will be described. While a gas detecting device 40 and an autoventilation system 140 for a vehicle including the gas detecting device 40 according to a first variant are processed by almost the same structure and processing flow as those in the first embodiment, there are some differences. More specifically, the gas sensor element of such a type that the concentration of the oxidizing gas component such as NOx is increased and the sensor resistance value Rs is increased by a reaction to the oxidizing gas component, if any, is used as the gas sensor element 11 in the first embodiment. On the other hand, a gas sensor element 41 of such a type that the concentration of a reducing gas component such as CO or HC is increased and a sensor resistance value Rs is reduced by a reaction to the reducing gas component, if any, is used in the first variant. Correspondingly, a sensor resistance value converting circuit 44 according to the first variant is different in that when a sensor output potential Vs corresponding to the sensor resistance value Rs of the gas sensor element 41 is output to increase the concentration of the reducing gas such as CO or HC, the sensor resistance value Rs is decreased and the sensor output potential Vs is reduced. Furthermore, the flow of a processing in a μC16 is also different slightly. Accordingly, different portions will be mainly described, and the same portions have the same symbols and numbers and description will be omitted or simplified.

First of all, the gas detecting device 40 will be described with reference to FIG. 6. The gas detecting device 40 uses the gas sensor element 41 comprising an oxide semiconductor of such a type that a gas concentration is increased and the sensor resistance value Rs is reduced by a reaction to the reducing gas component as described above, if any. A sensor resistance value converting circuit 44 outputs the sensor output potential Vs corresponding to the sensor resistance value Rs of the gas sensor element 41. In the sensor resistance value converting circuit 44, when the concentration of the reducing gas is increased, the sensor output potential Vs on an operation point Pd is reduced. The sensor output potential Vs is A/D converted every 0.25 second by an A/D converting circuit 15 and is input as a sensor output value S(n) to an input terminal 17 of the μC16.

Furthermore, an output terminal 18 of the a μC16 sends a concentration signal LV to be any of a high concentration signal and a low concentration signal which indicate the concentration of the reducing gas component in order to control an electronic control assembly 20 in the same manner as in the first embodiment, and a flap 34 of a ventilation system 30 is controlled by the electronic control assembly 20. In the μC16, the sensor output value S(n) sent from the input terminal 17 is processed in accordance with a flow which will be described below, and a change in the concentration of the reducing gas component is detected based on the sensor resistance value Rs of the gas sensor element 41, a variation thereof or the like.

Next, the control in the μC16 according to the variant will be described in accordance with a flow chart of FIG. 7. When the engine of an automobile is driven, the control system is activated and the active state of the gas sensor element 41 is waited, and initialization is first carried out at Step S11 in the same manner as in the first embodiment. Then, the processing proceeds to Step S12 where the sensor output value S(n) is sequentially read. At Step S13, next, it is decided whether or not the concentration signal LV generates a high concentration signal at the present time. If a low concentration signal is generated (No), the processing proceeds to Step S44. On the other hand, if the high concentration signal is generated (Yes), the processing proceeds to Step S45.

At the Step S44, a base value B(n) is calculated in accordance with the following equation by utilizing a last base value B(n−1) and the sensor output value S(n) and the processing proceeds to Step S46. $B(n)=B(n-1)+k3\{S(n)-B(n-1)\}$, wherein a third coefficient k3 is set to $0<k3<1$. On the other hand, at the Step S45, the base value B(n) is calculated in accordance with the following equation by utilizing the last base value B(n−1) and the sensor output value S(n) and the processing proceeds to the Step S46. $B(n)=B(n-1)+k4\{S(n)-B(n-1)\}$, wherein a fourth coefficient k4 is set to $0 \leq k4 < k3 < 1$. In the same manner as described in the first embodiment, the base value B(n) has the degree of follow-up for the sensor output value S(n) varied depending on the coefficients k3 and k4 to be used, and the base value B(n) follows the sensor output value S(n) comparatively sensitively with a slight delay if the comparatively great third coefficient k3 (k3>k4) is used (Step S44). On the other hand, if the comparatively small fourth coefficient k4 (k4<k3) is used (Step S45), the base value B(n) is changed less sensitively and the follow-up is carried out slowly.

At the Step S46, a difference value D(n) is calculated in accordance with an equation of $D(n)=B(n)-S(n)$ which is different from that in the first embodiment and is compared with a concentration threshold T at Step S17. If $D(n)>T$ is obtained (yes), the processing proceeds to Step S18. If $D(n) \leq T$ is obtained (No), the processing proceeds to Step S19.

At the Step S18, the high concentration signal of the specific gas is generated or the generation of the high concentration signal is maintained in the same manner as in the first embodiment. On the other hand, at the Step S19, the low concentration signal of the specific gas is generated or the generation is maintained. Then, the processing proceeds from both of the Steps S18 and S19 to Step S20 where the last base values B(n) calculated at the Steps S14 and S15 are stored, and the time up of an A/D sampling time is waited at Step S21 and the processing returns to the Step S12.

Figure 7:
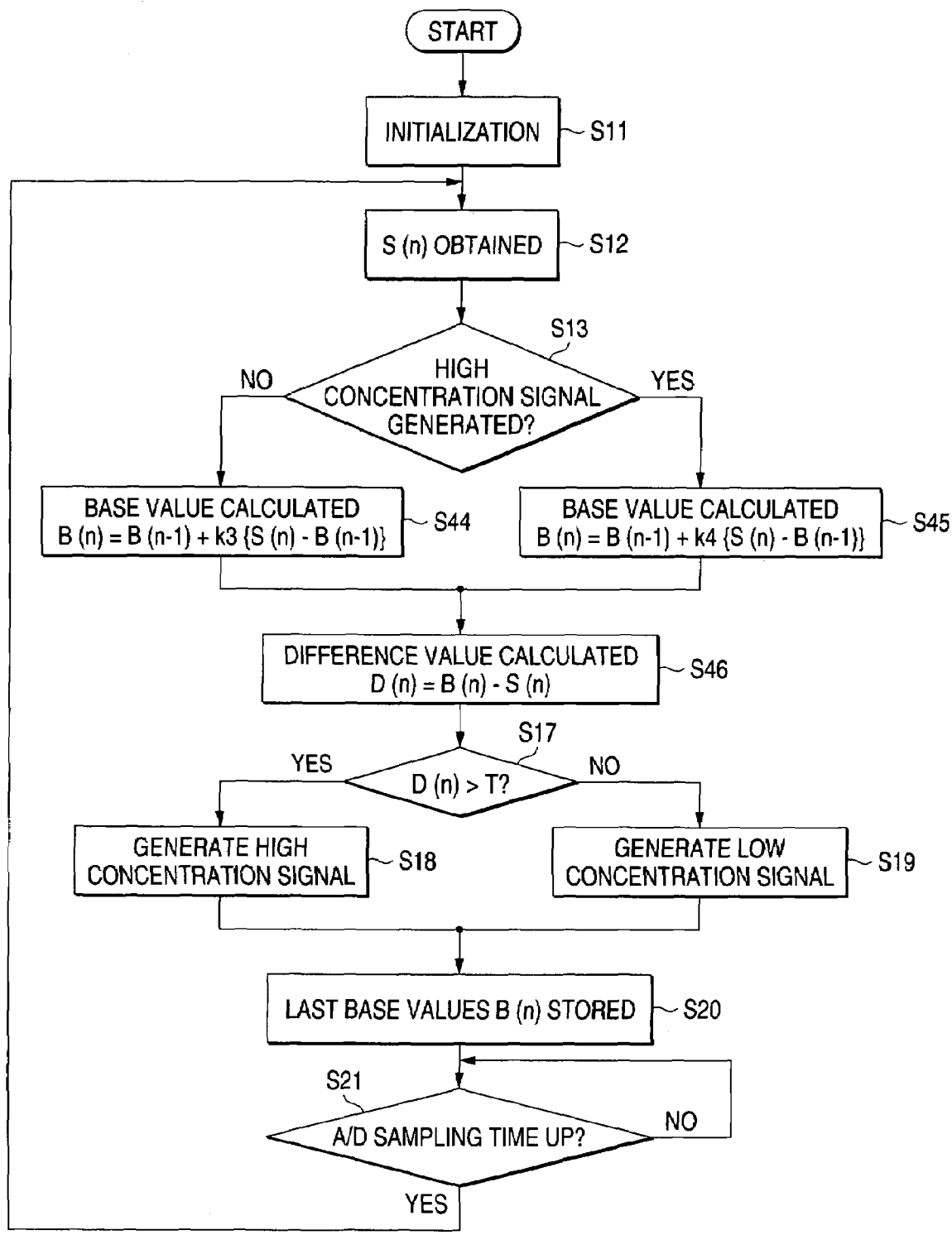
FIG. 7 is a flow chart showing a control in the microcomputer of the gas detecting device according to the first variant.
Figure 8:
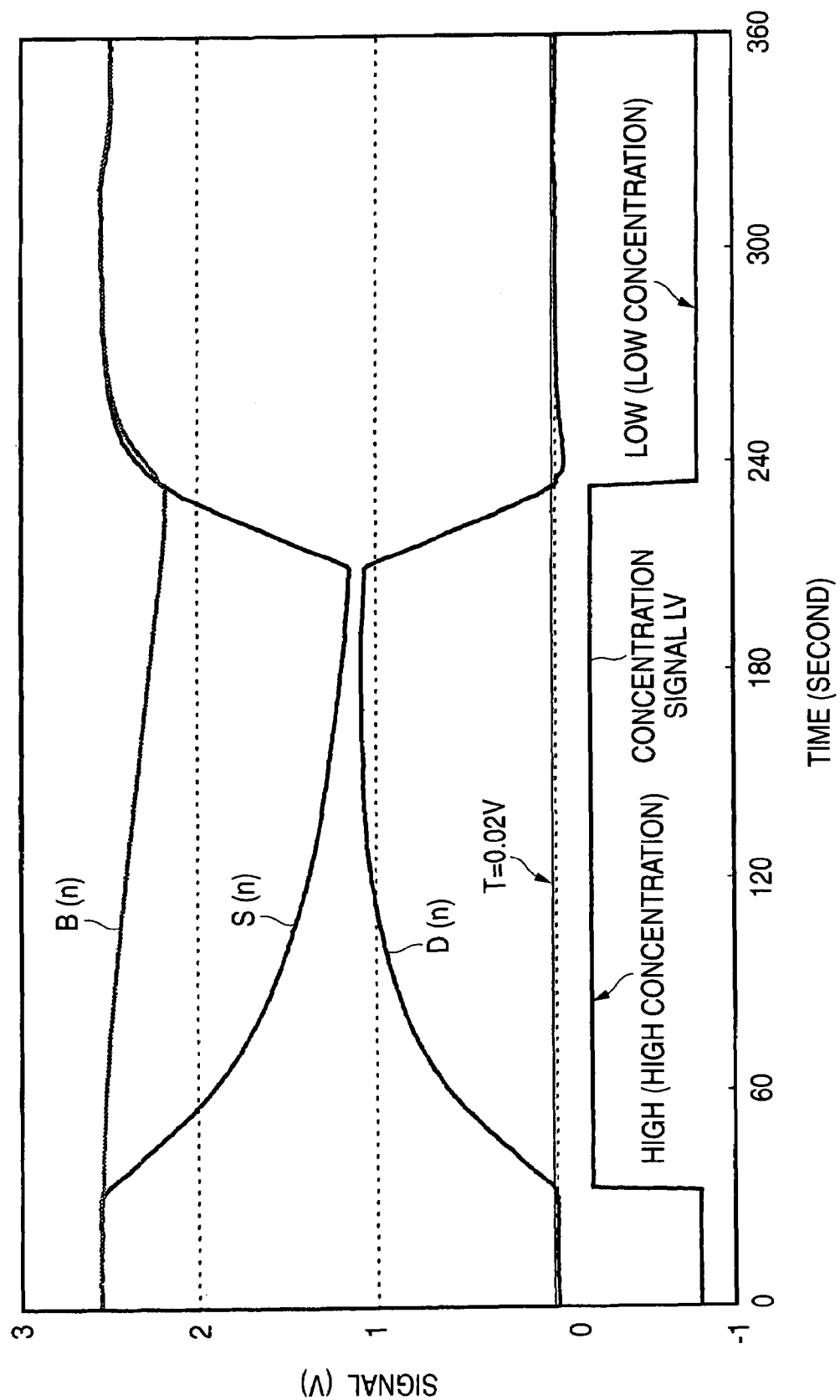
FIG. 8 is a chart showing a change in a sensor output value S(n), a base value B(n) and a difference value D(n) and a change in a concentration signal which are obtained when the concentration of CO is increased for a certain period according to the first variant.

Next, FIG. 8 shows an example of a change in the sensor output value S(n), the base value B(n), the difference value D(n) and the concentration signal LV which are obtained by the control in accordance with the flow chart of FIG. 7 when the concentration of CO is increased and is then reduced. In the example, the gas sensor 41 is provided in a wind channel and clean air containing no CO is originally caused to flow at a predetermined wind velocity. Then, air mixing CO in a predetermined concentration is caused to flow for a predetermined time. While all the sensor output value S(n), the base value B(n), the difference value D(n) and the concentration threshold T are numeric values to be processed in the μC 16, they are expressed by a conversion into voltage values before the A/D conversion in the drawings for easy understanding. Description will be given to the case in which the third coefficient k3=1/16, the fourth coefficient k4=1/1920 and the concentration threshold T=0.02 V is set. For a time of 0 to approximately 35 seconds, the clean air is caused to flow and the sensor output value S(n) fluctuates by a slight noise but is maintained to have an almost constant value (approximately 2.5 V). When a rise in the CO is started at the time of approximately 35 seconds, the sensor output value S(n) is correspondingly reduced. Then, it is apparent that the sensor output value S(n) is gradually increased again for a time of approximately 210 to 245 seconds and is finally returned to an original level (approximately 2.5 V).

On the other hand, the base value B(n) is originally maintained to have an almost constant value while slightly fluctuating in accordance with the sensor output value S(n) for the time of 0 to approximately 35 seconds. Accordingly, the difference value D(n) is maintained to almost 0. However, when the concentration of the CO is increased at the time of approximately 35 seconds, the sensor output value S(n) is started to be decreased. Consequently, the base value B(n) cannot follow completely. Therefore, when the difference value D(n) to be a difference is increased to exceed the threshold T=0.02 V, the concentration signal LV is changed from a low level to a high level and a high concentration signal is generated. After the next time, moreover, k4 (=1/1920) is used for calculating the base value B(n). If k4=1/1920 (≠0) is set at the Step S45, the base value B(n) is gradually decreased to slowly approximate to the sensor output value S(n).

Then, when the concentration of the CO is gradually reduced and the sensor output value S(n) is increased, the difference value D(n) is also decreased. When the difference value D(n) is finally less than the concentration threshold T=0.02 V at the time of approximately 235 seconds, it is decided that the concentration of the CO is reduced and the concentration signal LV is changed from the high level to the low level to be brought into such a state that a low concentration signal is generated. Correspondingly, since the base value B(n) is calculated by using the third coefficient k3, it is changed following the sensor output value S(n) again. Accordingly, even if the concentration of the CO is increased again so that the sensor output value S(n) is decreased, this can be immediately detected to set the concentration signal LV to have the high level, thereby generating the high concentration signal.

Figure 6:
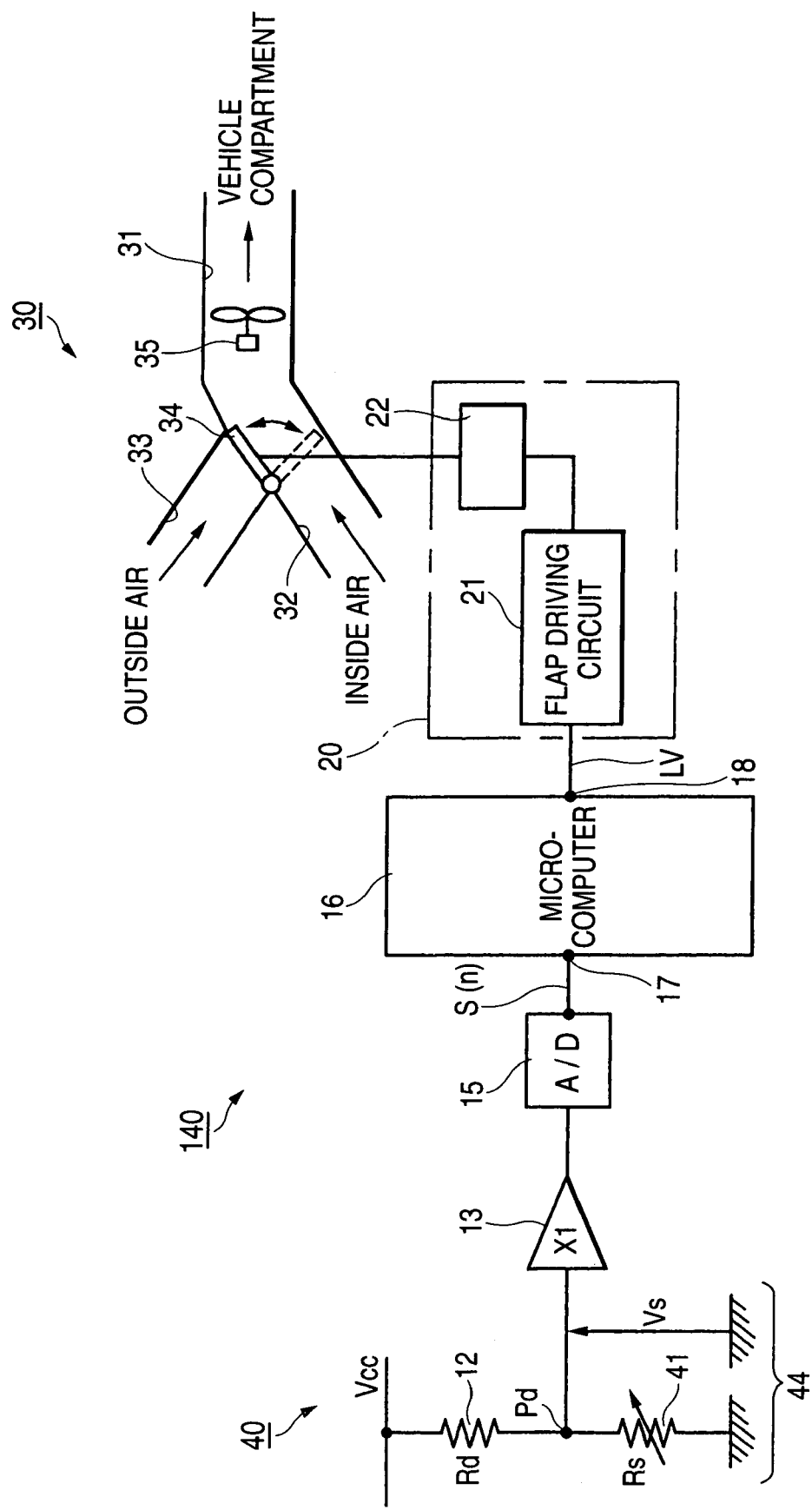
FIG. 6 is a diagram showing the summary of a gas detecting device and an autoventilation system for a vehicle according to a first variant.

Also in such control, an instruction for switching the flap 34 in the flap driving circuit 21 can be given by using the obtained concentration signal LV (the low concentration signal and the high concentration signal) to control outside air introduction and inside air circulation (full open/full closing) by the same control (see FIG. 2) as that in the first embodiment in the autoventilation system 140 for a vehicle (see FIG. 6). While the fourth coefficient k4=0 has not been described in the first variant, a change in the concentration of the reducing gas can be measured with k4=0 in the same manner as in the first embodiment. As described in the first embodiment, in the case in which the drift is generated toward such a side that the sensor resistance value Rs of the gas sensor element 41 is decreased by the influence of a change in an environment, the low concentration signal cannot be generated even if the concentration of the reducing gas component is sufficiently reduced in some cases. Therefore, it is preferable that k4>0 should be set as described above.

(Second Variant)

Next, a second variant will be described. The second variant is different from the first variant in that the same gas detecting device 10 and the same autoventilation system 100 for a vehicle comprising the gas detecting device 10 (see FIG. 1) as those in the first embodiment are provided. More specifically, the system serves to detect a change in the concentration of an oxidizing gas component such as NOx and to open and close a flap 34 based thereon. Since a processing flow in a μC16 is varied and a concentration threshold has a hysteresis characteristic, different portions will be mainly described, and the same portions have the same symbols and numbers and description will be omitted or simplified.

Figure 9:
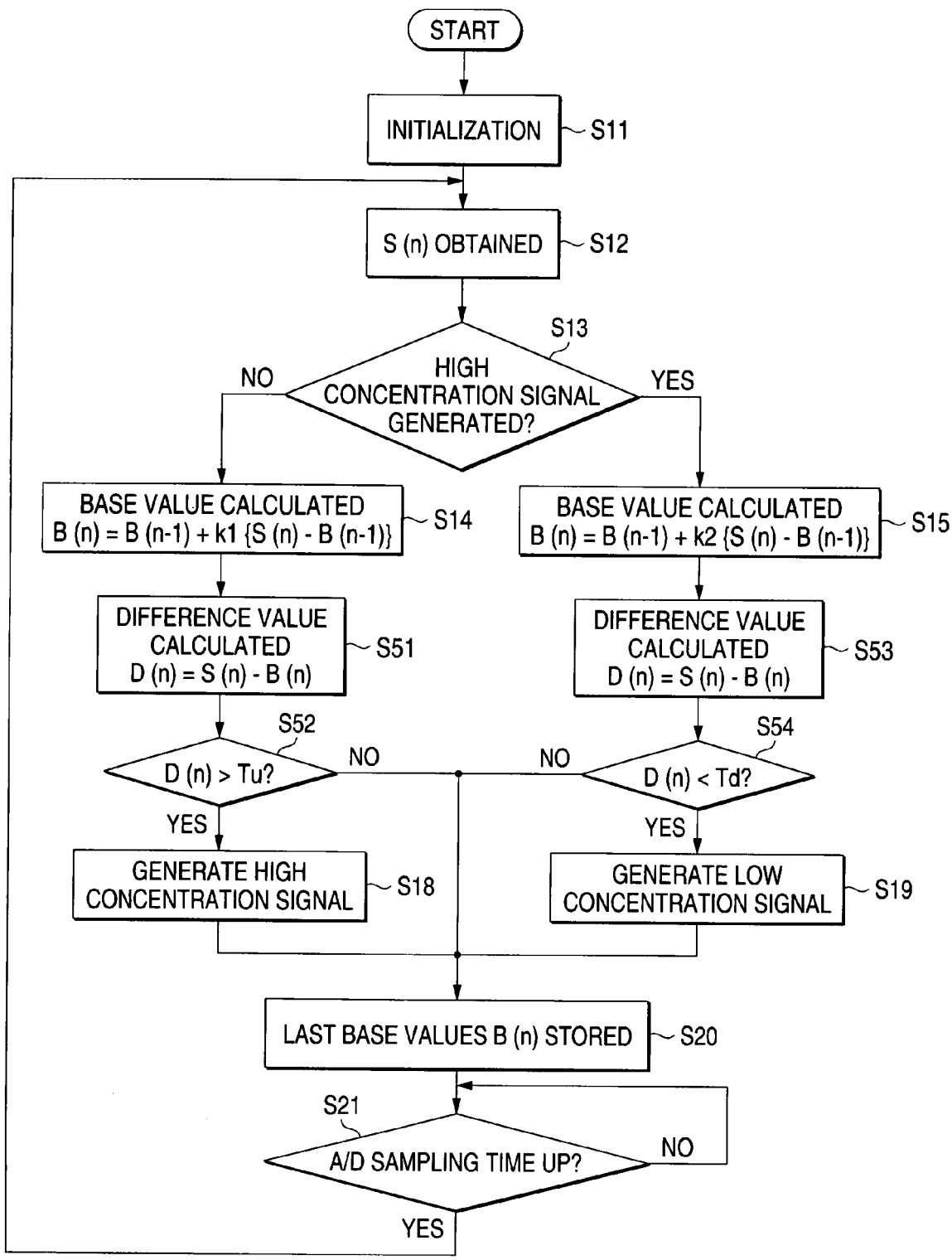
FIG. 9 is a flow chart showing a control in the microcomputer of a gas detecting device according to a second variant.

A control in the μC16 according to the second variant will be described in accordance with a flow chart of FIG. 9. Steps S11 to S13 are the same as those in the first embodiment. If a decision is No, that is, a low concentration signal is generated at the Step S13, the processing proceeds to Step S14. If the decision is Yes, that is, a high concentration signal is generated, the processing proceeds to Step S15.

At the Step S14, a base value B(n) is calculated in the same manner as in the first embodiment and the processing proceeds to Step S51. On the other hand, at the Step S15, the base value B(n) is calculated in the same manner as in the first embodiment and the processing proceeds to Step S53. As described above, the base value B(n) is varied in the degree of follow-up for a sensor output value S(n) depending on coefficients k1 and k2 to be used.

The difference value D(n) is calculated in accordance with an equation of D(n)=S(n)−B(n) at the Step S51 and is compared with a high concentration threshold Tu at Step S52. If D(n)>Tu is obtained (Yes), the processing proceeds to Step S18. If D(n)≦Tu is obtained (No), the processing exactly proceeds to Step S20.

At the Step S52, the decision of Yes is obtained with D(n)>Tu in a state in which a low concentration signal is generated (No in the Step S13). Therefore, it is indicated that a difference between the sensor output value S(n) and the base value B(n) following with a slight delay therefrom is increased. More specifically, it is supposed that the sensor output value S(n) is increased because of an increase in the concentration of a specific gas (an oxidizing gas). At the Step 18, the high concentration signal of the specific gas is generated.

On the other hand, the difference value D(n) is calculated in accordance with an equation of D(n)=S(n)−B(n) at the Step S53 and is compared with a low concentration threshold Td at Step S54. The low concentration threshold Td is smaller than the high concentration threshold Tu (Tu>Td). If D(n)<Td is obtained (Yes), the processing proceeds to Step S19. If D(n)≧Td is obtained (No), the processing exactly proceeds to the Step S20.

At the Step S54, the decision of Yes is obtained with D(n)<Td in a state in which the high concentration signal is generated (Yes in the Step S13). Therefore, it is indicated that a difference between the sensor output value S(n) and the base value B(n) somewhat reflecting a state in which the concentration of the oxidizing gas has not been increased is reduced, that is, the concentration of the oxidizing gas is sufficiently reduced. Therefore, the low concentration signal of the specific gas is generated at the Step S19.

Then, the processing proceeds from both of the Steps S18 and S19 to the Step S20 where the last base values B(n) calculated at the Steps S14 and S15 are stored, and the time up of an A/D sampling time is waited at Step S21 and the processing returns to the Step S12.

In the processing according to the second variant, the two thresholds Tu and Td are used for the concentration thresholds, and the high concentration signal is generated when the difference value D(n) is greater than the high concentration threshold Tu (D(n)>Tu) and the low concentration signal is generated when the difference value D(n) is smaller than the low concentration threshold Td (D(n)<Td). Consequently, there is an advantage that chattering for often exchanging the high concentration signal and the low concentration signal is generated with difficulty also in the case in which the sensor output value S(n) or the difference value D(n) fluctuates due to a noise or the like.

(Third Variant)

Next, a third variant will be described. In the second variant, a concentration threshold has a hysteresis in the first embodiment. On the other hand, in the third variant, a concentration threshold has a hysteresis in the first variant. In the third variant, accordingly, there are provided the gas detecting device 40 and the autoventilation system 140 for a vehicle comprising the gas detecting device 40 in the same manner as in the first variant. More specifically, a system serves to detect a change in the concentration of a reducing gas component such as CO and to open and close a flap 34 based thereon. However, a different processing flow is executed in a μC 16 and the concentration threshold has a hysteresis characteristic. Therefore, different portions will be mainly described, and the same portions have the same symbols and numbers and description will be omitted or simplified.

Figure 10:
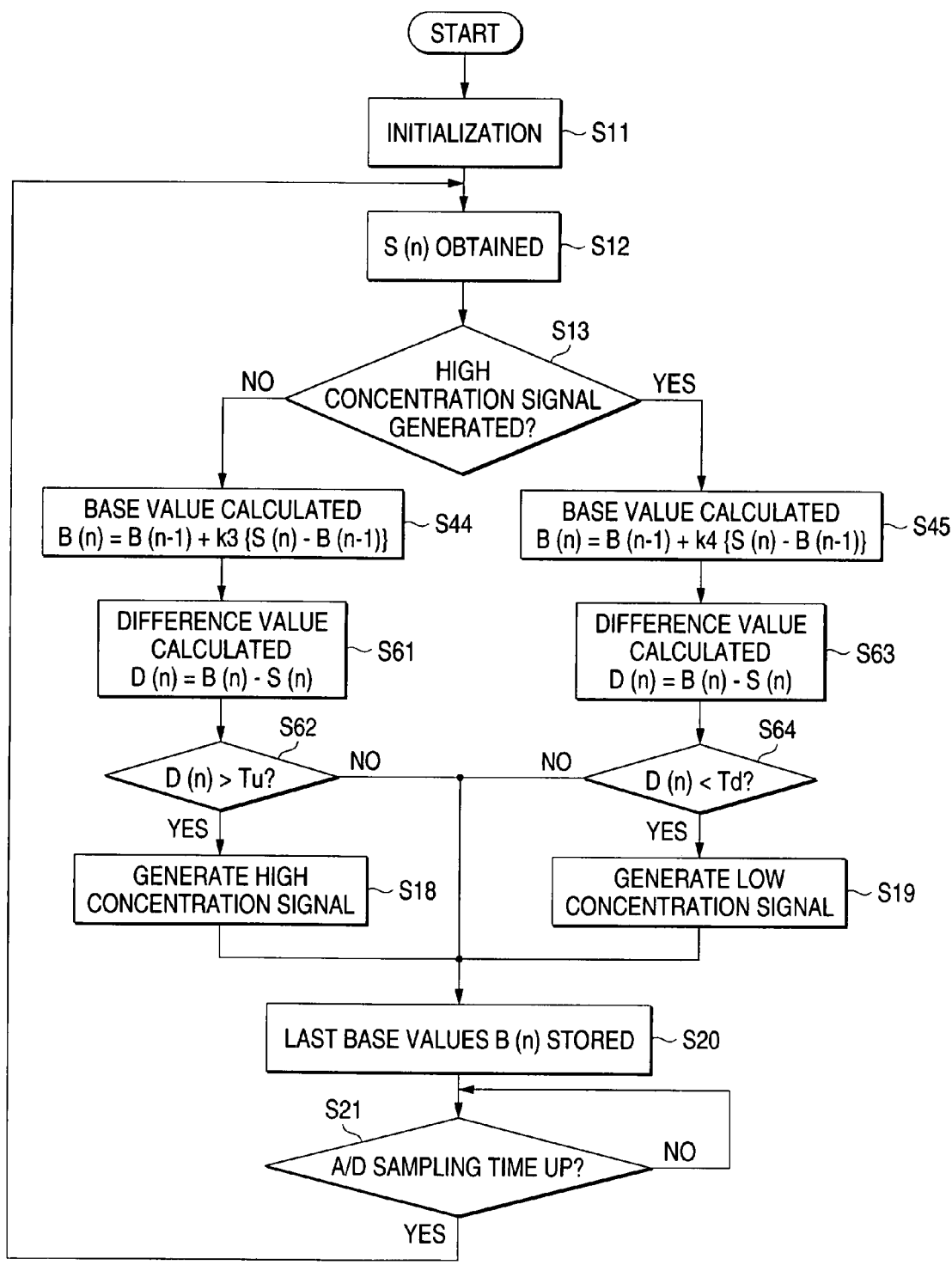
FIG. 10 is a flow chart showing a control in the microcomputer of a gas detecting device according to a third variant.

A control in the μC 16 according to the third variant will be described in accordance with a flow chart of FIG. 10. In Steps S11 to S13, the same processing as that in the first variant is carried out. At the Step S13, if a decision is No, that is, a low concentration signal is generated, the processing proceeds to Step S44. If the decision is Yes, that is, a high concentration signal is generated, the processing proceeds to Step S45.

At the Step S44, a base value B(n) is calculated in the same manner as that in the first variant and the processing proceeds to Step S61. On the other hand, also in the Step S45, the base value B(n) is calculated in the same manner as in the first variant and the processing proceeds to Step S63. As described above, the base value B(n) has a different degree of follow-up for a sensor output value S(n) depending on coefficients k3 and k4 to be used.

A difference value D(n) is calculated in accordance with an equation of D(n)=B(n)−S(n) at the Step S61 and is compared with a high concentration value Tu at Step S62. If D(n)>Tu is obtained (Yes), the processing proceeds to Step S18. If D(n)≦T is obtained (No), the processing exactly proceeds to Step S20.

At the Step S62, the decision of Yes is obtained with D(n)>Tu in a state in which a low concentration signal is generated (No in the Step S13). Therefore, it is indicated that a difference between the sensor output value S(n) and the base value B(n) following with a slight delay therefrom is increased. More specifically, it is supposed that the sensor output value S(n) is increased because of an increase in the concentration of a specific gas (a reducing gas). At the Step S18, the high concentration signal of the specific gas is generated.

On the other hand, the difference value D(n) is calculated in accordance with an equation of D(n)=B(n)−S(n) at the Step S63 and is compared with a low concentration threshold Td at Step S64. The low concentration threshold Td is smaller than the high concentration threshold Tu (Tu>Td). If D(n)<Td is obtained (Yes), the processing proceeds to Step S19. If D(n)≧Td is obtained (No), the processing exactly proceeds to the Step S20.

At the Step S64, the decision of Yes is obtained with D(n)<Td in a state in which the high concentration signal is generated (Yes in the Step S13). Therefore, it is indicated that a difference between the sensor output value S(n) and the base value B(n) somewhat reflecting a state in which the concentration of the reducing gas has not been increased is reduced, that is, the concentration of the oxidizing gas is sufficiently reduced. Therefore, the low concentration signal of the specific gas is generated at the Step S19.

Then, the processing proceeds from both of the Steps S18 and S19 to the Step S20 where the last base values B(n) calculated at the Steps S44 and S45 are stored, and the time up of an A/D sampling time is waited at Step S21 and the processing returns to the Step S12.

Also in the processing according to the third variant, the two thresholds Tu and Td are used for the concentration thresholds, and the high concentration signal is generated when the difference value D(n) is greater than the high concentration threshold Tu (D(n)>Tu) and the low concentration signal is generated when the difference value D(n) is smaller than the low concentration threshold Td (D(n)<Td). Consequently, there is an advantage that chattering for often exchanging the high concentration signal and the low concentration signal is generated with difficulty.

Second Embodiment

Next, a second embodiment will be described. Also in the second embodiment, there are provided the same gas detecting device 10 and the same autoventilation system 100 for a vehicle comprising the gas detecting device 10 (see FIG. 1) as those in the first embodiment. More specifically, the system serves to detect a change in the concentration of an oxidizing gas component such as NOx and to open and close a flap 34 based thereon. However, a different processing flow is executed in a μC16 and there are four kinds of concentration level signals LV (LV=0, 1, 2, 3) corresponding to three concentration levels or more, more specifically, four concentration levels in place of two level signals, that is, high and low concentration signals, and three interlevel thresholds T1, T2 and T3 (T1<T2<T3) for dividing the concentration levels. Accordingly, different portions will be mainly described, and the same portions have the same symbols and numbers and description will be omitted or simplified.

A control in the μC16 according to the second embodiment will be described in accordance with a flow chart of FIG. 11. In the same manner as in the first embodiment, when the engine of an automobile is driven, the control system is activated, and a gas sensor element 11 is waited to be brought into an active state and initialization is carried out at Step S71. For the initialization, an original sensor output value S(0) is stored as a base value B(0) (B(0)=S(0)). Moreover, a signal corresponding to LV=0 is generated as a concentration level signal LV. More specifically, a PWM (pulse width modulation) signal is output as a signal to be output from an output terminal 18 of the μC16, and a duty ratio is caused to correspond to a concentration level signal to generate a PWM signal having a duty ratio of 15% as the signal equivalent to LV=0. Similarly, a PWM signal having a duty ratio of 30% is generated as a signal corresponding to LV=1, a PWM signal having a duty ratio of 50% is generated as a signal corresponding to LV=2, and a PWM signal having a duty ratio of 70% is generated as a signal corresponding to LV=3.

Then, the processing proceeds to Step S72 where a sensor output potential Vs is A/D converted every 0.25 second and a sensor output value S(n) is sequentially read. At Step S73, next, it is decided whether or not a concentration level signal LV=0, that is, a signal indicative of a level having the lowest concentration is generated at the present time. If the decision is No, that is, LV=1, 2 or 3 is obtained, the processing proceeds to Step S74. On the other hand, if the decision is Yes, that is, the signal corresponding to LV=0 is generated, the processing proceeds to Step S75.

At the Step S74, a base value B(n) is calculated in the same manner as in the first embodiment and the processing proceeds to Step S76. On the other hand, also in the Step S75, the base value B(n) is calculated in the same manner as in the first embodiment and the processing proceeds to the Step S76. As described above, the base value B(n) has a different degree of follow-up for the sensor output values (n) depending on coefficients k1 and k2 to be used. At the Step S76, a difference value D(n) is calculated in accordance with an equation of $D(n)=S(n)-B(n)$ and it is decided whether or not the concentration level signal LV is switched and generated in a subroutine at Step S77.

Figure 12:
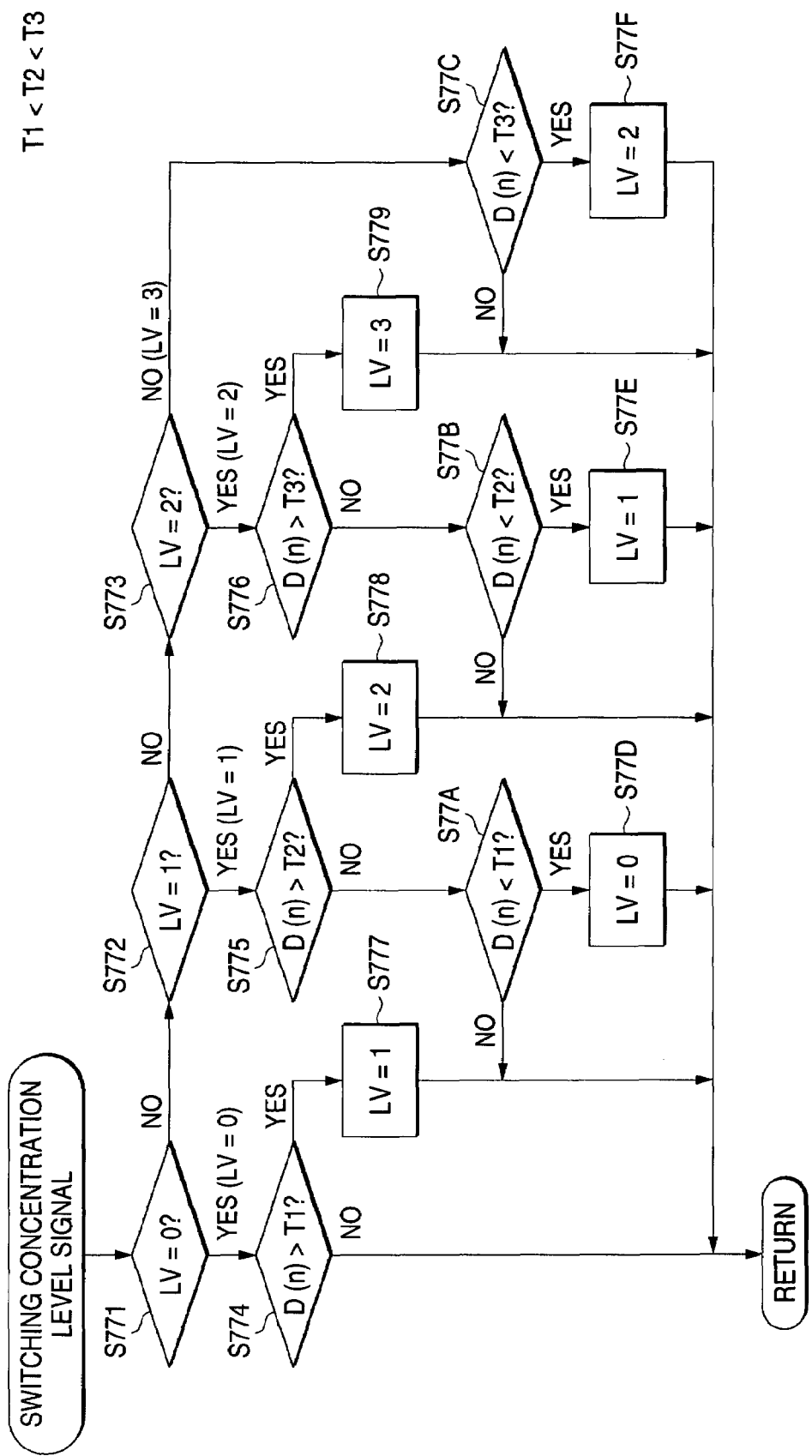
FIG. 12 is a flow chart showing the contents of a subroutine for concentration level signal switching generation in the control flow according to the second embodiment.

FIG. 12 shows the contents of the Step S77. When the processing proceeds to the Step S77, it is first decided whether the currently generated concentration level signal LV is set to LV=0 corresponding to the lowest concentration level at Step S771. If the decision is Yes, that is, LV=0 is obtained, the processing proceeds to Step S774. On the other hand, the decision is No, that is, LV=1, 2 or 3 is obtained, the processing proceeds to Step S772.

At the Step S772, it is decided whether or not the currently generated concentration level signal LV is set to LV=1 corresponding to a second lowest concentration level. If the decision is Yes, that is, LV=1 is obtained, the processing proceeds to Step S775. On the other hand, the decision is No, that is, LV=2 or 3 is obtained, the processing proceeds to Step S773. At the Step S773, furthermore, it is decided whether or not the currently generated concentration level signal LV is set to LV=2 corresponding to a third lowest concentration level. If the decision is Yes, that is, LV=2 is obtained, the processing proceeds to Step S776. On the other hand, the decision is No, that is, LV=3 corresponding to the highest concentration level is obtained, the processing proceeds to Step S77C. Thus, it is possible to carry out a classification into any concentration level signal LV for each case.

At the Step S774, it is decided whether or not the difference value D(n) is greater than a first interlevel threshold T1. If the decision is No, that is, $D(n) \leq T1$ is obtained, it is not necessary to carry out a change from the lowest concentration level to a higher concentration level. Therefore, the processing passes through the subroutine and returns to a main routine. On the other hand, when the decision is Yes, that is, D(n)>T1 is obtained, the processing proceeds to Step S777 where the concentration level signal LV is set to LV=1 which is higher by one rank and the processing then returns to the main routine. More specifically, the duty ratio of the PWM signal to be output from the output terminal 18 of the μC16 is changed from 15% to 30% and the processing then returns to the main routine. At the Step S775, moreover, it is decided whether or not the difference value D(n) is greater than a second interlevel threshold T2. When the decision is No, that is, D(n)<T2 is obtained, the processing proceeds to Step S77A. On the other hand, when the decision is Yes, that is, D(n)>T2 is obtained, the processing proceeds to Step S778 where the concentration level signal LV is set to LV=2 which is higher than a current level by one rank and the processing then returns to the main routine. More specifically, the duty ratio of the PWM signal is changed from 30% to 50% and the processing then returns to the main routine. At the Step S776, furthermore, it is decided whether or not the difference value D(n) is greater than a third interlevel threshold T3. If the decision is No, that is, $D(n) \leq T3$ is obtained, the processing proceeds to Step S77B. On the other hand, when the decision is Yes, that is, D(n)>T3 is obtained, the processing proceeds to Step S779 where the concentration level signal LV is set to LV=3 which is higher than a current level by one rank and the processing then returns to the main routine. More specifically, the duty ratio of the PWM signal is changed from 50% to 70% and the processing then returns to the main routine.

At the Step S77A, it is decided whether or not the difference value D(n) is smaller than the first interlevel threshold T1. If the decision is No, that is, $D(n) \geq T1$ is obtained, it is not necessary to decrease the rank of a current concentration level. Therefore, the processing passes through the subroutine and returns to the main routine. On the other hand, when the decision is Yes, that is, D(n)<T1 is obtained, the processing proceeds to Step S77D where the concentration level signal LV is set to LV=0 which is lower by one rank and the processing then returns to the main routine. More specifically, the duty ratio of the PWM signal to be output from the output terminal 18 of the μC16 is changed from 30% to 15% and the processing then returns to the main routine. At the Step S77B, moreover, it is decided whether or not the difference value D(n) is smaller than the second interlevel threshold T2. When the decision is No, that is, $D(n) \geq T2$ is obtained, the processing returns to the main routine because it is not necessary to decrease the rank of the current concentration level. On the other hand, when the decision is Yes, that is, D(n)<T2 is obtained, the processing proceeds to Step S77E where the concentration level signal LV is set to LV=1 which is lower than the current level by one rank and the processing then returns to the main routine. More specifically, the duty ratio of the PWM signal is changed from 50% to 30% and the processing then returns to the main routine. At the Step S77C, furthermore, it is decided whether or not the difference value D(n) is smaller than the third interlevel threshold T3. If the decision is No, that is, $D(n) \leq T3$ is obtained, the processing returns to the main routine because it is not necessary to decrease the rank of the current concentration level. On the other hand, when the decision is Yes, that is, D(n)<T3 is obtained, the processing proceeds to Step S77F where the concentration level signal LV is set to LV=2 which is lower than the current level by one rank and the processing then returns to the main routine. More specifically, the duty ratio of the PWM signal is changed from 70% to 50% and the processing then returns to the main routine.

Thereafter, the last base values B(n) calculated at the Steps S74 and S75 are stored at Step S78 and the time up of an A/D sampling time is waited at Step S79, and the routine then returns to the Step S72.

Thus, when the concentration of a specific gas is increased so that the difference value D(n) becomes greater to exceed the first interlevel threshold T1, the concentration level signal LV=1 is set at the Step S777. Then, the decision is No at the Step S73 and the processing proceeds to the Step S75 where a coefficient for calculating the base value B(n) is switched and the base value B(n) is calculated by using a second coefficient k2 which is smaller than the first coefficient k1. Accordingly, the base value B(n) is changed more slowly than the sensor output value S(n) and maintains a value close to the base value obtained when the concentration of the specific gas is increased. Consequently, it is possible to decide a change in the concentration of the specific gas by using the base value B(n) calculated at the Step S75 as a reference to calculate the difference value D(n). In addition, in the second embodiment, it is possible to output the concentration of the specific gas for a plurality of concentration levels. In an electronic control assembly 20, it is possible to properly carry out the opening and closing operations of the flap 34 depending on the gas concentration, for example, half opening as well as full opening and full closing.

To the contrary, when the concentration of the specific gas is fully decreased so that the difference value D(n) becomes smaller, a concentration level signal LV=0 is generated at the Step S77D. Then, the decision of Yes is obtained at the Step S73 and the processing proceeds to the Step S74 where the coefficient for calculating the base value B(n) is switched and the base value B(n) is calculated by using the comparatively great first coefficient k1 again. Accordingly, the base value B(n) rapidly follows the sensor output value S(n). For this reason, even if the concentration of the specific gas is increased again, the difference value D(n) is increased again without the influence of the past fluctuation in the specific gas. Consequently, it is possible to reliably grasp the increase in the concentration of the specific gas, thereby generating a proper concentration level signal.

Figure 11:
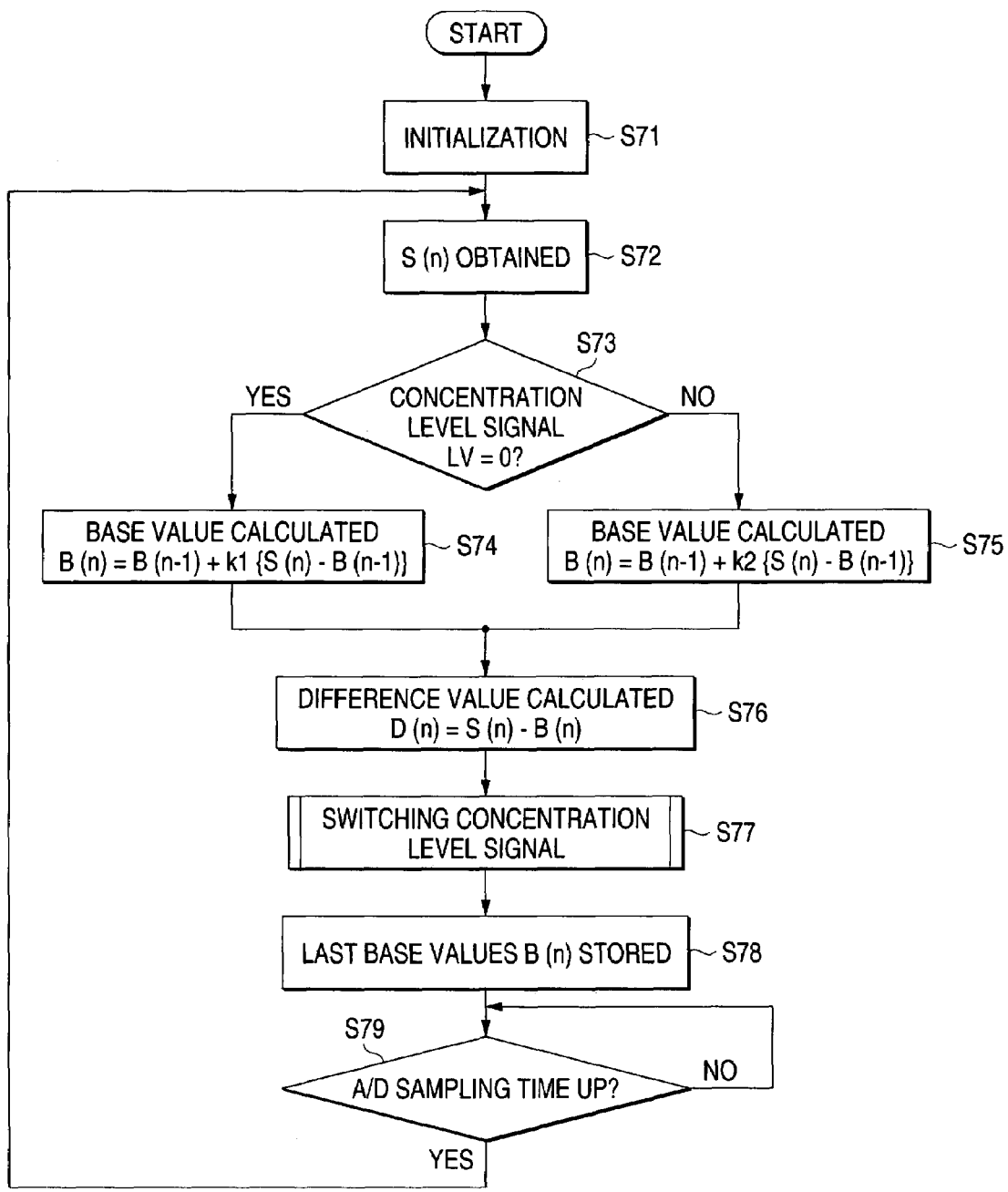
FIG. 11 is a flow chart showing a control in the microcomputer of a gas detecting device according to a second embodiment.
Figure 13:
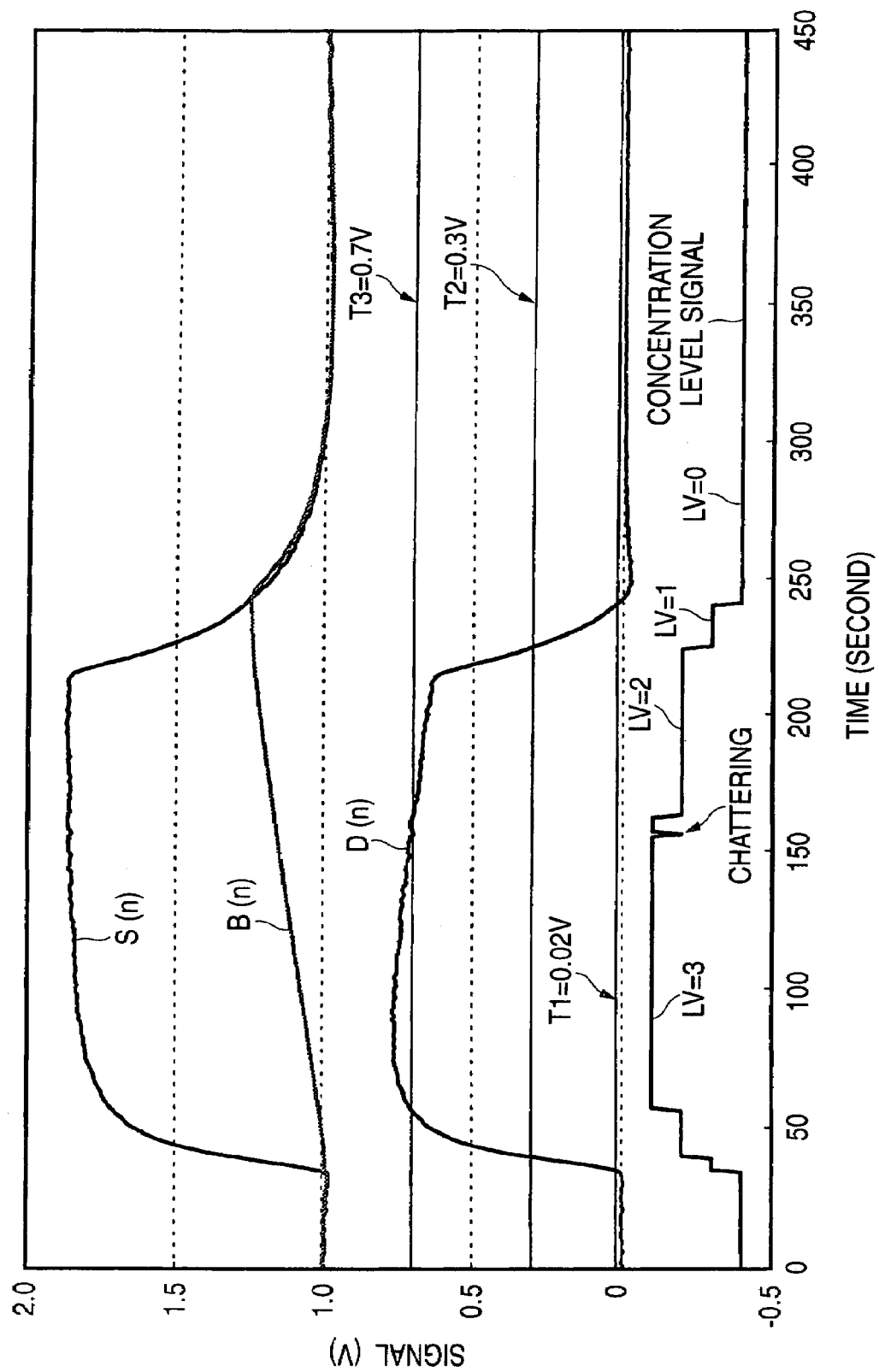
FIG. 13 is a chart showing a change in a sensor output value S(n), a base value B(n) and a difference value D(n) and a change in a concentration signal which are obtained when the concentration of NOx is increased for a certain period according to the second embodiment.

Next, FIG. 13 shows an example of a change in the sensor output value S(n), the base value B(n), the difference value D(n) and the concentration level signal LV which are obtained by the control in accordance with the flow charts of FIGS. 11 and 12 when the concentration of NOx is increased and is then reduced. Also in the example, in the same manner as the example described in the first embodiment, a gas sensor 11 is provided in a wind channel, and clean air containing no NOx is originally caused to flow at a predetermined wind velocity and air mixing the NOx in a predetermined concentration is caused to flow for a predetermined period. Description will be given to the case in which the first coefficient k1=1/16, the second coefficient k2=1/2048, the first interlevel threshold T1=0.02 V, the second interlevel threshold T2=0.3 V and the third interlevel threshold T3=0.7 V are set. For a time of 0 to approximately 35 seconds, the clean air is caused to flow and the sensor output value S(n) fluctuates by a slight noise but is maintained to have an almost constant value (approximately 1.0 V). When a rise in the NOx is started at a time of approximately 35 seconds, the sensor output value S(n) is correspondingly increased. Subsequently, it is apparent that the sensor output value S(n) is then decreased gradually for a time of approximately 240 to 300 seconds again, and is finally returned to an original level (approximately 1.0 V).

On the other hand, the base value B(n) is originally maintained to have an almost constant value while slightly fluctuating in accordance with the sensor output value S(n) for the time of 0 to approximately 35 seconds. Accordingly, the difference value D(n) is maintained to have almost 0 V. However, when the concentration of the NOx is increased at the time of approximately 35 seconds, the sensor output value S(n) is started to be increased. Consequently, the base value B(n) cannot follow completely. Therefore, when the difference value D(n) is increased to exceed the first interlevel threshold T1=0.02 V, the concentration level signal LV is changed from LV=0 to LV=1. After the next time, moreover, k2 (=1/2048) is used for calculating the base value B(n) at the Step S75. Therefore, the base value B(n) is gradually increased to slowly approximate to the sensor output value S(n). Furthermore, even if the sensor output value S(n) is increased, the base value B(n) is not greatly increased. Therefore, the difference value D(n) is further increased. Consequently, the concentration level signal LV is changed to LV=2 when the second interlevel threshold T2=0.3 V is exceeded, and furthermore, the concentration level signal LV is changed to LV=3 when the third interlevel threshold T3=0.7 V is exceeded.

Then, when the concentration of the NOx is gradually reduced and the sensor output value S(n) is decreased, the difference value D(n) is also decreased. When the difference value D(n) is less than the third interlevel threshold T3=0.7 V, it is decided that the concentration of the NOx is reduced by one rank and the concentration level signal LV is changed from LV=3 to LV=2. Furthermore, when the difference value is less than the second interlevel threshold T2=0.3 V, it is decided that the concentration of the NOx is decreased by another one rank to change the concentration level signal LV from LV=2 to LV=1.

Furthermore, when the difference value is lower than the first interlevel threshold T1=0.02 V, it is decided that the concentration of the NOx is fully reduced to change the concentration level signal LV from LV=1 to LV=0. In addition, since the base value B(n) is subsequently calculated by using the first coefficient k1 at the Step S74, it is changed in conformity to the sensor output value S(n) again. Accordingly, even if the concentration of the NOx is increased again and the sensor output value S(n) is decreased, such a situation can be detected immediately to generate a proper concentration level signal LV. In the second embodiment, the same interlevel thresholds T1, T2 and T3 are used for an interlevel threshold for increasing a concentration level by one rank and an interlevel threshold for increasing the concentration level by one rank. In the example (see FIG. 13), therefore, chattering is slightly caused.

Figure 14:
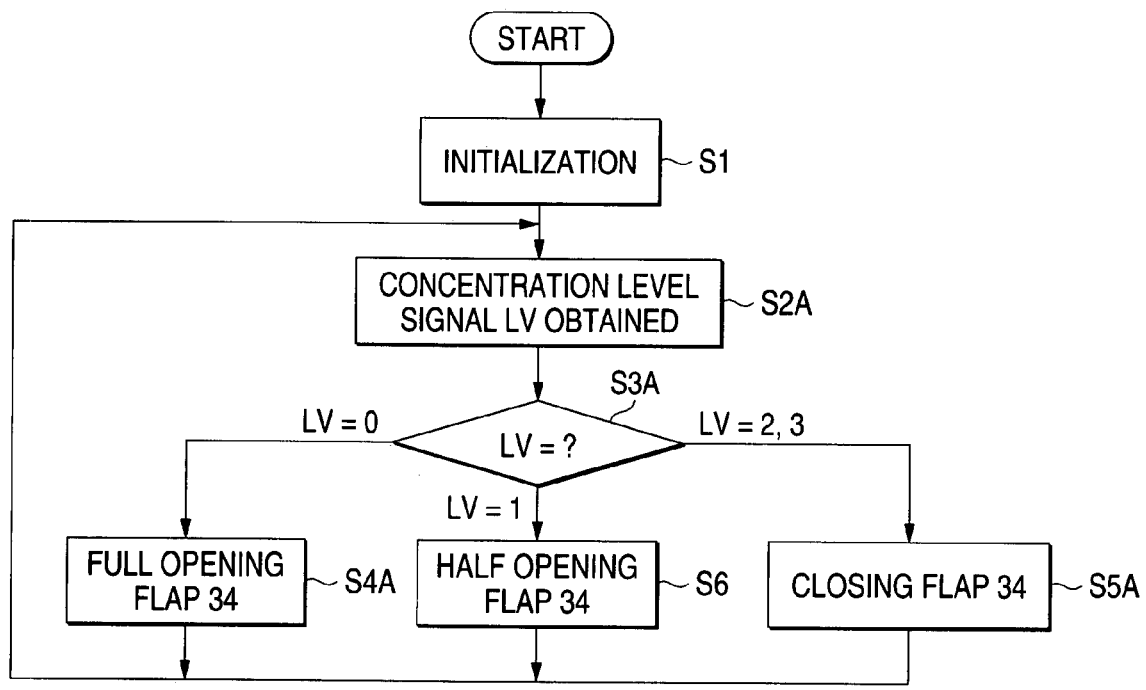
FIG. 14 is a flow chart showing a control in an autoventilation system for a vehicle according to the second embodiment.

By using the concentration level signal LV obtained by such a control, for example, the following control can be carried out for the autoventilation system 100 for a vehicle (see FIG. 1) More specifically, in a flap driving circuit 21, initialization is carried out at Step S1, a concentration level signal LV is then acquired at Step S2A and the concentration level signal LV detects a level at Step S3A as shown in a flow chart of FIG. 14. In the case in which LV=0 is obtained, that is, the concentration of the specific gas on the outside of a vehicle compartment is fully low, an instruction for fully opening the flap 34 is given at Step S4A. Consequently, the flap 34 is rotated so that a duct 33 for outside air intake is connected to a duct 31 and the outside air is taken into the vehicle compartment. On the other hand, in the case in which LV=2 or 3 is obtained, that is, the concentration of the specific gas on the outside of the vehicle compartment is very high at the Step S3A, an instruction for fully closing the flap 34 is given at Step S5A. Consequently, the flap 34 is rotated and a duct 32 for inside air intake is connected to the duct 31 so that outside air introduction is blocked and inside air circulation is carried out. At the Step S3A, furthermore, if LV=1 is obtained, that is, the concentration of the specific gas is slightly high, an instruction for half opening the flap

34 is given at Step S6. Consequently, the introduction of the outside air is slightly restricted and the inside air circulation is also carried out.

Furthermore, while the flap 34 is fully closed with LV=2 and 3 as described above, each concentration level signal and the opening of the flap 34 may correspond to each other with one to one, for example, the flap 34 is opened by a quarter with LV=2 and is fully closed with LV=3. To the contrary, the flap 34 can also be controlled to be fully opened with LV=0 and to be fully closed with LV=1, 2 and 3.

While a second coefficient k2=0 has not been described in the second embodiment, a change in the concentration of a reducing gas can also be measured with k2=0 in the same manner as in the first embodiment. As described in the first embodiment, in some cases in which a drift is generated toward the side on which a sensor resistance value Rs of the gas sensor element 11 is increased by the influence of a change in an environment or the like, the concentration level signal of LV=0 cannot be generated even if the concentration of the oxidizing gas component is fully reduced. Therefore, it is preferable that k2>0 should be set as described above.

(Fourth Variant)

A variant of the second embodiment will be described. In a fourth variant, a processing flow in a μC16 has four kinds of concentration level signals LV (LV=0, 1, 2, 3) corresponding to three or more concentration levels, more specifically, four concentration levels and three interlevel thresholds T1, T2 and T3 (T1<T2<T3) for dividing these concentration levels in the same manner as in the second embodiment. In the same manner as in the first variant, there are provided a gas detecting device 40 and an autoventilation system 140 for a vehicle comprising the gas detecting device 40. More specifically, the system serves to detect a change in the concentration of a reducing gas component such as CO and for opening and closing a flap based thereon differently from the second embodiment. Accordingly, different portions will be mainly described, and the same portions have the same symbols and numbers and description will be omitted or simplified.

A control in the μC16 according to the fourth variant will be described in accordance with a flow chart of FIG. 15. Steps S71 to S73 are the same as those in the second embodiment, and the processing proceeds to Step S85 if a decision is No, that is, LV=1, 2 or 3 is obtained at the Step S73. On the other hand, if the decision is Yes, that is, a signal of LV=0 is generated, the processing proceeds to Step S84.

At the Step S84, a base value B(n) is calculated based on a third coefficient k3 and the processing proceeds to Step S86. On the other hand, at the Step S85, the base value B(n) is calculated based on a fourth coefficient k4 and the processing proceeds to Step S86. The base value B(n) has a degree of follow-up for a sensor output value S(n) varied depending on the coefficients k3 and k4 to be used.

Since a processing in a subroutine of Step S77 (see FIG. 12) is the same as that in the second embodiment, description will be omitted. Subsequently, last base values B(n) calculated at the Steps S84 and S85 are stored at Step S78 and the time up of an A/D sampling time is waited at Step S79, and furthermore, the processing returns to the Step S72.

Figure 15:
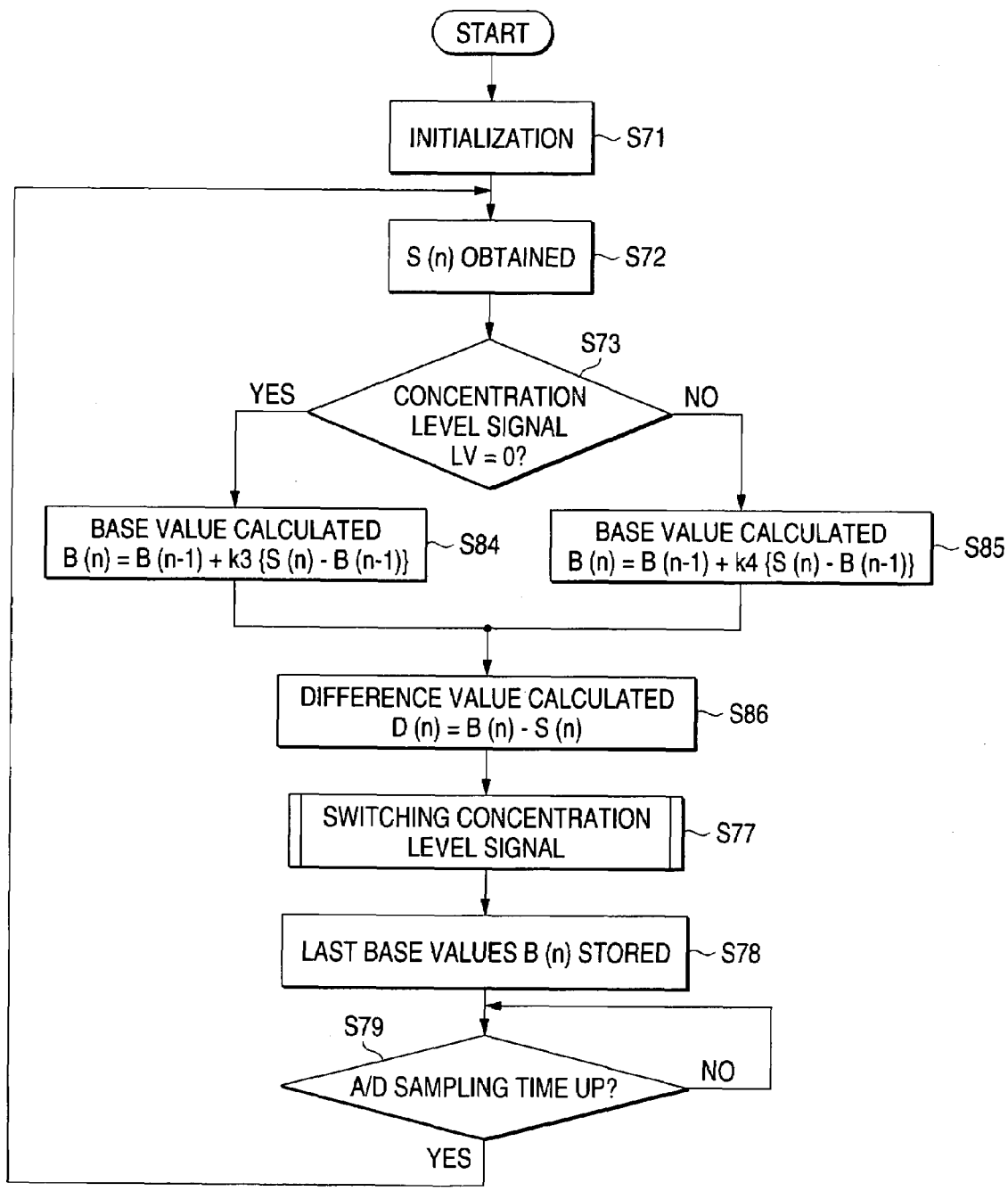
FIG. 15 is a flow chart showing a control in the microcomputer of a gas detecting device according to a fourth variant.
Figure 16:
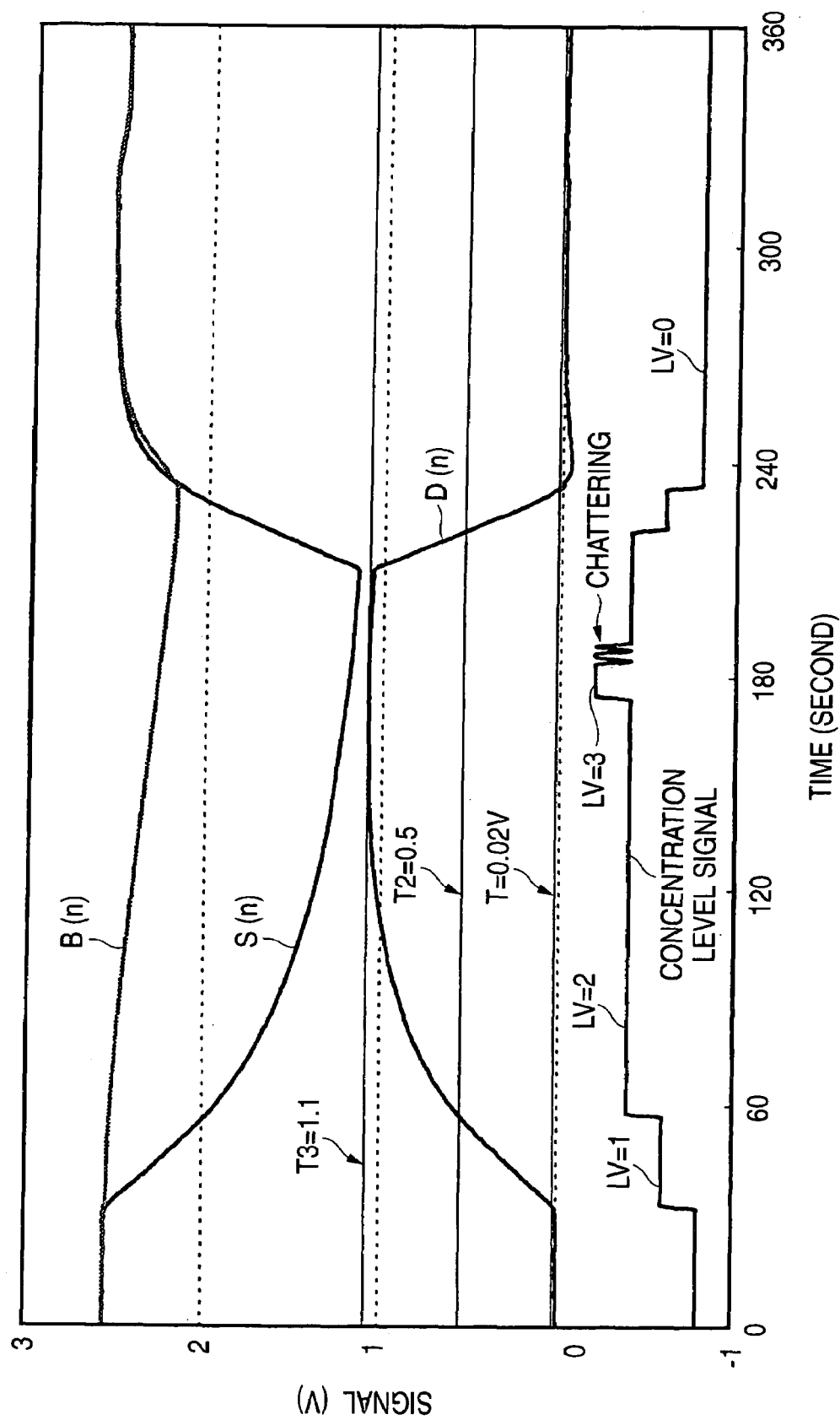
FIG. 16 is a chart showing a change in a sensor output value S(n), a base value B(n) and a difference value D(n) and a change in a concentration signal which are obtained when the concentration of CO is increased for a certain period according to the fourth variant.

Next, FIG. 16 shows an example of a change in the sensor output value S(n), the base value B(n), a difference value D(n) and the concentration level signal LV which are obtained by the control in accordance with the flow charts of FIGS. 15 and 12 when the concentration of CO is increased and is then reduced also in the fourth variant. Also in the example, in the same manner as the example described in the first variant, a gas sensor 41 is provided in a wind channel and clean air containing no CO is originally caused to flow at a predetermined wind velocity and air mixing the CO in a predetermined concentration is then caused to flow for a predetermined period. Description will be given to the case in which the third coefficient k3=1/16, the fourth coefficient k4=1/1920, the first interlevel threshold T1=0.02 V, the second interlevel threshold T2=0.5 V and the third interlevel threshold T3=1.1 V are set. For a time of 0 to approximately 35 seconds, the clean air is caused to flow and the sensor output value S(n) fluctuates by a slight noise but is maintained to have an almost constant value (approximately 2.5 V). When a rise in the CO is started at the time of approximately 35 seconds, the sensor output value S(n) is correspondingly decreased. Subsequently, it is apparent that the sensor output value S(n) is then increased gradually for a time of approximately 210 to 265 seconds again, and is finally returned to an original level (approximately 2.5 V).

On the other hand, the base value B(n) is originally maintained to have an almost constant value while slightly fluctuating in accordance with the sensor output value S(n) for the time of 0 to approximately 35 seconds. Accordingly, the difference value D(n) is maintained to have almost 0 V. However, when the concentration of the CO is increased at the time of approximately 35 seconds, the sensor output value S(n) is started to be increased. Consequently, the base value B(n) cannot follow completely. Therefore, when the difference value D(n) is increased to exceed the first interlevel threshold T1=0.02 V, the concentration level signal LV is changed from LV=0 to LV=1. After the next time, moreover, k4 (=1/1920) is used for calculating the base value B(n) at the Step S85. Therefore, the base value B(n) is gradually decreased to slowly approximate to the sensor output value S(n). Furthermore, even if the sensor output value S(n) is decreased, the base value B(n) is not greatly decreased. Therefore, the difference value D(n) is further increased. Consequently, the concentration level signal LV is changed to LV=2 when the second interlevel threshold T2=0.5 V is exceeded, and furthermore, the concentration level signal LV is changed to LV=3 when the third interlevel threshold T3=1.1 V is exceeded.

Then, when the concentration of the CO is gradually reduced and the sensor output value S(n) is increased, the difference value D(n) is also decreased. When the difference value is less than the third interlevel threshold T3=1.1 V, it is decided that the concentration of the CO is reduced by one rank and the concentration level signal LV is changed from LV=3 to LV=2. Furthermore, when the difference value is less than the second interlevel threshold T2=0.5 V, it is decided that the concentration of the CO is reduced by another one rank to change the concentration level signal LV from LV=2 to LV=1. Furthermore, when the difference value is lower than the first interlevel threshold T1=0.02 V, it is decided that the concentration of the CO is fully reduced to change the concentration level signal LV from LV=1 to LV=0. In addition, since the base value B(n) is subsequently calculated by using the third coefficient k3 at the Step S84, it is changed in conformity to the sensor output value S(n). Accordingly, even if the concentration of the CO is increased again and the sensor output value S(n) is decreased, such a situation can be detected immediately to generate a proper concentration level signal LV. Also in the fourth variant, the same interlevel thresholds T1, T2 and T3 are used for an interlevel threshold for increasing a concentration level by one rank and an interlevel threshold for increasing the concentration level by one rank. In the example (see FIG. 16), therefore, chattering is slightly caused.

By such a control, similarly, it is possible to give an instruction for the opening of a flap 34 in a flap driving circuit 21 and to properly control outside air introduction and inside air circulation by using the concentration level signal LV thus obtained in the autoventilation system 140 for a vehicle (see FIG. 6) in the same manner as in the second embodiment (see FIG. 14).

While the fourth coefficient k4=0 has not been described also in the fourth variant, a change in the concentration of a reducing gas can also be measured with k4=0 in the same manner as in the first variant. In some cases in which a drift is generated toward the side on which a sensor resistance value Rs is decreased, the concentration level signal of LV=0 cannot be generated even if the concentration of the reducing gas component is fully reduced. Therefore, it is preferable that k4>0 should be set as described above.

(Fifth and Sixth Variants)

In the second embodiment and the fourth variant, the concentration level signal LV is varied by only one rank in the subroutine of the Step S77 (see FIG. 12). However, the concentration level signal LV can also be changed by a plurality of ranks at a time such that the concentration level signal LV can be selected according to the difference value D(n). More specifically, in a gas detecting device 10 and an autoventilation system 100 for a vehicle comprising the gas detecting device 10 according to a fifth variant, only a subroutine of Step S77 in a processing flow is different from that of the second embodiment and the contents of the subroutine in the Step S77 will be therefore described with reference to FIG. 17.

When the difference value D(n) is calculated at Step S76 and the processing proceeds to the Step S77 (see FIG. 11), it is first decided whether the currently generated concentration level signal LV is set to LV=0 corresponding to the lowest concentration level at Step S91. If the decision is Yes, that is, LV=0 is obtained, the processing proceeds to Step S94. On the other hand, the decision is No, that is, LV=1, 2 or 3 is obtained, the processing proceeds to Step S92. At the Step S92, it is decided whether or not the currently generated concentration level signal LV is set to LV=1 corresponding to a second lowest concentration level. If the decision is Yes, that is, LV=1 is obtained, the processing proceeds to Step S95. On the other hand, the decision is No, that is, LV=2 or 3 is obtained, the processing proceeds to Step S93. At the Step S93, furthermore, it is decided whether or not the currently generated concentration level signal LV is set to LV=2 corresponding to a third lowest concentration level. If the decision is Yes, that is, LV=2 is obtained, the processing proceeds to Step S96. On the other hand, the decision is No, that is, LV=3 corresponding to the highest concentration level is obtained, the processing proceeds to Step S97. Thus, it is possible to classify the current concentration level, that is, the generated concentration level signal LV for each case.

At the Step S94, it is decided whether or not the difference value D(n) is greater than a first concentration interlevel threshold T1. If the decision is No, that is, D(n)≦T1 is obtained, the processing proceeds to Step S9A. On the other hand, when the decision is Yes, that is, D(n)≦T1, the processing proceeds to the Step S95. At the Step S95, moreover, it is decided whether or not the difference value D(n) is greater than a second concentration interlevel threshold T2. When the decision is No, that is, D(n)≦T2 is obtained, the processing proceeds to Step S99. On the other hand, when the decision is Yes, that is, D(n)>T2 is obtained, the processing proceeds to the Step S96. At the Step S96, furthermore, it is decided whether or not the difference value D(n) is greater than a third concentration interlevel threshold T3. If the decision is No, that is, D(n)≦T3 is obtained, the processing proceeds to Step S98. On the other hand, when the decision is Yes, that is, D(n)>T3 is obtained, the processing proceeds to Step S9E.

On the other hand, at the Step S97, it is decided whether or not the difference value D(n) is smaller than the third concentration interlevel threshold T3. If the decision is No, that is, D(n)≧T3 is obtained, the processing proceeds to the Step S9E. On the other hand, when the decision is Yes, that is, D(n)<T3 is obtained, the processing proceeds to the Step S98. At the Step S98, moreover, it is decided whether or not the difference value D(n) is smaller than the second concentration interlevel threshold T2. When the decision is No, that is, D(n)≧T2 is obtained, the processing proceeds to Step S9D. On the other hand, when the decision is Yes, that is, D(n)<T2 is obtained, the processing proceeds to the Step S99. At the Step S99, furthermore, it is decided whether or not the difference value D(n) is smaller than the first concentration interlevel threshold T1. If the decision is No, that is, D(n)≧T1 is obtained, the processing proceeds to Step S9B. On the other hand, when the decision is Yes, that is, D(n)<T3 is obtained, the processing proceeds to the Step S9A. Consequently, the classification for each case can be carried out depending on the difference value D(n) irrespective of the current concentration level.

At the Step S9A, the concentration level signal is set to LV=0 or LV=0 is maintained. At the Step S9B, moreover, the concentration level signal is set to LV=1 or LV=1 is maintained. At the Step S9D, the concentration level signal is set to LV=2 or LV=2 is maintained. At the Step S9E, the concentration level signal is set to LV=3 or LV=3 is maintained. As described above, the classification for each case is carried out depending on the difference value D(n) irrespective of the current concentration level so that a concentration level signal corresponding to the difference value D(n) can be generated. Accordingly, in the case in which the difference value D(n) is rapidly increased or decreased, the concentration level signal LV might be changed by a plurality of ranks at a time.

Figure 17:
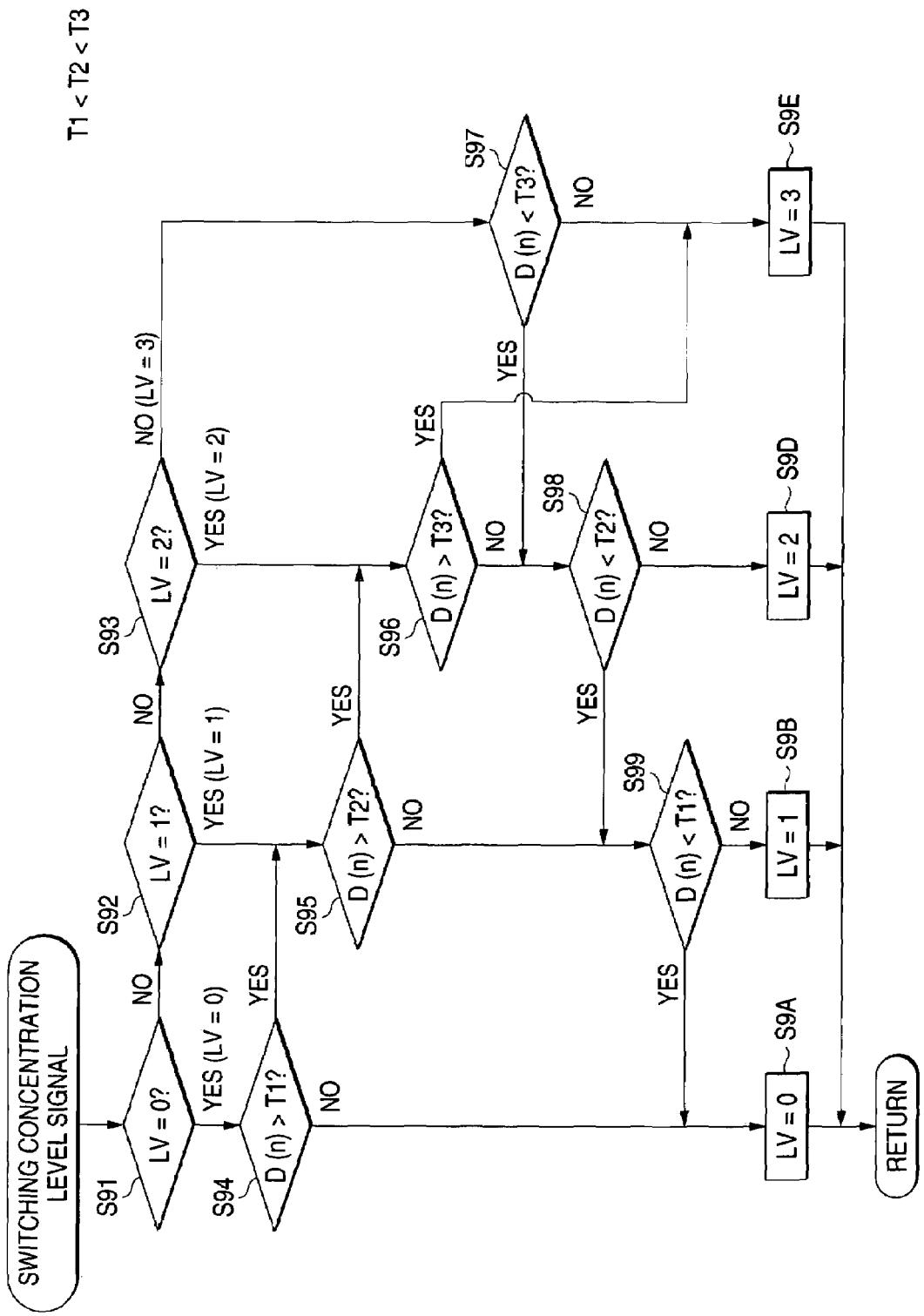
FIG. 17 is a flow chart showing the contents of a subroutine for concentration level signal switching generation in the control flow according to fifth and sixth variants.

In the fifth variant, FIG. 17 shows the contents of the subroutine in the Step S77 of the processing flow in the gas detecting device 10 and the autoventilation system 100 for a vehicle comprising the gas detecting device 10 according to the second embodiment. In the same manner, however, the contents of the subroutine in the Step S77 shown in FIG. 17 may be applied as a sixth variant in the gas detecting device 40 and the autoventilation system 140 for a vehicle comprising the gas detecting device 40 according to the fourth variant.

(Seventh and Eighth Variants)

Figure 18:
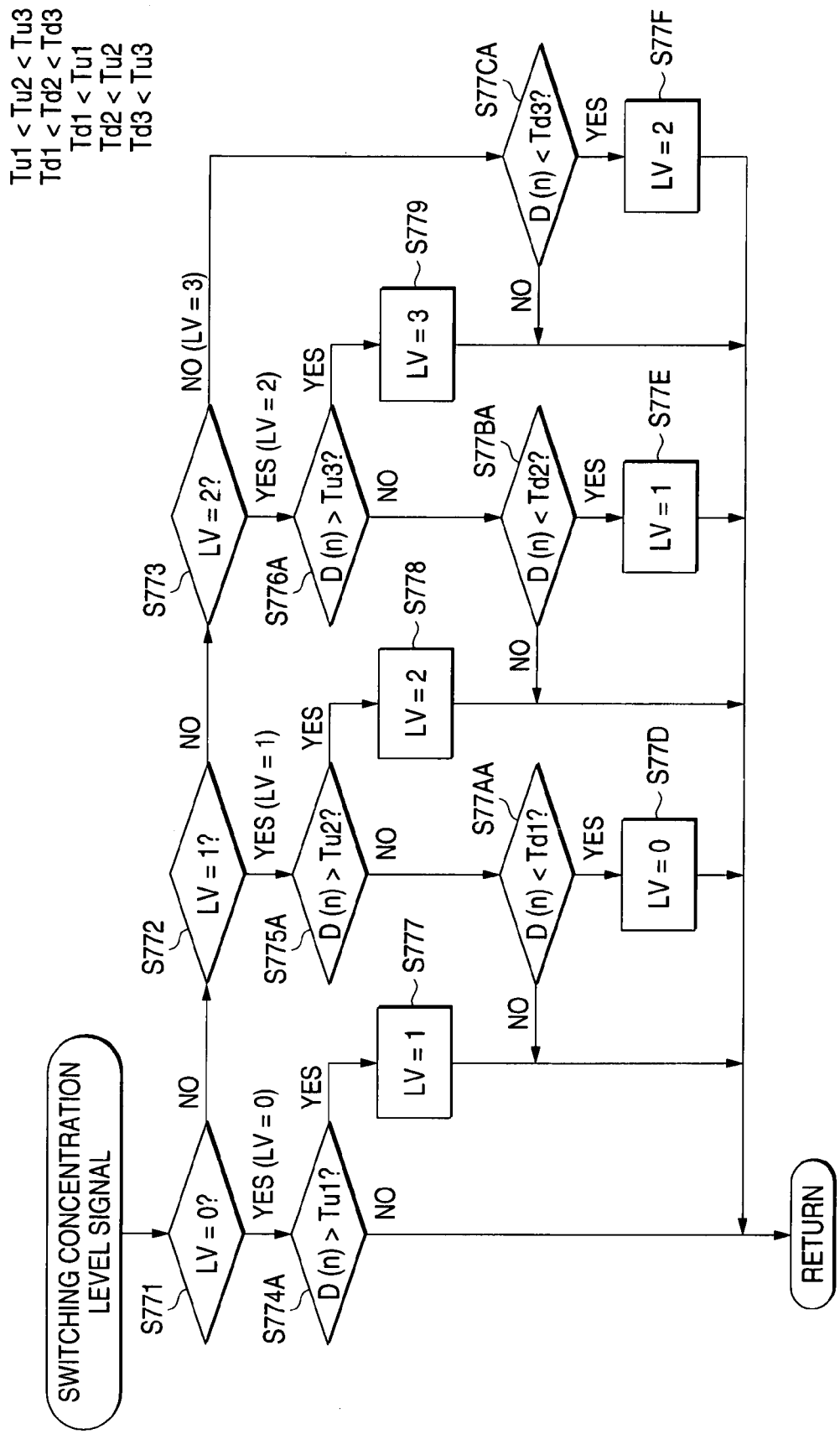
FIG. 18 is a flow chart showing the contents of a subroutine for concentration level signal switching generation in the control flow according to seventh and eighth variants.

In the second embodiment and the fourth variant, the same interlevel thresholds T1, T2 and T3 are used for an interlevel threshold for increasing a concentration level by one rank and an interlevel threshold for decreasing the concentration level by one rank. On the other hand, it is preferable that each interlevel threshold should have a hysteresis. In other words, it is preferable that a level-up threshold and a level-down threshold which is smaller than the corresponding level-up threshold should be selected as a threshold for increasing a level and a threshold for decreasing a level which is smaller, respectively. More specifically, in the seventh variant, the interlevel thresholds T1, T2 and T3 are replaced with level-up thresholds Tu1, Tu2 and Tu3 or level-down thresholds Td1, Td2 and Td3 respectively in the contents of the subroutine in the Step S77 of the processing flow as shown in FIG. 18 in the gas detecting device 10 and the autoventilation system 100 for a vehicle comprising the gas detecting device 10 according to the second embodiment (see FIG. 1). The contents of the subroutine in the Step S77 will be described with reference to FIG. 18. The level-up thresholds Tu1, Tu2 and Tu3 and the level-down thresholds Td1, Td2 and Td3 have the relationships of Tu1<Tu2<Tu3, Td1<Td2<Td3, Td1<Tu1, Td2<Tu2 and Td3<Tu3, respectively.

In the same manner as in the second embodiment, when the difference value D(n) is calculated at Step S76 and the processing proceeds to the Step S77 (see FIG. 11) where it is first decided whether or not a currently generated concentration level signal LV is set to LV=0 corresponding to the lowest concentration at Step S771. If the decision is Yes, that is, LV=0 is obtained, the processing proceeds to Step S774A. On the other hand, the decision is No, that is, LV=1, 2 or 3 is obtained, the processing proceeds to Step S772. At the Step S772, it is decided whether or not the currently generated concentration level signal LV is set to LV=1. If the decision is Yes, the processing proceeds to Step S775A. On the other hand, the decision is No, the processing proceeds to Step S773. At the Step S773, furthermore, it is decided whether or not the currently generated concentration level signal LV is set to LV=2. If the decision is Yes, the processing proceeds to Step S776A. On the other hand, the decision is No, that is, LV=3 is obtained, the processing proceeds to Step S77CA. Thus, it impossible to classify the current concentration level, that is, the generated concentration level signal LV for each case.

At the Step S774A, it is decided whether or not the difference value D(n) is greater than the first level-up threshold Tu1. If the decision is No, that is, D(n)≦Tu1 is obtained, it is not necessary to carry out a change from the lowest concentration level to a higher concentration level. Therefore, the processing passes through the subroutine and returns to a main routine. On the other hand, when the decision is Yes, that is, D(n)>Tu1, the processing proceeds to Step S777 where the concentration level signal LV is set to LV=1 which is higher by one rank and the processing then returns to the main routine. More specifically, the duty ratio of a PWM signal is changed from 15% to 30% and the processing then returns to the main routine. At the Step S775A, moreover, it is decided whether or not the difference value D(n) is greater than the second level-up threshold Tu2. When the decision is No, that is, D(n)≦Tu2 is obtained, the processing proceeds to Step S77AA. On the other hand, when the decision is Yes, that is, D(n)>Tu2 is obtained, the processing proceeds to Step S778 where the concentration level signal LV is set to LV=2 which is higher than a current level by one rank and the processing then returns to the main routine. More specifically, the duty ratio of the PWM signal is changed from 30% to 50% and the processing then returns to the main routine. At the Step S776A, furthermore, it is decided whether or not the difference value D(n) is greater than the third level-up threshold Tu3. If the decision is No, that is, D(n)≦Tu3 is obtained, the processing proceeds to Step S77BA. On the other hand, when the decision is Yes, that is, D(n)>Tu3 is obtained, the processing proceeds to Step S779 where the concentration level signal LV is set to LV=3 which is higher than the current level by one rank and the processing then returns to the main routine. More specifically, the duty ratio of the PWM signal is changed from 50% to 70% and the processing then returns to the main routine. At the Steps 774A, 775A and 776A, thus, a comparison with the level-up thresholds Tu1, Tu2 and Tu3 is carried out in place of the interlevel thresholds T1, T2 and T3.

At the Step S77AA, it is decided whether or not the difference value D(n) is smaller than the first level-down threshold Td1. If the decision is No, that is, D(n)>Td1 is obtained, it is not necessary to decrease the rank of the current concentration level. Therefore, the processing passes through the subroutine and returns to the main routine. On the other hand, when the decision is Yes, that is, D(n)<Td1 is obtained, the processing proceeds to Step S77D where the concentration level signal LV is set to LV=0 which is lower by one rank and the processing then returns to the main routine. More specifically, the duty ratio of the PWM signal is changed from 30% to 15% and the processing then returns to the main routine. At the Step S77BA, moreover, it is decided whether or not the difference value D(n) is smaller than the second level-down threshold Td2. When the decision is No, that is, D(n)≧Td2 is obtained, the processing returns to the main routine because it is not necessary to decrease the rank of the current concentration level. On the other hand, when the decision is Yes, that is, D(n)<Td2 is obtained, the processing proceeds to Step S77E where the concentration level signal LV is set to LV=1 which is lower than the current level by one rank and the processing then returns to the main routine. More specifically, the duty ratio of the PWM signal is changed from 50% to 30% and the processing then returns to the main routine. At the Step S77CA, furthermore, it is decided whether or not the difference value D(n) is smaller than the third level-down threshold Td3. If the decision is No, that is, D(n)≧Td3 is obtained, the processing returns to the main routine because it is not necessary to decrease the rank of the current concentration level. On the other hand, when the decision is Yes, that is, D(n)<Td3 is obtained, the processing proceeds to Step S77F where the concentration level signal LV is set to LV=2 which is lower than the current level by one rank and the processing then returns to the main routine. More specifically, the duty ratio of the PWM signal is changed from 70% to 50% and the processing then returns to the main routine. At the Steps 77AA, 77BA and 77CA, thus, a comparison with the level-down thresholds Td1, Td2 and Td3 is carried out in place of the interlevel thresholds T1, T2 and T3.

Then, the last base values B(n) calculated at the Steps S74 and S75 are stored at Step S78 and the time up of an A/D sampling time is waited at Step S79, and the routine then returns to the Step S72 (see FIG. 11).

In the same manner as in the second embodiment, thus, when the concentration of a specific gas is increased so that the difference value D(n) becomes greater to exceed the first interlevel threshold Tu1, the base value B(n) is calculated by using a comparatively small second coefficient k2. Accordingly, the base value B(n) is changed more slowly than the sensor output value S(n), and it is supposed that the base value B(n) thus calculated holds the past state in which the concentration of the specific gas is comparatively low. Consequently, it is possible to decide a change in the concentration of the specific gas by using the base value B(n) as a reference to calculate the difference value D(n). Also in the seventh variant, moreover, it is possible to output the concentration of the specific gas for a plurality of concentration levels. In an electronic control assembly 20, consequently, it is possible to properly carry out the opening and closing operations of a flap 34 depending on the gas concentration, for example, half opening as well as full opening and full closing.

Furthermore, since the level-up threshold Tu1 for increasing the concentration level by one rank is different from the level-down threshold Td1 for decreasing the concentration level by one rank as described above, it is possible to solve a problem in that the concentration level is changed with a slight fluctuation when the difference value D(n) approximates to a threshold, that is, to prevent chattering in which the concentration level signal LV is often changed, which is preferable.

Figure 19:
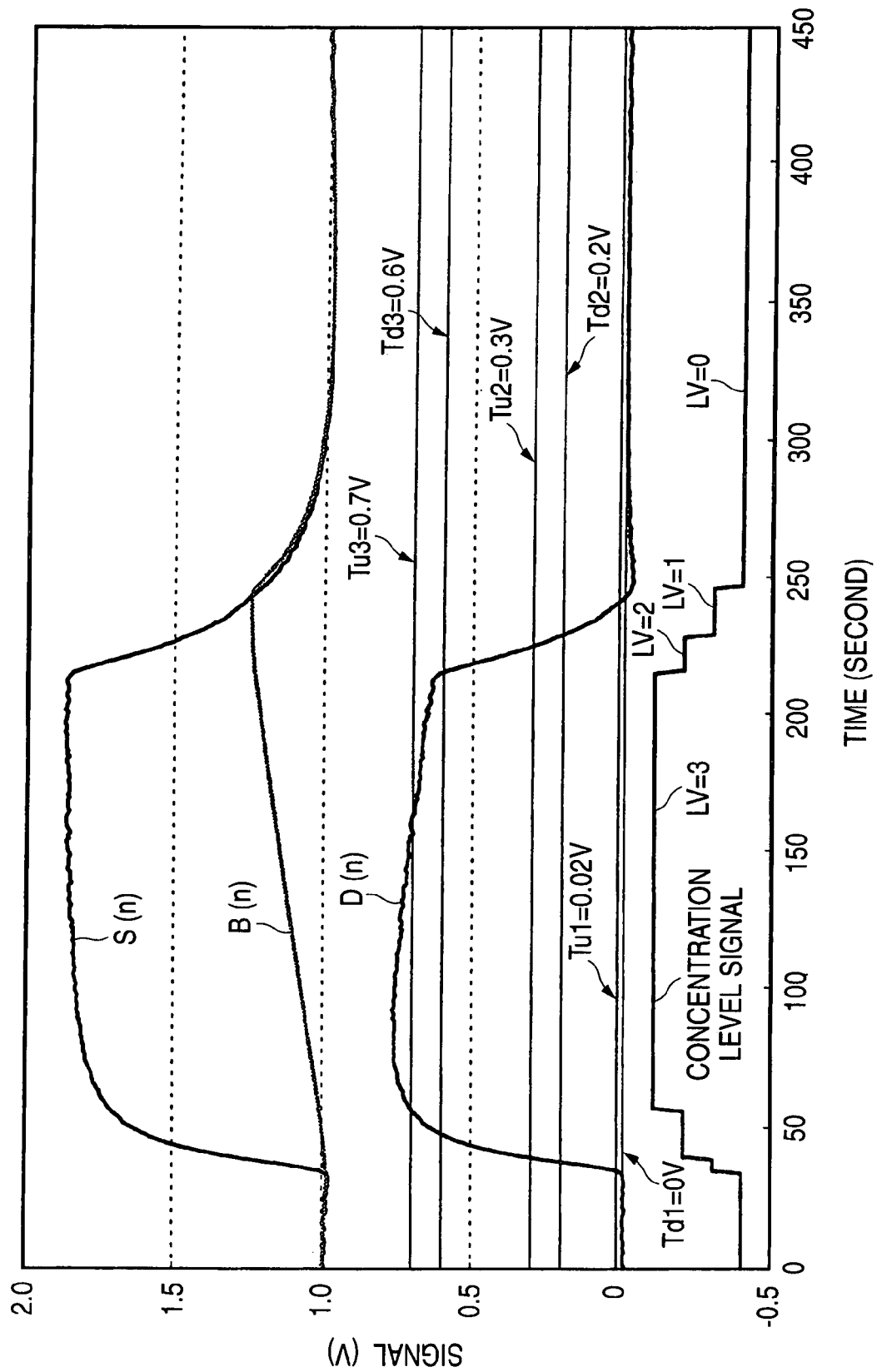
FIG. 19 is a chart showing a change in a sensor output value S(n), a base value B(n) and a difference value D(n) and a change in a concentration signal which are obtained when the concentration of NOx is increased for a certain period according to the seventh variant.

Next, FIG. 19 shows an example of a change in the sensor output value S(n), the base value B(n), the difference value D(n) and the concentration level signal LV which are obtained by the control in accordance with the seventh variant, that is, the flow charts of FIGS. 11 and 18 when the concentration of NOx is increased and is then reduced. In the example, a data processing in accordance with the flow chart shown in FIG. 18 is carried out by using the same data as those described in the second embodiment. Accordingly, the first coefficient k1=1/16 and the second coefficient k2=1/2048 are set. Moreover, the first level-up threshold Tu1=0.02 V, the second level-up threshold Tu2=0.3 V, the third level-up threshold Tu3=0.7 V, the first level-down threshold Tu1=0 V, the second level-down threshold Tu2=0.2 V, and the third level-down threshold Tu3=0.6 V are set.

While the chattering is generated at a time of approximately 150 seconds in the concentration level signal LV according to the second embodiment shown in FIG. 13, the chattering is not generated in the example of FIG. 19. Thus, since the level-up threshold and the level-down threshold are used to have the hysteresis, it is apparent that the chattering can be prevented in the seventh variant.

In the seventh variant, FIG. 18 shows the contents of the subroutine in the Step S77 of the processing flow in the gas detecting device 10 and the autoventilation system 100 for a vehicle comprising the gas detecting device 10 according to the second embodiment. In the same manner, however, the contents of the subroutine in the Step S77 shown in FIG. 18 may be applied as an eighth variant in the gas detecting device 40 and the autoventilation system 140 for a vehicle comprising the gas detecting device 40 according to the fourth variant.

(Ninth and Tenth Variants)

Figure 20:
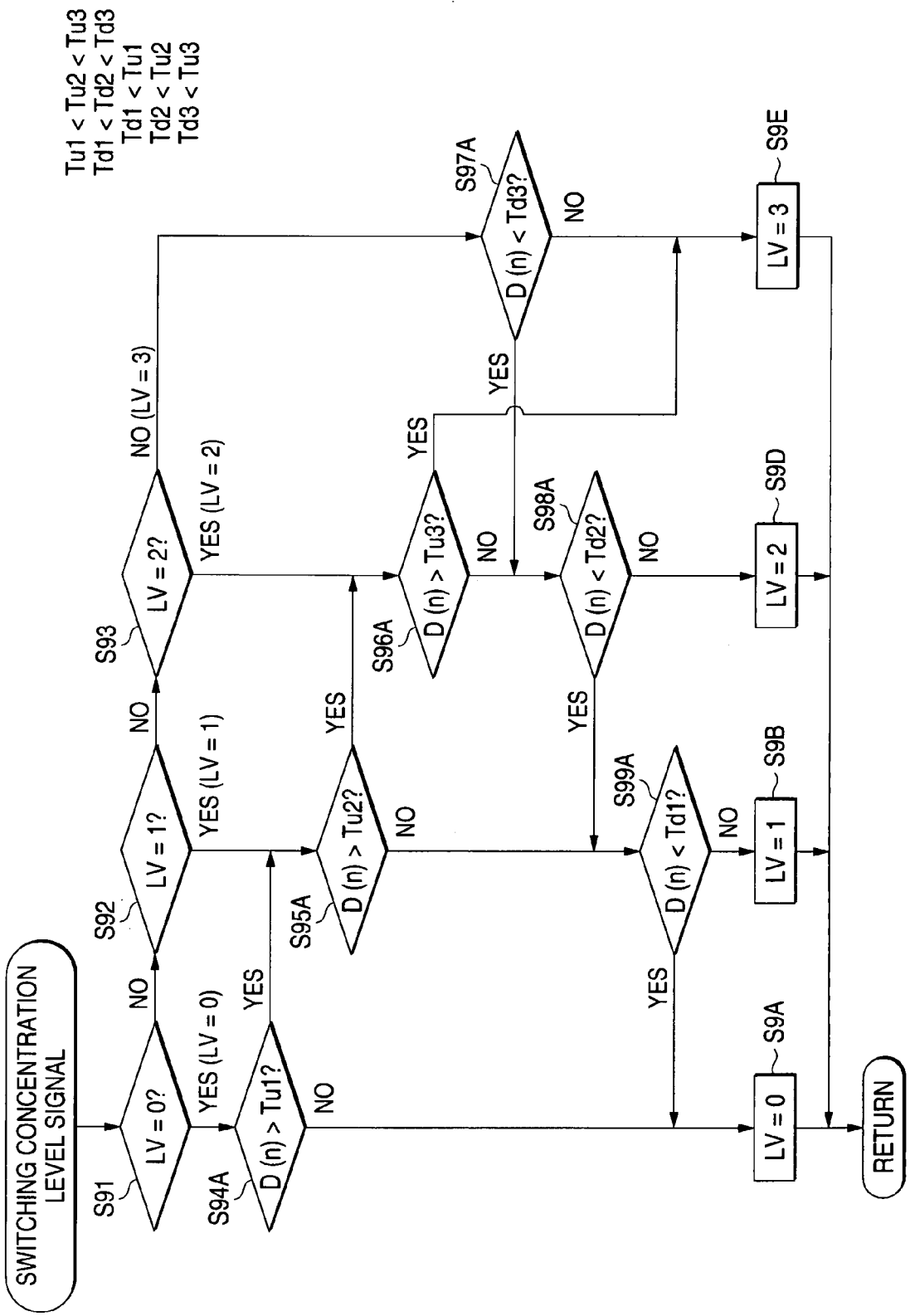
FIG. 20 is a flow chart showing the contents of a subroutine for concentration level signal switching generation in the control flow according to ninth and tenth variants.

Also in the fifth variant and the sixth variant, the same interlevel thresholds T1, T2 and T3 are used for an interlevel threshold for increasing a concentration level and an interlevel threshold for decreasing the concentration level (see FIG. 17). On the other hand, in the same manner as in the seventh and eighth variants, it is preferable that each interlevel threshold should have a hysteresis. In other words, it is preferable that a level-up threshold and a level-down threshold which is smaller than the corresponding level-up threshold should be selected as a threshold for increasing a level and a threshold for decreasing a level which is smaller, respectively. More specifically, in the ninth variant, interlevel thresholds T1, T2 and T3 are replaced with level-up thresholds Tu1, Tu2 and Tu3 or level-down thresholds Td1, Td2 and Td3 respectively in the contents of the subroutine in the Step S77 of the processing flow as shown in FIG. 20 in the gas detecting device 10 and the autoventilation system 100 for a vehicle comprising the gas detecting device 10 according to the second embodiment. The contents of the subroutine in the Step S77 will be described with reference to FIG. 20. The level-up thresholds Tu1, Tu2 and Tu3 and the level-down thresholds Td1, Td2 and Td3 have the relationships of Tu1<Tu2<Tu3, Td1<Td2<Td3, Td1<Tu1, Td2<Tu2 and Td3<Tu3, respectively.

In the same manner as in the second embodiment and the fifth variant, the difference value D(n) is calculated at Step S76 and the processing proceeds to the Step S77 (see FIG. 11) where it is first decided whether a currently generated concentration level signal LV is set to LV=0 at Step S91. If the decision is Yes, the processing proceeds to Step S94A. On the other hand, the decision is No, the processing proceeds to Step S92. At the Step S92, it is decided whether or not the currently generated concentration level signal LV is set to LV=1. If the decision is Yes, that is, LV=1 is obtained, the processing proceeds to Step S95A. On the other hand, the decision is No, the processing proceeds to Step S93. At the Step S93, furthermore, it is decided whether or not the currently generated concentration level signal LV is set to LV=2. If the decision is Yes, the processing proceeds to Step S96A. On the other hand, the decision is No, that is, LV=3 is obtained, the processing proceeds to Step S97A. In the same manner as in the fourth variant, thus, it is possible to classify the current concentration level, that is, the generated concentration level signal LV for each case.

At the Step S94A, next, it is decided whether or not the difference value D(n) is greater than the first level-up threshold Tu1. If the decision is No, that is, D(n)≦Tu1 is obtained, the processing proceeds to Step S9A. On the other hand, when the decision is Yes, that is, D(n)>Tu1 is obtained, the processing proceeds to Step S95A. At the Step S95A, moreover, it is decided whether or not the difference value D(n) is greater than the second level-up threshold Tu2. When the decision is No, that is, D(n)≦Tu2 is obtained, the processing proceeds to Step S99A. On the other hand, when the decision is Yes, that is, D(n)<Tu2 is obtained, the processing proceeds to the Step S96A. At the Step S96A, furthermore, it is decided whether or not the difference value D(n) is greater than the third level-up threshold Tu3. If the decision is No, that is, D(n)≦Tu3 is obtained, the processing proceeds to Step S98A. On the other hand, when the decision is Yes, that is, D(n)>Tu3 is obtained, the processing proceeds to Step S9E.

On the other hand, at the Step S97A, it is decided whether or not the difference value D(n) is smaller than the third level-down threshold Td3. If the decision is No, that is, D(n)≧Td3 is obtained, the processing proceeds to Step S9E. On the other hand, when the decision is Yes, that is, D(n)<Td3 is obtained, the processing proceeds to the Step S98A. At the Step S98A, moreover, it is decided whether or not the difference value D(n) is smaller than the second level-down threshold Td2. When the decision is No, that is, D(n)≧Td2 is obtained, the processing proceeds to Step S9D. On the other hand, when the decision is Yes, that is, D(n)<Td2 is obtained, the processing proceeds to the Step S99A. At the Step S99A, furthermore, it is decided whether or not the difference value D(n) is smaller than the first level-down threshold Td1. If the decision is No, that is, D(n)≧Td1 is obtained, the processing proceeds to Step S9B. On the other hand, when the decision is Yes, that is, D(n)<Td1 is obtained, the processing proceeds to the Step S9A. Also in the ninth variant, consequently, the classification for each case can be carried out depending on the difference value D(n) irrespective of the current concentration level.

At the Step S9A, the concentration level signal is set to LV=0 or LV=0 is maintained. At the Step S9B, moreover, the concentration level signal is set to LV=1 or LV=1 is maintained. At the Step S9D, the concentration level signal is set to LV=2 or LV=2 is maintained. At the Step S9E, the concentration level signal is set to LV=3 or LV=3 is maintained. As described above, also in the ninth embodiment, the classification for case is carried out depending on the difference value D(n) irrespective of the current concentration level so that a concentration level signal corresponding to the difference value D(n) can be generated in the same manner as in the fifth variant. Furthermore, since the level-up threshold and the level-down threshold are used in the ninth variant, the chattering of the concentration level signal can be prevented during the change of the concentration level.

In the ninth variant, FIG. 20 shows the contents of the subroutine in the Step S77 of the processing flow in the gas detecting device 10 and the autoventilation system 100 for a vehicle comprising the gas detecting device 10 according to the fifth variant, that is, the second embodiment. In the same manner, however, the contents of the subroutine in the Step S77 shown in FIG. 20 may be applied as a tenth variant in the gas detecting device 40 and the autoventilation system 140 for a vehicle comprising the gas detecting device 40 according to the sixth variant, that is, the fourth variant.

Third Embodiment

Next, a third embodiment will be described. Also in the third embodiment, there are provided the same gas detecting device 10 and the same autoventilation system 100 for a vehicle comprising the gas detecting device 10 as those in the first embodiment (see FIG. 1). More specifically, the system serves to detect a change in the concentration of an oxidizing gas component such as NOx and to open and close a flap 34 based thereon. However, a different processing flow is executed in a $\mu$C16. In other words, while the different calculating methods are used for the case in which the low concentration signal is being generated and the case in which the high concentration signal is being generated in the first embodiment described above and the like, the calculating methods are specifically varied by using the same calculating equation for the base value B(n) and varying the coefficient thereof. On the other hand, in the third embodiment, a change in a gas concentration is detected by using a differential value during the generation of a low concentration signal. On the other hand, the change in the gas concentration is detected by using the base value B(n) during the generation of the high concentration signal. In the third embodiment, different portions from those of the first embodiment will be mainly described and the description of the same portions will be omitted or simplified.

Figure 21:
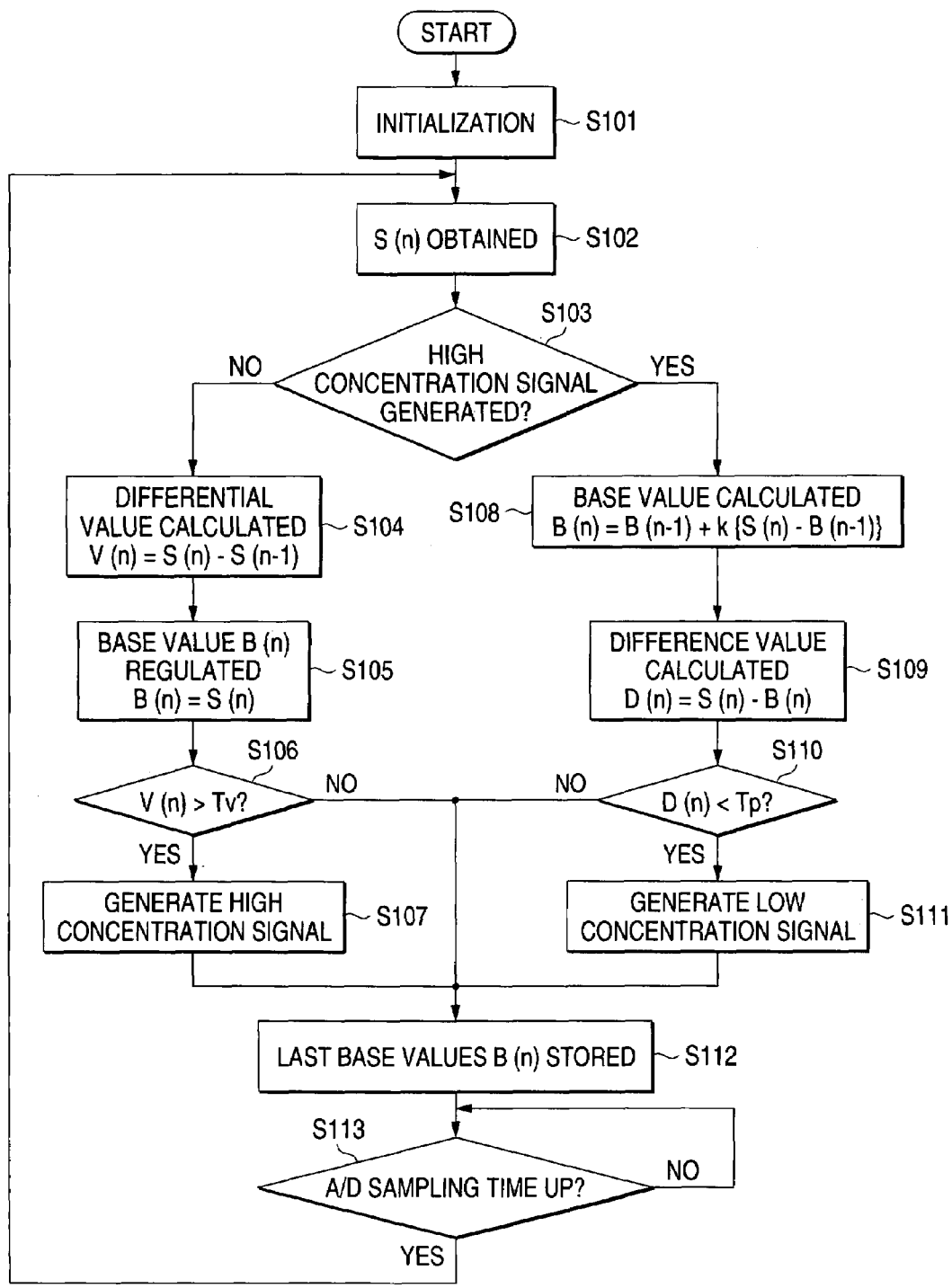
FIG. 21 is a flow chart showing a control in the microcomputer of a gas detecting device according to a third embodiment.

A control in the $\mu$C16 according to the third embodiment will be described in accordance with a flow chart of FIG. 21. When the engine of an automobile is driven, the control system is activated, and a gas sensor element 11 is waited to be brought into an active state and initialization is carried out at Step S101 in the same manner as in the first embodiment. For the initialization, a low concentration signal is generated as a concentration signal LV, more specifically, the concentration signal LV is set to have a low level.

Then, the processing proceeds to Step S102 where a sensor output value S(n) obtained by A/D converting a sensor output potential Vs every 0.4 second is sequentially read. At Step S103, next, it is decided whether or not a high concentration signal indicating that the concentration signal LV has a high level, that is, the concentration of a specific gas (an oxidizing gas in the embodiment) has a high level at the present time is generated. If the decision is No, that is, the concentration of the specific gas is low, the concentration signal LV has the low level and the low concentration signal is generated, the processing proceeds to Step S104. On the other hand, if the decision is Yes, that is, the concentration of the specific gas is high, the concentration signal LV has the high level and the high concentration signal is generated, the processing proceeds to Step S108.

At the Step S104, a differential value V(n) is calculated differently from the first embodiment and the like. More specifically, the differential value V(n) is calculated by using a current sensor output value S(n) and a sensor output value S(n–1) obtained one cycle before (0.4 second before) in accordance with the following equation of V(n)=S(n)–S(n–1), and the processing proceeds to Step S105. The differential value V(n) indicates a change in the sensor output value S(n) which are obtained currently and one cycle before. Accordingly, when the sensor output value S(n) is increased with a rise in the concentration of the oxidizing gas, the change immediately appears on the differential value V(n).

At the Step S105, subsequently, a base value B(n) is regulated. The regulation of the base value in the Step S105 will be described below. Then, the differential value V(n) is compared with a differential threshold Tv at Step S106. When the differential value V(n) is greater than the differential threshold Tv (Yes), the processing proceeds to Step S107 where a high concentration signal is generated in place of a low concentration signal which is currently generated, and the processing proceeds to Step S112. More specifically, the concentration signal LV is changed from a low level to a high level. On the other hand, if the differential value V(n) is equal to or smaller than the differential threshold Tv (No), the processing proceeds to the Step S112.

On the other hand, at the Step S108, the base value B(n) is calculated based on a last base value B(n–1) and the sensor output value S(n) by using the same equation as that in the first embodiment (see in the following) and the processing proceeds to Step S109. B(n)=B(n–1)+k{S(n)–B(n–1)}, wherein a first coefficient k is set to 0<k<1. As described above, the base value B(n) has such a property as to follow the sensor output value S(n) and to be changed more slowly than the sensor output value. In addition, the base value B(n) has the degree of follow-up for the sensor output value S(n) varied depending on the coefficient k to be used, and the base value B(n) follows the sensor output value S(n) comparatively rapidly with a slight delay if the comparatively great first coefficient k is used. On the other hand, if the comparatively small coefficient k is used, the base value B(n) is changed less sensitively and the follow-up is carried out slowly for the sensor output value.

For a period in which the sensor output value S(n) is increased with a rise in the concentration of the oxidizing gas, accordingly, the base value B(n) is not greatly increased as compared with the sensor output value S(n). In other words, the base value B(n) thus calculated is not greatly changed from the last base value B(n–1). Accordingly, the base value is reflected when the low concentration signal is switched into the high concentration signal at the Step S107.

At the Step S105, the regulation for substituting a current sensor output value S(n) for the base value B(n) is carried out. Accordingly, a base value obtained immediately before the switching from the low concentration signal to the high concentration signal (Step S107) is equal to a sensor output value at that time (immediately before the switching). For this reason, the base value calculated subsequently at the Step S108 is gradually changed from the sensor output value acquired immediately before the switching. Thus, the base value B(n) calculated at the Step S108 is obtained by slowly following the change in the sensor output value from the sensor output value obtained immediately before the switching.

A difference value D(n) is calculated in accordance with an equation of D(n)=S(n)−B(n) at the Step S109 and is compared with a PI threshold Tp at Step 110. If the differential value is smaller than the PI threshold Tp, that is, D(n)<Tp is obtained (Yes), the processing proceeds to Step S111 where a low concentration signal is generated in place of the currently generated high concentration signal and the processing proceeds to the Step S112. More specifically, the concentration signal LV is changed from the high level to the low level. On the other hand, if the difference value D(n) is equal to or greater than the PI threshold Tp (No), the processing proceeds to the Step S112.

Then, the processing proceeds from both of the Steps S107 and S111 to the Step S112 where the last values B(n) calculated at the Steps S105 and S108 are stored, and the time up of an A/D sampling time is waited at Step S113 and the processing returns to the Step S102. Thus, when the concentration of the oxidizing gas is greatly increased, the differential value V(n) immediately becomes greater than a differential threshold Tv and a high concentration signal is generated in the early stage of a rise in the concentration. Subsequently, the decision of Yes is obtained at the Step S103 and the processing proceeds to the Step S108 where the base value B(n) is calculated in place of the differential value V(n).

To the contrary, when the concentration of the oxidizing gas is reduced, the difference value D(n) is decreased and a low concentration signal is generated at the Step S111. Then, the decision of No is obtained at the Step S103 and the processing proceeds to the Step S104 where the differential value V(n) is calculated again. Accordingly, even if the concentration of the oxidizing gas is increased again, the increase can be grasped in the early stage of the increase in the gas concentration and a high concentration signal can be generated.

Figure 22:
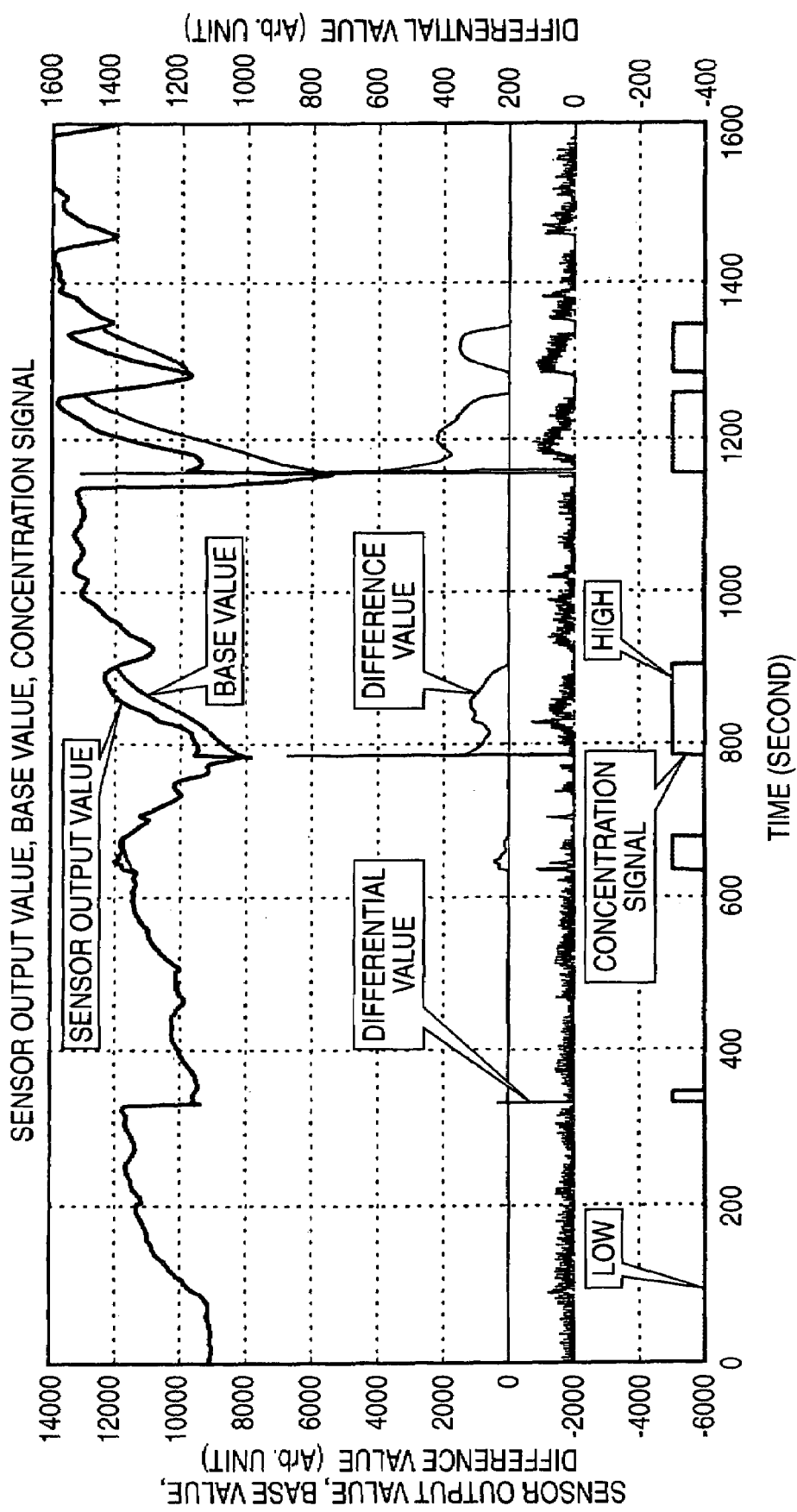
FIG. 22 is a chart showing an example of a sensor output value S(n), and a change in a base value B(n), a difference value (D) and a differential value V(n) and a change in a concentration signal in actual running according to the third embodiment.

Next, FIG. 22 is a graph showing an example of a change in the sensor output value S(n), the base value B(n), the difference value D(n), the differential value V(n) and the concentration signal LV in the case in which a gas detecting device 10 and an autoventilation system 100 for a vehicle which are operated in accordance with the flow chart are applied to gas concentration change data for running on an actual road. Since all of the sensor output value S(n), the differential value V(n), the base value B(n) and the difference value D(n) are numeric values to be processed in the μC16, axes of ordinate on left and right ends in the drawing which indicate the sensor output value, the base value and the difference value denote optional numeric units. For easiness of understanding in the drawing, moreover, only a positive number is used for the differential value V(n) and a unit for each graduation is increased in proportion to the sensor output value and the like as shown in the axis of ordinate on the right end in the drawing. A concentration signal LV shown in a lowermost part is switched in two stages of high/low and an upper portion in the drawing corresponds to a high level. In the embodiment, moreover, description will be given to the case in which the coefficient k=1/64, the differential threshold Tv=100 and the PI threshold Tp=0 are set.

For a period of a time of 0 to 785 seconds, the concentration signal LV has the low level, that is, the low concentration signal is generated except for a part (330 to 345 seconds and 635 to 680 seconds). For this period, the base value B(n)=S(n) is set at the Step S105. Therefore, the sensor output value and the base value are changed in coincidence with each other. In the vicinity of the time of approximately 785 seconds, then, the sensor output value is rapidly increased (like a step). Consequently, the differential value V(n) is immediately increased to exceed the differential threshold Tv. Therefore, the high concentration signal is generated in place of the low concentration signal (that is, the concentration signal is set to have the high level) and the base value B(n) is calculated at the Step S108. Then, when the sensor output value is started to be decreased at a time of approximately 890 seconds, the difference value is also decreased and the difference value becomes equal to or smaller than the PI threshold Tp=0 at a time of approximately 905 seconds. At the Step S111, accordingly, the low concentration signal is generated in place of the high concentration signal.

Also at a time of approximately 1155 to 1260 seconds and a time of approximately 1285 to 1345 seconds, the same operation can be confirmed. In the embodiment, furthermore, an increase in the sensor output value, that is, an increase in the gas concentration is detected based on the differential value V(n) when the low concentration signal is generated as is understood from the relationship between the sensor output value and the base value in the vicinity of the times of approximately 785 seconds, 1155 seconds and 1285 seconds. Therefore, it is apparent that the high concentration signal can be generated in place of the low concentration signal in the very early stage of the increase. While k=1/64 is used for the coefficient k in order to calculate the base value in the graph, the base value follows the sensor output value more slowly by using a smaller coefficient (for example, 1/256 or the like). Therefore, it is possible to carry out switching to the low concentration signal when the sensor output value is further decreased.

(Eleventh Variant)

Next, a variant of the third embodiment will be described below. A gas detecting device 40 and an autoventilation system 140 for a vehicle comprising the gas detecting device 40 according to an eleventh variant have the same structures as those of the first variant (see FIG. 6). Accordingly, while a processing is carried out by almost the same processing flow as that in the third embodiment, there are some differences. More specifically, the gas sensor element of such a type as to increase the concentration of an oxidizing gas component and to increase a sensor resistance value Rs is used as the gas sensor element 11 in the third embodiment. On the other hand, the eleventh variant is different in that a gas sensor element 41 of such a type as to increase the concentration of a reducing gas component and to decrease the sensor resistance value Rs is used. Correspondingly, a sensor resistance value converting circuit 44 according to the eleventh variant is different in that the sensor resistance value Rs is decreased and a sensor output potential Vs is reduced when the concentration of the reducing gas is increased. Furthermore, a processing flowing μC16 is also different slightly. Accordingly, different portions from those of the first variant and the third embodiment will be mainly described and the same portions will be omitted or simplified.

Figure 23:
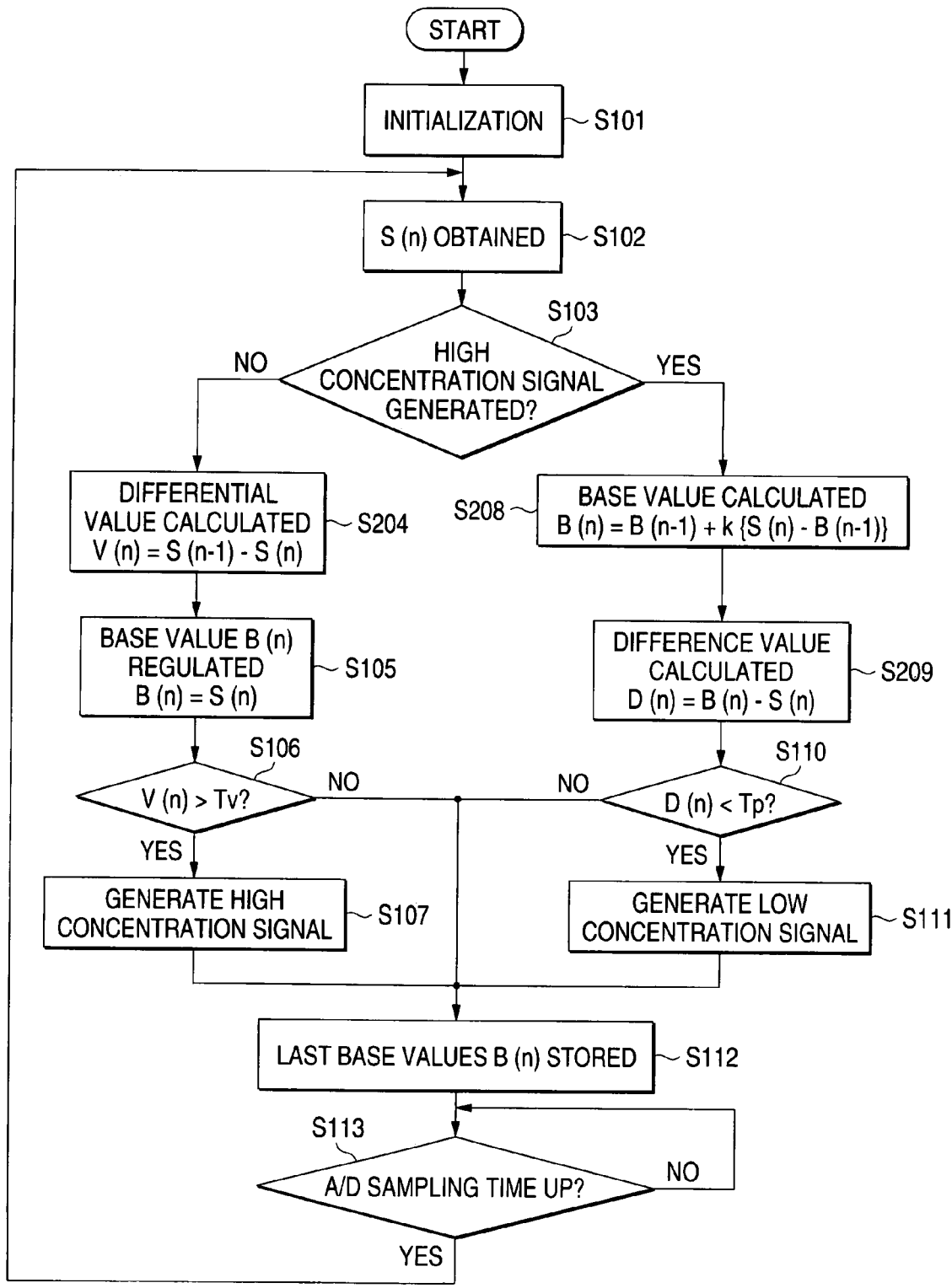
FIG. 23 is a flow chart showing a control in the microcomputer of a gas detecting device according to an eleventh variant.

A control in the μC16 according to the eleventh variant will be described in accordance with a flow chart of FIG. 23. In the same manner as in the third embodiment, Steps S101 to S103 are carried out. If the decision of No is obtained, that is, a low concentration signal is generated at the Step S103, the processing proceeds to Step S204. If the decision of Yes is obtained, that is, a high concentration signal is generated, the processing proceeds to Step S208.

At the Step S204, a differential value V(n) is calculated in the same manner as in the third embodiment. Differently from the Step S104 according to the third embodiment (see FIG. 22), the differential value V(n) is obtained by subtracting a current sensor output value S(n) from a sensor output value S(n−1) obtained one cycle before, that is, in accordance with the following equation of V(n)=S(n−1)−S(n), and the processing proceeds to Step S105. Thus, the differential value V(n) is calculated in order to cause the differential value to be a positive number and to be treated easily when the concentration of the gas is increased. The differential value V(n) indicates a change in the sensor output values S(n) which are obtained one cycle before and currently. Accordingly, when the sensor output value S(n) is decreased with an increase in the concentration of the reducing gas, the change immediately appears on the differential value V(n).

At the Step S105, subsequently, a base value B(n) is regulated. The regulation of the base value in the Step S105 will be described below. Then, the differential value V(n) is compared with a differential threshold Tv at Step S106. When the differential value V(n) is greater than the differential threshold Tv (Yes), the processing proceeds to Step S107 where a high concentration signal is generated in place of a low concentration signal which is currently generated, and the processing proceeds to Step S212. More specifically, the concentration signal LV is changed from a low level to a high level. On the other hand, if the differential value V(n) is equal to or smaller than the differential threshold Tv (No), the processing proceeds to the Step S212.

On the other hand, at the Step S208, the base value B(n) is calculated by using the same equation as that in the first variant (see in the following) and the processing proceeds to Step S209. B(n)=B(n−1)+k{S(n)−B(n−1)}, wherein a coefficient k is set to 0<k<1. The base value B(n) follows the sensor output value S(n) and is changed more slowly than the sensor output value.

For a period in which the sensor output value S(n) is decreased with a rise in the concentration of the reducing gas, accordingly, the base value B(n) is not greatly decreased as compared with the sensor output value S(n). Accordingly, the influence of the base value is reflected when the low concentration signal is switched into the high concentration signal at the Step S207.

At the Step S105, the regulation for substituting a current sensor output value S(n) for the base value B(n) is carried out in the same manner as in the third embodiment. For this reason, the base value calculated subsequently at the Step S208 is gradually changed from the sensor output value acquired immediately before the switching.

At the Step S209, a difference value D(n) is calculated in the same manner as in the third embodiment. The difference value D(n) is calculated in accordance with an equation of D(n)=B(n)−S(n). This is also carried out in order to treat the difference value as a positive number. At Step S210, then, the difference value D(n) is compared with a PI threshold Tp. If D(n)<Tp is obtained (Yes), the processing proceeds to Step S111 where a low concentration signal is generated in place of the high concentration signal which is currently generated, and the processing proceeds to Step S112. On the other hand, D(n)≧Tp is obtained (No), the processing proceeds to the Step S112. Thus, in the case in which the difference value D(n) is smaller than the PI threshold Tp, it is decided that the concentration of the reducing gas is reduced, thereby carrying out switching from the high concentration signal to the low concentration signal. Based on the fact that the difference value D(n) is smaller than the PI threshold Tp, it can be supposed to indicate that the concentration of the reducing gas is reduced.

At the Step S112, then, the last base values B(n) calculated at the Steps S205 and S208 are stored, and the time up of an A/D sampling time is waited at Step S113 and the processing returns to the Step S102. Thus, when the concentration of the reducing gas is greatly increased, the differential value V(n) immediately becomes greater than the differential threshold Tv and a high concentration signal is generated in the early stage of the increase in the concentration. Subsequently, the decision of Yes is obtained at the Step S103 and the processing proceeds to the Step S208 where the base value B(n) is calculated in place of the differential value V(n).

To the contrary, when the concentration of the reducing gas is reduced, the difference value D(n) is decreased and a low concentration signal is generated at the Step S111. Then, the decision of No is obtained at the Step S103 and the processing proceeds to the Step S204 where the differential value V(n) is calculated again. Accordingly, even if the concentration of the reducing gas is increased again, the increase can be grasped in the early stage of the increase in the gas concentration and a high concentration signal can be generated.

Fourth Embodiment

Next, a fifth embodiment will be described. Also in the fifth embodiment, there are provided the same gas detecting device 10 and the same autoventilation system 100 for a vehicle comprising the gas detecting device 10 as those in the first embodiment. More specifically, the system serves to detect a change in the concentration of an oxidizing gas component and to open and close a flap 34 based thereon. In the first embodiment, the base value and the difference value are calculated to detect a change in the concentration of the gas for both a period in which a low concentration signal is generated and a period in which a high concentration signal is generated. On the other hand, the fifth embodiment is different in that m moving average values and a difference value (a first difference value) are calculated for the period in which the low concentration signal is generated and a base value and a difference value (a second difference value) are calculated for the period in which the high concentration signal is generated, thereby detecting a change in the concentration of a gas. Accordingly, different portions from those of the first embodiment will be mainly described and the description of the same portions will be omitted or simplified. In the fifth embodiment, m=100 is set.

Figure 24:
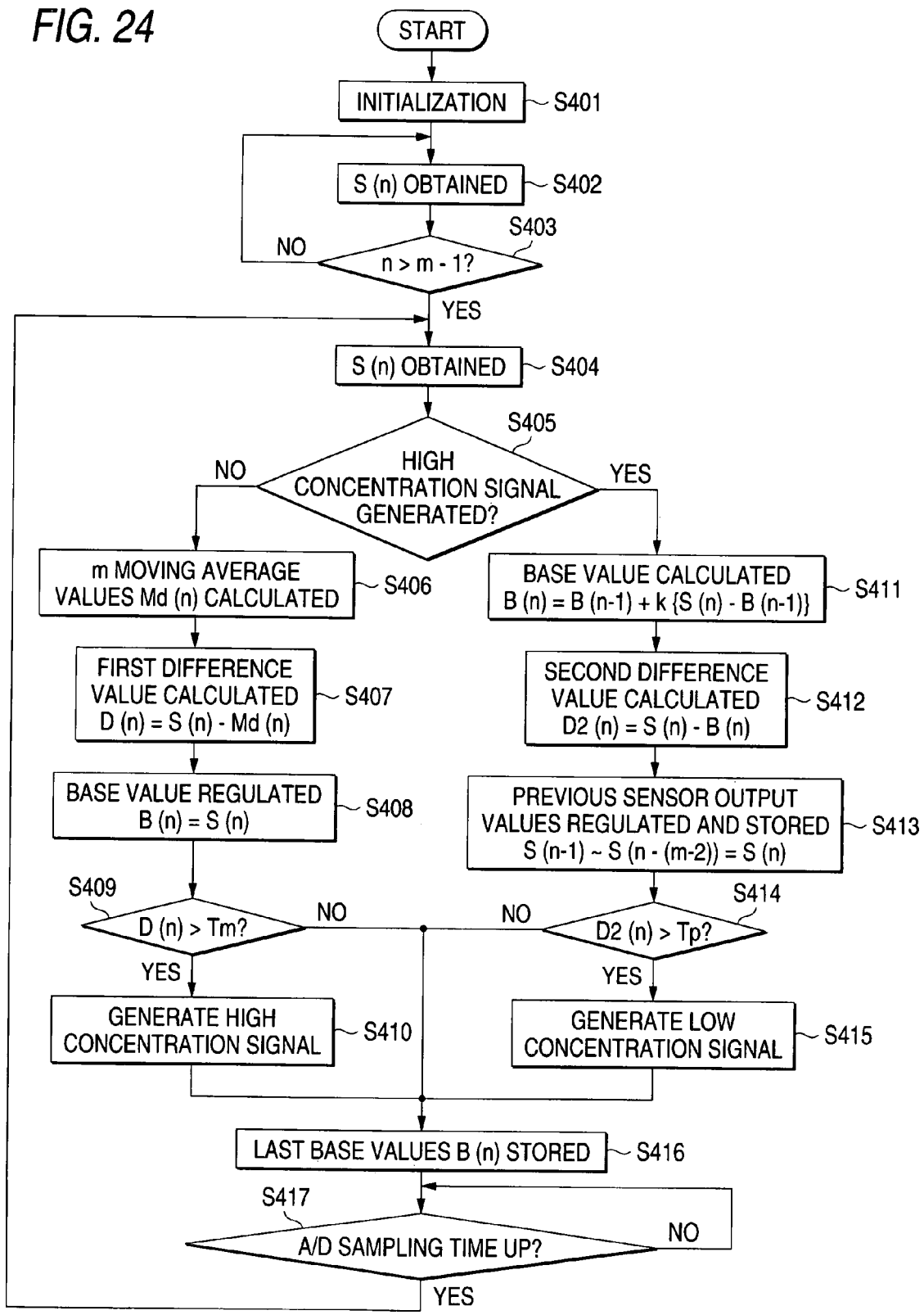
FIG. 24 is a flow chart showing a control in the microcomputer of a gas detecting device according to a fourth embodiment.

A control in a μC16 according to the fifth embodiment will be described in accordance with a flow chart of FIG. 24. When the engine of an automobile is driven, the control system is activated, and a gas sensor element 11 is waited to be brought into an active state and initialization is carried out at Step S401 in the same manner as in the first embodiment. For the initialization, a low concentration signal is generated as a concentration signal LV, more specifically, the concentration signal LV is set to have a low level. Then, the processing proceeds to Step S402 where a sensor output value S(n) obtained by A/D converting a sensor output potential Vs is sequentially read. The processing is repeated until n≧m−1, accordingly, n≧99 is obtained at Step S403. As will be described below, (m−1) (=99) sensor output values are previously obtained in order to calculate the m moving average values (100 moving average values) at Step S406. A time interval of the sensor output values repeatedly acquired at the Steps S402 and S403 is set to 0.4 second in the same as that in the acquirement of a sensor output value which will be described below. Sampling times at the Steps S402 and S403 may be set to be short such that the gas can be detected earlier.

Then, the processing proceeds to Step S404 where a sensor output value S(n) obtained by A/D converting the sensor output potential Vs every 0.4 second is sequentially read. At Step S405, subsequently, it is decided whether or not a high concentration signal indicating that the concentration signal LV has a high level at the present time, that is, the concentration of the oxidizing gas has the high level. If the decision is No, that is, the concentration signal LV has the low level and the low concentration signal is generated, the processing proceeds to Step S406. On the other hand, if the decision is Yes, that is, the concentration signal LV has the high level and the high concentration signal is generated, the processing proceeds to Step S411.

At the Step S406, moving average values (100 moving average values in the fifth embodiment) Md(n) are calculated differently from the first embodiment and the like. More specifically, a average value of m (=100) sensor output values S(n) to S(n−99) is calculated by going back from the present time. More specifically, the average value is calculated by using the following equation of Md(n)=(S(n)+S(n−1)+ . . . +S(n−99))/100 and the processing proceeds to Step S407. The moving average value Md(n) is an average value of 100 sensor output values S(n) obtained by going back from the present time and cannot sufficiently follow a rapid fluctuation in the sensor output values. Accordingly, when the sensor output value S(n) is slowly increased by the drift of the sensor output value which is caused by a change in the temperature of the gas sensor element 11 or the like, for example, the moving average value Md(n) is also increased following the change. However, in the case in which the sensor output value is greatly increased, the moving average value cannot sufficiently follow and is increased with a delay from the sensor output value.

At the Step S407, next, the first difference value D(n) is calculated in accordance with an equation of D(n)=S(n)−Md(n). In the case in which the concentration of the oxidizing gas is maintained to be low and is less changed or the change is carried out slowly, the moving average value md(n) is changed following the sensor output value S(n). Therefore, the first difference value D(n) is not very great. However, when the concentration of the oxidizing gas is greatly raised so that the sensor output value S(n) is greatly increased, the first difference value D(n) is greatly increased because the moving average value Md(n) cannot sufficiently follow. Accordingly, it is decided that D(n)>Tm is obtained at Step S409 which will be described below and a high concentration signal can be generated at Step S410.

Furthermore, a base value B(n) is regulated at Step S408. The regulation of the base value in the Step S408 is carried out for the same reason as that of the Step S105 according to the third embodiment. Then, the first difference value D(n) is compared with a moving average threshold Tm at the Step S409. When the first difference value D(n) is greater than the moving average threshold Tm (Yes), the processing proceeds to the Step S410 where a high concentration signal is generated in place of the low concentration signal which is currently generated, and the processing proceeds to Step S416. More specifically, the concentration signal LV is switched from the low level to the high level. On the other hand, if the first difference value D(n) is equal to or smaller than the moving average threshold Tm (No), the processing proceeds to the Step S416.

Consequently, in the case in which the sensor output value is increased so that the first difference value D(n) becomes greater than the moving average threshold Tm, the increase can be grasped to carry out switching from the low concentration signal to the high concentration signal. In the embodiment, m=100 is set. As a moving average sample number m is increased, the m moving average values Md(n) are changed with more difficulty and slowly follow the sensor output value S(n). To the contrary, when the sample number m is decreased, the moving average values Md(n) follow the sensor output value S(n) comparatively early. Accordingly, it is preferable that the sample number m should be properly selected in consideration of an environment in which the gas detecting device 10 or the like is to be used. Moreover, the relationship between the sample number m and a coefficient k is preferably determined such that the moving average value Md(n) is changed more sensitively than the base value B(n) to be calculated at Step S411 which will be described below for a change in the sensor output value S(n).

On the other hand, at the Step S411, the base value B(n) is calculated by using the same equation as that in the first embodiment (see in the following) and the processing proceeds to Step S412. B(n)=B(n−1)+k{S(n)−B(n−1)}, wherein a coefficient k is set to 0<k<1.

The base value B(n) has such a property as to follow the sensor output value S(n) and to be changed more slowly than the sensor output value. In addition, the degree of follow-up for the sensor output value S(n) can be varied depending on the coefficient k to be used.

For a period in which the sensor output value S(n) is increased with a rise in the concentration of the oxidizing gas, accordingly, the base value B(n) is not greatly increased as compared with the sensor output value S(n). In other words, the base value B(n) thus calculated is not greatly changed from the last base value B(n−1) Accordingly, the influence of the base value is reflected when the low concentration signal is switched into the high concentration signal at the Step S410. At the Step S408, the regulation for substituting a current sensor output value S(n) for the base value B(n) is carried out. Accordingly, a base obtained immediately before the switching from the low concentration signal to the high concentration signal (Step S410) is equal to a sensor output value at that time (immediately before the switching). Moreover, the base value calculated subsequently at the Step S411 is gradually changed from the sensor output value acquired immediately before the switching. Thus, the base value B(n) calculated at the Step S411 is obtained by slowly following the change in the sensor output value from the sensor output value obtained immediately before the switching.

The second difference value D2(n) is calculated in accordance with an equation of D2(n)=S(n)−B(n) at the Step S412. At Step S413, furthermore, the past sensor output values are regulated and stored. More specifically, 99 (=m−1) past sensor output values S(n−1) to S(n−99) are replaced with a current sensor output value S(n). In the case in which a low concentration signal is generated in place of a high concentration signal at the Step S405 as will be described below, a moving average value is then calculated at the Step S406. The moving average value Md(n) to be calculated in that case is caused to approximate to the sensor output value obtained immediately before switching the concentration signal in order to prevent the switching operation from being unstable.

Next, the second difference value D2 (n) is compared with a PI threshold Tp at Step S414. If D2(n)<Tp is obtained (Yes), the processing proceeds to Step S415 where a low concentration signal is generated in place of the high concentration signal which is currently generated, and the processing proceeds to the Step S416. More specifically, the concentration signal LV is switched from the high level to the low level. When the concentration of the oxidizing gas is reduced during the generation of the high concentration signal (Yes in the Step S405), the base value B(n) is decreased with a delay from a decrease in the sensor output value S(n). Therefore, the second difference value D2(n) is gradually decreased. Based on the fact that the second difference value D2 (n) is smaller than the PI threshold Tp, accordingly, it can be supposed to indicate that the concentration of the oxidizing gas is reduced. On the other hand, if the second difference value D2(n) is equal to or greater than the PI threshold Tp (No), the processing proceeds to the Step S416 where the generation of the high concentration signal is maintained.

Then, the processing proceeds from both of the Steps S410 and S415 to the Step S416 where the last base values B(n) calculated at the Steps S408 and S411 are stored, and the time up of an A/D sampling time is waited at Step S417 and the processing returns to the Step S404.

INDUSTRIAL APPLICABILITY

While the invention has been described above in accordance with the embodiments and the variants, it is apparent that the invention is not restricted to the embodiments and the variants but can be properly changed and applied without departing from the scope thereof. For example, although the gas sensor elements 11 and 41 are positioned on the ground side (lower side) of a voltage dividing circuit and the detecting resistor 12 is positioned on the power supply side (upper side) in the embodiments and the variants (see FIGS. 1 and 6), the gas sensor elements 11 and 41 may be positioned on the power supply side of the voltage dividing circuit and the detecting resistor 12 may be positioned on the ground side with a vertical inversion. In such a case, for example, when the concentration of NOx is increased, the sensor voltage Vs is changed to be dropped. Since the characteristic of the sensor resistance converting circuit is thus reversed, it is necessary to carry out a processing corresponding thereto.

While the base value B(n) is calculated in the third embodiment, the eleventh variant and the like, moreover, a moving average value may be calculated in place of the base value. While the differential value V(n) is calculated in the third embodiment and the like, furthermore, a value obtained by a second differential value may be used in addition to the differential value.

In the second, third, seventh, eighth, ninth and tenth variants, moreover, the threshold has a hysteresis and the decision is carried out based on different thresholds for an increase in the concentration level and a reduction in the concentration level in order to prevent the concentration chattering. However, it is also possible to prevent the chattering of the concentration signal and the concentration level signal by other methods. For example, there is a method of once changing the concentration level and then maintaining the same concentration level until a predetermined time passes.

In each of the embodiments and the variants, furthermore, the sensor resistance converting circuits 14 and 44 serve to divide the power potential Vcc by the gas sensor elements 11 and 41 and the detecting resistor 12 and to use the electric potential Vs on the operation point Pd thereof. However, the sensor resistance converting circuit can also have any circuit structure in which a sensor output potential corresponding to the sensor resistance value Rs of the gas sensor element is output.

The invention claimed is:

1. A gas detecting device using a gas sensor element changing an electrical characteristic depending on a concentration of a specific gas, comprising:
    acquiring means for acquiring a sensor output value by using the gas sensor element;
    first deciding means for deciding whether or not a first deciding object value calculated by using the sensor output value satisfies a first relationship for a first threshold;
    second deciding means for deciding whether or not a second deciding object value calculated by using the sensor output value through a different calculating method from the method of calculating the first deciding object value satisfies a second relationship for a second threshold;
    concentration signal generating means for generating either a low concentration signal or a high concentration signal; and
    concentration signal generating means for generating the high concentration signal in place of the low concentration signal when the first relationship is satisfied by the first deciding means for a period in which the low concentration signal is generated, and
    for generating the low concentration signal in place of the high concentration signal when the second relationship is satisfied by the second deciding means for a period in which the high concentration signal is generated.

2. The gas detecting device according to claim 1, further comprising second calculating means for calculating a second difference value to be a difference between the sensor output value and a second calculated value which is calculated by using the sensor output value and carries out follow-up more slowly than the sensor output value when the sensor output value is changed,
    the second deciding means for deciding whether or not the second difference value to be the second deciding object value satisfies the second relationship for the second threshold.

3. The gas detecting device according to claim 2, further comprising first calculating means for calculating a first difference value to be a difference between the sensor output value and a first calculated value which is calculated by using the sensor output value and carries out follow-up more sensitively than the second calculated value when the sensor output value is changed,
    the first deciding means for deciding whether or not the first difference value to be the first deciding object value satisfies the first relationship for the first threshold.

4. A gas detecting device using a gas sensor element changing an electrical characteristic depending on a concentration of a specific gas, comprising:
    acquiring means for acquiring a sensor output value by using the gas sensor element;

concentration level signal switching generating means for switching and generating a plurality of concentration level signals corresponding to a plurality of concentration levels, respectively;

first deciding means for deciding whether or not a first deciding object value calculated by using the sensor output value satisfies a first relationship for a first threshold; and second deciding means for deciding whether or not a second deciding object value calculated by using the sensor output value through a different calculating method from the method of calculating the first deciding object value and a plurality of interlevel thresholds corresponding to interlevel boundaries between the concentration levels with one to one satisfy predetermined relationships, respectively;

wherein the concentration level signal switching generating means generates a concentration level signal corresponding to a concentration level which is higher than the lowest concentration level by one rank in place of a concentration level signal corresponding to the lowest concentration level when the first relationship is satisfied by the first deciding means for a period in which the concentration level signal corresponding to the lowest concentration level is generated, and generates the concentration level signal corresponding to a higher concentration level than a current concentration level when the second deciding object value satisfies the predetermined relationship for the interlevel threshold corresponding to the interlevel boundary between the current concentration level and the concentration level which is higher than the current concentration level by one rank, and generates the concentration level signal corresponding to a lower concentration level than the current concentration level when the second deciding object value does not satisfy the predetermined relationship for the interlevel threshold corresponding to the interlevel boundary between the current concentration level and the concentration level which is lower than the current concentration level by one rank.

5. A gas detecting device using a gas sensor element changing a sensor resistance depending on a concentration of a specific gas, comprising:

a sensor resistance value converting circuit for outputting a sensor output potential depending on a change in a sensor resistance value by conducting to the gas sensor element, the sensor output potential being raised when the concentration of the specific gas is increased;

A/D converting means for A/D converting the sensor output potential every predetermined time, thereby acquiring a sensor output value;

first base value calculating means for calculating a base value from the sensor output value in accordance with the following equation (1), $$B(n)=B(n-1)+k1\{S(n)-B(n-1)\} \quad (1)$$

wherein S(n) represents a sensor output value, B(n) represents a base value, k1 represents a first coefficient, 0<k1<1 is set, and n is an integer indicative of an order of time series;

difference value calculating means for calculating a difference value D(n) from the sensor output value S(n) and the base value B(n) in accordance with the following equation (2), $$D(n)=S(n)-B(n) \quad (2)$$

wherein D(n) represents a difference value;

concentration signal generating means for generating either a low concentration signal or a high concentration signal, the concentration signal generating means generating the high concentration signal when the difference value is greater than a predetermined concentration threshold; and second base value calculating means for calculating the base value B(n) from the sensor output value S(n) in accordance with the following equation (3) in place of the equation (1) for a period in which the high concentration signal is generated, $$B(n)=B(n-1)+k2\{S(n)-B(n-1)\} \quad (3)$$

wherein k2 represents a second coefficient and $0 \leq k2 < k1 < 1$ is set.

6. The gas detecting device according to claim 5, wherein the second coefficient k2 is set to k2>0.

7. A gas detecting device using a gas sensor element changing a sensor resistance depending on a concentration of a specific gas, comprising:

a sensor resistance value converting circuit for outputting a sensor output potential depending on a change in a sensor resistance value by conducting to the gas sensor element, the sensor output potential being raised when the concentration of the specific gas is increased;

A/D converting means for A/D converting the sensor output potential every predetermined time, thereby acquiring a sensor output value;

first base value calculating means for calculating a base value from the sensor output value in accordance with the following equation (1), $$B(n)=B(n-1)+k1\{S(n)-B(n-1)\} \quad (1)$$

wherein S(n) represents a sensor output value, B(n) represents a base value, k1 represents a first coefficient, 0<k1<1 is set, and n is an integer indicative of an order of time series;

difference value calculating means for calculating a difference value from the sensor output value and the base value in accordance with the following equation (2), $$D(n)=S(n)-B(n) \quad (2)$$

wherein D(n) represents a difference value;

concentration level signal switching generating means for switching and generating a plurality of concentration level signals corresponding to a plurality of concentration levels, respectively, the concentration level signal switching generating means having a plurality of interlevel thresholds which correspond to level boundaries between a plurality of concentration levels with one to one and are increased corresponding to higher concentration interlevel boundaries, generating the concentration level signal corresponding to a higher concentration level than a current concentration level when the difference value is greater than the interlevel threshold corresponding to the interlevel boundary between the current concentration level and the concentration level which is higher than the current concentration level by one rank, and generating the concentration level signal corresponding to a lower concentration level than a current concentration level when the difference value is smaller than the interlevel threshold corresponding to the interlevel boundary between the current concentration level and the concentration level which is lower than the current concentration level by one rank; and second base value calculating means for calculating a base value from the sensor output value in accordance with the following equation (3) in place of the equation (1) for a period in which a concentration level signal corresponding to a higher concentration level than a predetermined concentration level is generated by the concentration level signal switching generating means, $$B(n)=B(n-1)+k2\{S(n)-B(n-1)\} \qquad (3)$$

wherein k2 represents a second coefficient and $0 \leq k2 < k1 < 1$ is set.

8. The gas detecting device according to claim 7, wherein the predetermined concentration level in the second base value calculating means is the lowest one of the concentration levels.

9. The gas detecting device according to claim 8, wherein the second coefficient k2 is set to k2>0.

10. The gas detecting device according to claim 7, wherein the second coefficient k2 is set to k2>0.

11. A gas detecting device using a gas sensor element changing a sensor resistance depending on a concentration of a specific gas, comprising:

a sensor resistance value converting circuit for outputting a sensor output potential depending on a change in a sensor resistance value by conducting to the gas sensor element, the sensor output potential being raised when the concentration of the specific gas is increased, A/D converting means for A/D converting the sensor output potential every predetermined time, thereby acquiring a sensor output value;

third base value calculating means for calculating a base value from the sensor output value in accordance with the following equation (4), $$B(n)=B(n-1)+k3\{S(n)-B(n-1)\} \qquad (4)$$

wherein S(n) represents a sensor output value, B(n) represents a base value, k3 represents a third coefficient, $0<k3<1$ is set, and n is an integer indicative of an order of time series;

difference value calculating means for calculating a difference value D(n) from the sensor output value S(n) and the base value B(n) in accordance with the following equation (5), $$D(n)=B(n)-S(n) \qquad (5)$$

wherein D(n) represents a difference value;

concentration signal generating means for generating either a low concentration signal or a high concentration signal, the concentration signal generating means generating the high concentration signal when the difference value is greater than a predetermined concentration threshold; and fourth base value calculating means for calculating the base value B(n) from the sensor output value S(n) in accordance with the following equation (6) in place of the equation (4) for a period in which the high concentration signal is generated, $$B(n)=B(n-1)+k4\{S(n)-B(n-1)\} \qquad (6)$$

wherein k4 represents a fourth coefficient and $0 \leq k4 < k3 < 1$ is set.

12. The gas detecting device according to claim 11, wherein the fourth coefficient k4 is set to k4>0.

13. A gas detecting device using a gas sensor element changing a sensor resistance depending on a concentration of a specific gas, comprising:

a sensor resistance value converting circuit for outputting a sensor output potential depending on a change in a sensor resistance value by conducting to the gas sensor element, the sensor output potential being reduced when the concentration of the specific gas is increased;

A/D converting means for A/D converting the sensor output potential every predetermined time, thereby acquiring a sensor output value;

third base value calculating means for calculating a base value from the sensor output value in accordance with the following equation (4), $$B(n)=B(n-1)+k3\{S(n)-B(n-1)\} \qquad (4)$$

wherein S(n) represents a sensor output value, B(n) represents a base value, k3 represents a third coefficient, $0<k3<k1$ is set, and n is an integer indicative of an order of time series;

difference value calculating means for calculating a difference value from the sensor output value and the base value in accordance with the following equation (5), $$D(n)=B(n)-S(n) \qquad (5)$$

wherein D(n) represents a difference value;

concentration level signal switching generating means for switching and generating a plurality of concentration level signals corresponding to a plurality of concentration levels, respectively, the concentration level signal switching generating means having a plurality of interlevel thresholds which correspond to level boundaries between a plurality of concentration levels with one to one and are increased corresponding to higher concentration interlevel boundaries, generating the concentration level signal corresponding to a higher concentration level than a current concentration level when the difference value is greater than the interlevel threshold corresponding to the interlevel boundary between the current concentration level and the concentration level which is higher than the current concentration level by one rank, and generating the concentration level signal corresponding to a lower concentration level than a current concentration level when the difference value is smaller than the interlevel threshold corresponding to the interlevel boundary between the current concentration level and the concentration level which is lower than the current concentration level by one rank; and fourth base value calculating means for calculating a base value from the sensor output value in accordance with the following equation (6) in place of the equation (4) for a period in which a concentration level signal corresponding to a higher concentration level than a predetermined concentration level is generated by the concentration level signal switching generating means, $$B(n)=B(n-1)+k4\{S(n)-B(n-1)\} \qquad (6)$$

wherein k4 represents a fourth coefficient and $0 \leq k4 < k3 < 1$ is set.

14. The gas detecting device according to claim 13, wherein the predetermined concentration level in the fourth base value calculating means is the lowest one of the concentration levels.

15. The gas detecting device according to claim 14, wherein the fourth coefficient k4 is set to k4>0.

16. The gas detecting device according to claim 13, wherein the fourth coefficient k4 is set to k4>0.

17. A gas detecting device using a gas sensor element changing a sensor resistance depending on a concentration of a specific gas, comprising:

a sensor resistance value converting circuit for outputting a sensor output potential depending on a change in a sensor resistance value by conducting to the gas sensor element, the sensor output potential being raised when the concentration of the specific gas is increased;

A/D converting means for A/D converting the sensor output potential every predetermined time, thereby acquiring a sensor output value;

differential value calculating means for calculating a differential value from the sensor output value in accordance with the following equation (7), $$V(n)=S(n)-S(n-1) \tag{7}$$

wherein S(n) represents a sensor output value, V(n) represents a differential value, and n is an integer indicative of an order of time series;

base value calculating means for calculating a base value B(n) from the sensor output value S(n) in accordance with the following equation (8), $$B(n)=B(n-1)+k\{S(n)-B(n-1)\} \tag{8}$$

wherein k represents a coefficient and 0<k<1 is set;

difference value calculating means for calculating a difference value D(n) from the sensor output value S(n) and the base value B(n) in accordance with the following equation (9); and $$D(n)=S(n)-B(n) \tag{9}$$

concentration signal generating means for generating either a low concentration signal or a high concentration signal, the concentration signal generating means generating the high concentration signal when the differential value V(n) is greater than a first threshold for a period in which the low concentration signal is generated and generating the low concentration signal when the difference value D(n) is smaller than a second threshold for a period in which the high concentration signal is generated.

18. A gas detecting device using a gas sensor element changing a sensor resistance depending on a concentration of a specific gas, comprising:

a sensor resistance value converting circuit for outputting a sensor output potential depending on a change in a sensor resistance value by conducting to the gas sensor element, the sensor output potential being reduced when the concentration of the specific gas is increased;

A/D converting means for A/D converting the sensor output potential every predetermined time, thereby acquiring a sensor output value;

differential value calculating means for calculating a differential value from the sensor output value in accordance with the following equation (10), $$V(n)=S(n-1)-S(n) \tag{10}$$

wherein S(n) represents a sensor output value, V(n) represents a differential value, and n is an integer indicative of an order of time series;

base value calculating means for calculating a base value B(n) from the sensor output value S(n) in accordance with the following equation (11), $$B(n)=B(n-1)+k\{S(n)-B(n-1)\} \tag{11}$$

wherein k represents a coefficient and 0<k<1 is set;

difference value calculating means for calculating a difference value D(n) from the sensor output value S(n) and the base value B(n) in accordance with the following equation (12); and $$D(n)=B(n)-S(n) \tag{12}$$

concentration signal generating means for generating either a low concentration signal or a high concentration signal, the concentration signal generating means generating the high concentration signal when the differential value V(n) is greater than a first threshold for a period in which the low concentration signal is generated and generating the low concentration signal when the difference value D(n) is smaller than a second threshold for a period in which the high concentration signal is generated.

19. The autoventilation system for a vehicle comprising the gas detecting device according to any of claims 1 to 18.

\* \* \* \* \*

UNITED STATES PATENT AND TRADEMARK OFFICE
CERTIFICATE OF CORRECTION

PATENT NO. : 7,266,459 B2
APPLICATION NO. : 10/048535
DATED : September 4, 2007
INVENTOR(S) : Yuji Kimoto et al.

It is certified that error appears in the above-identified patent and that said Letters Patent is hereby corrected as shown below:

Column 38, line 42, change "increasing" to --decreasing--.

Column 40, line 27, change "increased" to --decreased--.

Column 41, line 1, change "increasing" to --decreasing--.

Column 59, line 28, change "raised" to --reduced--.

Column 59, line 65, change "0☐k4<k3<1" to --0≦k4<k3<1--.

Signed and Sealed this

Nineteenth Day of May, 2009

JOHN DOLL
*Acting Director of the United States Patent and Trademark Office*